(12) United States Patent
Xu et al.

(10) Patent No.: US 7,700,095 B2
(45) Date of Patent: Apr. 20, 2010

(54) DETECTION, ISOLATION AND USES OF RENALASE (MONOAMINE OXIDASE C)

(75) Inventors: Jianchao Xu, Bethany, CT (US); Gary Desir, Woodbridge, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/593,099

(22) PCT Filed: Mar. 21, 2005

(86) PCT No.: PCT/US2005/009248

§ 371 (c)(1),
(2), (4) Date: Jul. 5, 2007

(87) PCT Pub. No.: WO2005/089505

PCT Pub. Date: Sep. 29, 2005

(65) Prior Publication Data

US 2007/0275083 A1    Nov. 29, 2007

Related U.S. Application Data

(60) Provisional application No. 60/554,552, filed on Mar. 19, 2004, provisional application No. 60/615,452, filed on Oct. 1, 2004.

(51) Int. Cl.
*A61K 38/44* (2006.01)
*C12N 9/02* (2006.01)
*C12Q 1/00* (2006.01)
*C12P 21/04* (2006.01)
*C12N 1/20* (2006.01)
*C07H 21/04* (2006.01)
*C12Q 1/68* (2006.01)

(52) U.S. Cl. ............ 424/94.4; 435/189; 435/4; 435/6; 435/69.1; 435/71.1; 435/252.3; 435/320.1; 435/440; 536/23.2

(58) Field of Classification Search .......... None
See application file for complete search history.

(56) References Cited

U.S. PATENT DOCUMENTS

| | | |
|---|---|---|
| 2004/0005685 A1 | 1/2004 | Olandt et al. |
| 2006/0286078 A1 | 12/2006 | Humes |
| 2007/0248585 A1 | 10/2007 | Desir et al. |

FOREIGN PATENT DOCUMENTS

| | | |
|---|---|---|
| EP | 1074617 A | 2/2001 |
| WO | WO 99/19495 | 4/1999 |
| WO | WO 00/04140 | 1/2000 |
| WO | WO 01 /11053 | 2/2001 |
| WO | WO 01/57190 A2 * | 2/2001 |
| WO | WO 01/57190 A2 * | 8/2001 |
| WO | WO 01/92581 | 12/2001 |
| WO | WO 02/068579 | 9/2002 |

OTHER PUBLICATIONS

Gottowik et al. Characterisation of wild-type and mutant forms of human monoamine oxidase A and B expressed in a mammalian cell line. FEBS Lett. Feb. 8, 1993;317(1-2):152-6.*
Branden et al. Introduction to Protein Structure, Garland Publishing Inc., New York, p. 247, 1991.*
Grimsby et al., Human monoamine oxidase A and B genes exhibit identical exon-intron organization, Proceedings of the National Academy of Sciences USA (Neurobiology), vol. 88, pp. 3637-3641, May 1991, Los Angeles, CA.
Li, et al, High-Level Expression of Human Liver Monoamine Oxidase A in *Pichia pastoris*: Comparison with the Enzyme Expressed in *Saccharomyces cerevisiae* Protein Expression and Purification 24, 152-162 (2002).
Billett et al., Monoamine oxidase (MAO) in human peripheral tissues., Neurotoxicology. Jan. 2004;25 (1-2):139-48. Review.
Deloukas et al., The DNA sequence and comparative analysis of human chromosome 10, Nature, 429 (6990): 375-381 (May 27, 2004).
Elmore et al., Human kidney diamine oxidase: heterologous expression, purification, and characterization., J. Biol. Inorg. Chem. Jun. 2002;7(6):565-79. Epub Feb. 13, 2002.
Guimaraes et al. Differential substrate specificity of monoamine oxidase in the rat heart and renal cortex., Life Sci. Jul. 11, 2003;73(8):955-67.
Krause et al., Human kidney flavin-containing monooxygenases and their potential roles in cysteine s-conjugate metabolism and nephrotoxicity., J. Pharmacol. Exp. Ther. Jan. 2003;304(1):185-91.
Kunduzova et al., Regulation of JNK/ERK activation, cell apoptosis, and tissue regeneration by monoamine oxidases after renal ischemia-reperfusion., FASEB J. Jul. 2002;16(9):1129-31. Epub May 21, 2002.
Luft F.C., Renalase, a catecholamine-metabolizing hormone from the kidney., Cell Metab. Jun. 2005; 1(6):358-60.
Mitoma et al., Mitochondrial targeting signal of rat liver monoamine oxidase B is located at its carboxy terminus., J. Biochem. (Tokyo). Jan. 1992; 111(1): 20-4.
Ota et al., Complete sequencing and characterization of 21,243 full-length human cDNAs, Nature Genetics, 36(1), 40-45 (Jan. 1, 2004).
Pizzinat et al., The renal monoamine oxidases: pathophysiology and targets for therapeutic intervention., Curr. Opin. Nephrol. Hypertens. Jan. 1998;7(1):33-6. Review.
Strausberg et al., Generation and Initial Analysis of more than 15,000 full-length human and mouse cDNA sequences. Proc. Natl. Acad. Sci., (USA) 99(26), 16899-16903 (2002).
Xu et al., Renalase is a novel, soluble monoamine oxidase that regulates cardiac function and blood pressure., J. Clin Invest. May 2005; 115(5):1275-80. Epub Apr. 7, 2005.
GenBank Accession No. BC005364.
GenBank Accession No. AK002080.
GenBank Accession No. NM_018363.
GenBank Accession No. BX648154.

(Continued)

*Primary Examiner*—Yong D Pak
(74) *Attorney, Agent, or Firm*—Cooley Godward Kronish LLP

(57) ABSTRACT

The present invention provides for the identification, isolation and uses of mammalian Monoamine Oxidase C (MAO-C), also known as renalase.

18 Claims, 16 Drawing Sheets

OTHER PUBLICATIONS

Yao, et al., Expression of KCNA10, a Voltage-Gated K Channel, in Glomerular Endothelium and at the Apical Membrane of the Renal Proximal Tubule, J AM Soc Nephrol 13: 2831-2839, 2002.

Vaughn, C., Renalase Could Even Survival Odds in Kidney Disease, National Review of Medicine vol. 2 No. 11, Jun. 15, 2005.

Emanuel, J.R., Human Kidney Protein Found that Regulates Heart Contraction and Blood Pressure, Yale News Release, Apr. 8, 2005.

Emanuel, J.R., Researchers Identify a Protein in the Kidney that Regulates Heart Function and Blood Pressure, Yale Bulletin & Calendar, Vo. 32, No. 6, Apr. 15, 2005.

Hartz, P.A., Chromosome 10 Open Reading Frame 59; C10ORF59, Online Mendelian Inheritance in Man, May 24, 2005.

Ritz, E., Kidney and Blood Pressure—The Story Unfolds, J. American Society of Nephrology 16:2521-2527, 2005.

Database EMBL, EBI accession No. AX878137 "Sequence 13042 from Patent EP1074617," (2003).

Database Geneseq [online], EBI accession No. AAK51907 "Human [polynucleotide SEQ ID No. 452," (2001).

Database Geneseq [online], EBI accession No. AAM78774 "Human protein SEQ ID No. 1436," (2001).

Supplemental Search Report issued in related EP Appl. No. 05730232.5 on Jan. 26, 2009, 6pp.

* cited by examiner

```
              v10        v20        v30         v40        v50        v60         v70         v80        v90        v100
RENALASE MAQVLIVGAGMTGSLCAAA--LLRRQTSGPLYLAVWDKADDSGGRMTTACSPHNPQCTADLGAQYITCTPHYAKKHQRFYDEL-L-AYGVLRPLSSPIEGMVMKEGDCNFVA
         |::|  :::|:|||:||||  | :::| ||| |:|::|  :|||  ||:  | :|  |  : :  |:|   |::  |:   |:  :: |::
MAO-A    MFDVVVIGGGISG--LSAAKLLTEYGVSVLVLEARDRV---GGR-TYTIRNEHVDYV--DVGGAYVG--PT-QNRILRLSKELGIETYKV--NVSERLVQYV--KGKTYPFRG
              ^20        ^30        ^40         ^50        ^60         ^70        ^80        ^90         ^100       ^110 v110        v120        v130        v140        v150        v160        v170        v180        v190        v200
P--QGISSIIKHYLKESGAEVYFRHRVTQINLRDDKWEVSKQTGSPEQFDLIVLTMPV--PEIL-QLQGDITTLISECQRQLEAVSYSSRYALGLFYEAGTKI-DVPWAG
|::   :|||:|  |  |:|   |:|::::   | || :| :    :    |:|   :  | |: ::::
AFPPVWNPIA-YLDYNNLWRTIDNMGKEIP-TDAPWE-AQHADKWDKMTMKELIDKICWTKTARREAYLFVNINVTSEPHEVSALWFL--WY-VKQ-CGGTTRIFSVTNGG
     ^120        ^130        ^140        ^150        ^160        ^170        ^180        ^190        ^200        ^210 v210        v220        v230        v240        v250        v260        v270        v280        v290        v300
QERKFVGGSGQVSERIMDLLGDQVKLNHPVTHVDQSSDNIIETLNHEHYECKYVINAIPPTLTAKIHFRPELPAERNQLIQRLPMGAVIKCMYYKEAFWKKKDYC-GC
|  ::: :  ::|      ::::| |::::|    :: |   ::  :|::  ::|  ||::    : |
Q---YI--TSNPCIRFVS-I-DN-K-KRNI-ESSEIGPSLVIHT--TVPFGVTYLEHSI-EDV-QELVFQ-QI--E--NILPGLPQPIATKCQKWRHSQVTNAAANCPGQ
    ^220        ^230        ^240        ^250         ^260        ^270        ^280        ^290        ^300        ^310 v310        v320        v330
MTLHHKPFTACGGDGFTQSNFDGCITSALC-VL
 | :|:|   :||        ||: :  :|
MIIEDED--APISITLDDTKPDGSLPAIMGFIL
     ^330        ^340        ^350
```

*FIG. 1C*

```
                  gcggatcgctgctccctctcgcc
SEQ ID 1  24  atggcgcaggtgctgatcgtgggcgccgggatgacaggaagcttgtgctgaggacgtccggtcccttgtacctt      30
SEQ ID 2  114  M  A  Q  V  L  I  V  G  A  G  M  T  G  S  L  C  A  A  L  R  R  Q  T  S  G  P  L  Y  L
          204 gctgtgtgggacaaggctgacgactcagggggaagaatgactacagcctgcagtcctcatatcctcagtgcacagctgactggtgct      60
               A  V  W  D  K  A  D  D  S  G  G  R  M  T  T  A  C  S  P  H  N  P  Q  C  T  A  D  L  G  A
          294 cagtacatcacctgcactcctcattatgccaaaaaacaccaacgttttatgatgaactgtttagcctatggcgttttgaggcctctaagc   90
               Q  Y  I  T  C  T  P  H  Y  A  K  K  H  Q  R  F  Y  D  E  L  L  A  Y  G  V  L  R  P  L  S
          384 tcgcctattgaaggaatggtgatgaaagaagaggactgtaactttgtgcacctcaaggaatttcttgtgcacctcaaggaatttcttcattattaagcattacttgaaa    120
               S  P  I  E  G  M  V  M  K  E  G  D  C  N  F  V  A  P  Q  G  I  S  S  I  I  K  H  Y  L  K
          474 gaatcaggtgcagaagtgctacttcagacatcgtgttccacaatgccagttcctgcagcttcaaggtgacatcaccacttagtgaatgc    150
               E  S  G  A  E  V  Y  F  R  H  R  V  T  Q  I  N  L  R  D  D  K  W  E  V  S  K  Q  T  G  S
          564 cctgagcagtttgatcttattgttctcacaatggcctactcctcgagatttctgcagttctgagcttcaaggtgacatcaccacttagtgaatgc    180
               P  E  Q  F  D  L  I  V  L  T  M  P  V  P  E  I  L  Q  L  Q  G  D  I  T  T  L  I  S  E  C
          654 caaaggcagcaactggaggctgagctgactactcctctcgatatgtggcctctctttatgaagctgtacgaagattgatgtcctggg     210
               Q  R  Q  Q  L  E  A  V  S  Y  S  S  R  Y  A  L  G  L  F  Y  E  A  G  T  K  I  D  V  P  W
          744 gctgggcagtacatcaccagtaatccctgtccatttggagttacatacttgagtgttacaatactgaaacacagcattgaggatgtgcaagagtgtcttccagcagctg   240
               A  G  Q  Y  I  T  S  N  P  C  I  R  E  V  S  I  D  N  K  K  R  N  I  E  S  S  E  I  G  P
          834 tcccctctgattcacaccactggttcacacactactatggttcatgtcctcagccaattgctaccaaatgaagacattcacaggttacaaatgctgtgccaactgt     270
               S  L  V  I  H  T  T  V  P  F  G  V  T  Y  L  E  H  S  I  E  D  V  Q  E  L  V  F  Q  Q  L
          924 gaaaacatttgcccgggtttgcctgatcacaaatgtgcctcagcaatttcccttgcatggagggggatggattcacaaggttactactgtcagtccaacttgatgctgtcatcactttct     300
               E  N  I  L  P  G  L  P  Q  M  T  L  H  H  K  P  F  L  A  C  G  D  G  F  T  Q  S  N  F  D  G  C  I  T  S
         1014 gccctatgttcctgaagctttaaagaatttatattagtgcctaagaagcaattactgttcttcacttattcatttcatgtgagtat     330
               A  L  C  V  L  E  A  L  K  N  Y  I  *
         1104 ttctgttattgattatttgttcttctattttgctaagaaaattactgaaaaattgttcttcacttattcatttcatgtgagtat
              aaaatcaattttgtaatttgatagtagttacaaccatgtagaatgtcctcacacctgcacctcctactttctgaattgcta
              tgactactcctgttgttgaggaaaaagtgtactaaaaagtggtactaaaaacgactctcaaaaaattacattaatcacaataacagtttgt
              atgccaaaacttgattatcctattcaatttgaataaagaataatcacattatcaaagcccccatcaaaaaaaaaaaaaaa
         1374 aaaaaaaaaaaa                                                                             342
```

FIG. 2A

```
        10           20           30          40           50
  1 MENQEKASIAGHMFDVVVIGGGISGLSAAKLITEYGVSLVVLEARDRV---GGRTYTIRN  h.VAO-A
  1 MSNK---------CDVVVVGGGISGMAAKLLHDSGLNVVVLEARDRV---GGRTYTLRN  h.VAO-B
  1 MA--------QVLIVGAGMTGSLQAALIRRQTSGPLYLAVWDKADDSGGRMTIACS    h.VAO-C 60           70          80           90          100          110
 58 EHVD--YVDVGGAYVGPTQNRILRISKELGIETYKVNVSERLVQYVKGKIYPERGAFPPV h.VAO-A
 49 QKVK--YVDLGGSYVGPTQNRILRIAKELGIETYKVNEVERLIHHVKGKSYPFRGPFPPV h.VAO-B
 49 PHNPQCTADLGAQVITCIPH---------Y-AKKHQRFYDELL--AM---GVLRPL     h.VAO-C 120         130         140         150         160         170
116 WNPIAYLDYNNLWRTIDNMGKEIPTDAPWEAQHADKWDKMTMKELIDKICWIKTARRFAY h.VAO-A
107 WNPITYLDHNNFWRTMDDMGREIPSDAPWKAPLAEEWDNMTMKELIDKLCWIESAKQLAT h.VAO-B
 90 SSPI-------------------------EGMVMKE----------------------- h.VAO-C 180         190         200         210         220         230
176 LFVNINVTSEPHEVSALWFLWYVKQCGGTTRIFSVTNGGQERKFVG--GSGQVSERIMDL h.VAO-A
167 LFVNLCVTAETHEVSALWFLWYVKQCGGTTRIISTTNGGQERKFVG--GSGQVSERIMDL h.VAO-B
101 -----------GDC---------------NFVAPQGISSIIKHYLKE             h.VAO-C 240         250         260         270         280         290
234 LGDQVKINHPVTHVDQSSDN--IIIETLNHEHYECKYVINALPPTITAKIHFRPELPAER h.VAO-A
225 LGDRVKIERPVIYTDQTREN--VLVETLNHEMYEAKYVISAIPPTIGMKIHFNEPLPMMR h.VAO-B
122 SGAEMYFRHRVTQINLRDEKWEMSKQIGSPEQFDLIVLTMPVEEILQLQGDITTLISECQ h.VAO-C 300         310         320         330         340         350
292 NGLIQRHPMGAVIKQMMYYKEAEWKKKDYCGCMIIEDEDAPISITLDDTKPDGSLPAIMG h.VAO-A
283 NQMITRVELGSVIKQIVYYKEPFWRKKDYCGTMIIDGEEAPVAYTLDDTKPEGNYAAIMG h.VAO-B
182 RQQLEAVSYSSRYALGLFYEA---------------GIKIDVPWAG--Q           h.VAO-C 360         370         380         390         400         410
352 FILARKADRLAKLHKEIRKKNICELYAKVLGSQEAIHPVHYEEKNWCEEQYSGGCYTAYE h.VAO-A
343 FILAHKARKLARLTKEERLKRLCELYAKVLGSLEAFPVHYEEKNWCEEQYSGGCYTTYE h.VAO-B
214 YITSNPCIRFVSIDNKKRNIESSEIGPSLV----IHTIVPFG-------------VTYL h.VAO-C 420         430         440         450         460
412 PPGIMTQYGRVIRQPVGRIFFAGTETATKWSGYMEGAVEAGERAAREVINGLGK-VTEK- h.VAO-A
403 PPGILTQYGRVIRQPVDRIYFAGTETATHWSGYMEGAVEAGERAAREILHAMGK-IPED- h.VAO-B
256 EHSI---------EDVQELVFQQLE---------------NILPGLPQPLATKC       h.VAO-C 470         480         490         500         510        520
470 DIWVQEPESKDVEAVEITHTEWERNLPSVSGLIKIEGES-I--SVTALGFVLYKYKLLPR h.VAO-A
461 EIWQSEPESVDVPAQPITTTELERHLPSVPGLIRLIGIT-IIFSATALGFTAHKRGLLVR h.VAO-B
286 QKWRHSQVTNAAANCEGQMILHHKPFLACGG----DGETQSNEDGCITSALCVLEALKNY h.VAO-C

527 S                                                            h.VAO-A
520 V                                                            h.VAO-B
342 I                                                            h.VAO-C
```

*FIG. 2C*

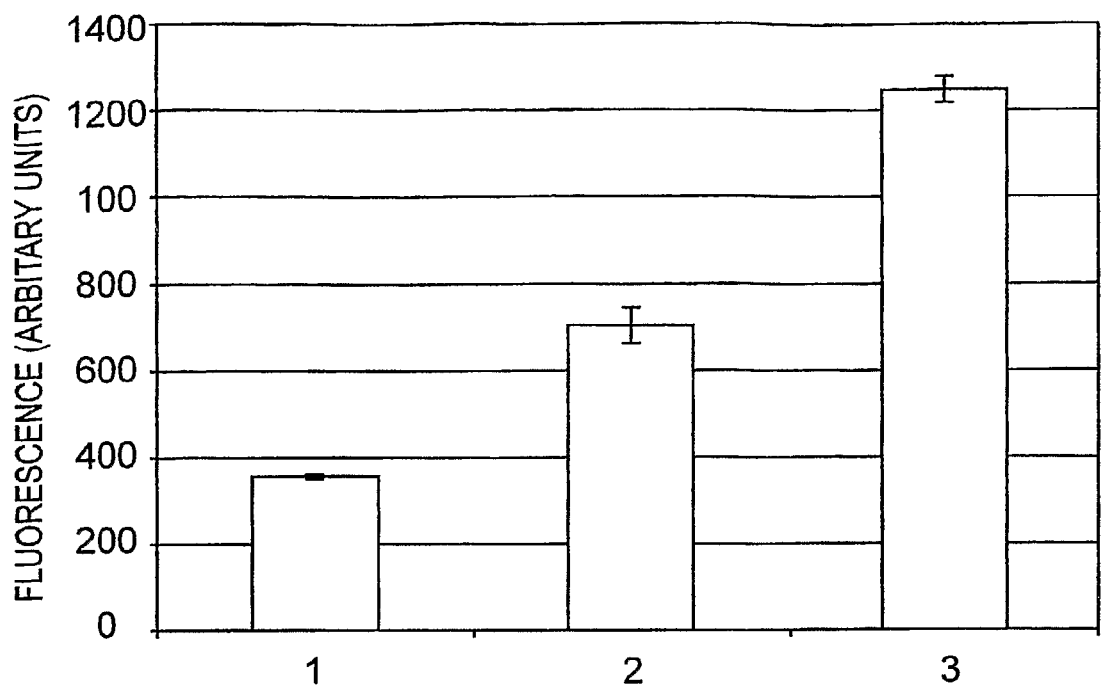
FIG. 4C
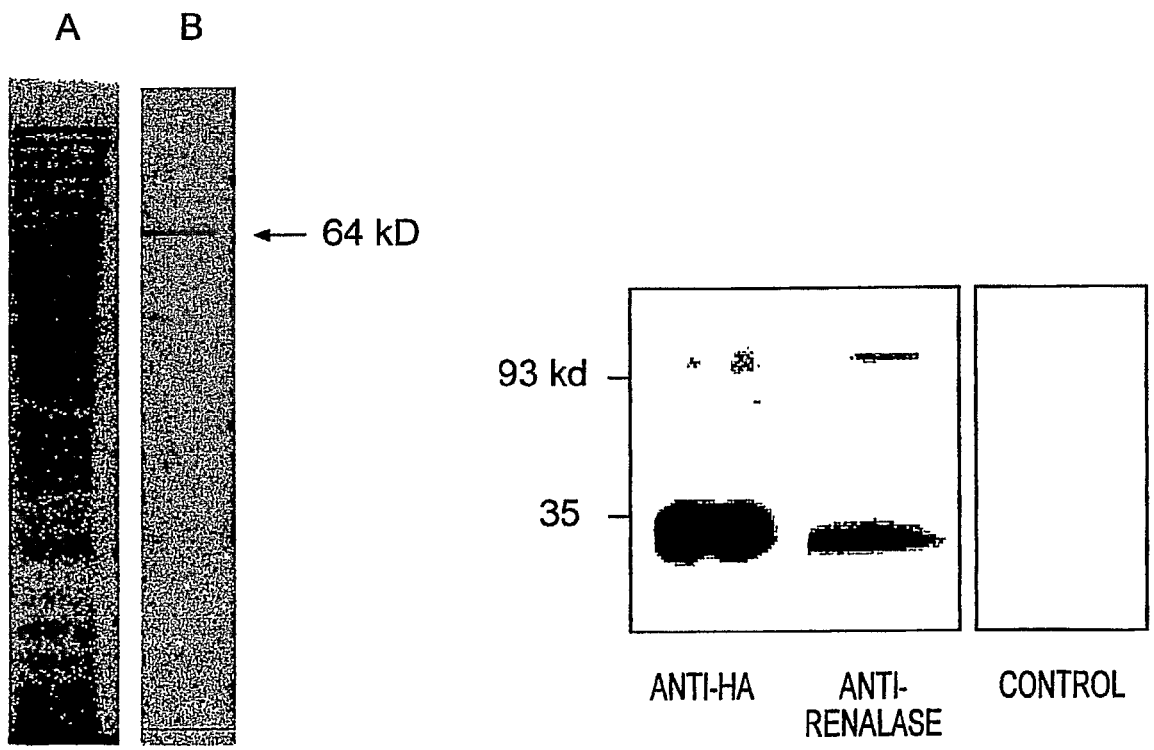
FIG. 4B  FIG. 5A

DETECTION, ISOLATION AND USES OF RENALASE (MONOAMINE OXIDASE C)

CROSS-REFERENCE TO RELATED APPLICATIONS

This application is a National Stage of PCT/US2005/009248, filed Mar. 21, 2005, which is entitled to priority pursuant to 35 U.S.C. §119(e) to U.S. Provisional Patent Application No. 60/554,552, which was filed on Mar. 19, 2004 and to U.S. Provisional Patent Application No. 60/615,452, which was filed on Oct. 1, 2004, all and each of which are incorporated herein in their entireties for all purposes.

STATEMENT REGARDING FEDERALLY SPONSORED RESEARCH OR DEVELOPMENT

This invention was supported in part by funds obtained from the U.S. Government (National Institutes of Health Grant Number K08 DK 0291702), and the U.S. Government may therefore have certain rights in the invention.

BACKGROUND OF THE INVENTION

The regulation of fluid and electrolyte metabolism is a major function of the kidney. Blood enters the kidney through the glomerulus, which filters out cells and proteins and generates, through a process called glomerular filtration, a fluid with an ionic composition identical to that of plasma. The glomerular filtrate then travels through a series of distinct tubular segments, which progressively modify its volume and ionic composition. A large number of factors are known to regulate glomerular filtration including physical forces, local and circulating hormones (Brenner et al. 1976). Similarly, renal tubular reabsorption and secretion are modified by rather complex regulatory processes.

The kidney also serves as an endocrine organ, as it is the main source of erythropoietin, a major determinant of red cell mass that is required for amplification and terminal differentiation of erythroid progenitors and precursors (Line et al., 1985; Jacobs et al., 1985). In addition, the kidney appears to be the most important site for renin release. A fall in blood flow, increased sympathetic stimulation, or a decrease in sodium delivery to the distal tubules can stimulate the release of renin, an enzyme that cleaves angiotensinogen to angiotensin I. The renin-angiotensin system is a key regulator of fluid and electrolyte metabolism, blood pressure, and cardiac function.

Among these many functions carried out by the kidney, the importance of understanding the kidney endocrine function is underscored by the discovery of erythropoietin. There is evidence to suggest that the kidney has complex endocrine functions beyond secretion of renin and erythropoietin. The identification of previously unknown proteins/hormones that are secreted by the kidney will not only provide a more complete understanding of renal physiology but may also significantly improve the way we treat patients with end-stage renal diseases (ESRD).

Patients who develop end-stage renal disease are either treated with renal replacement therapy, such as peritoneal or hemodialysis, or given a renal transplantation. Current renal replacement therapy such as hemodialysis for patients with end-stage renal disease has been the only successful long-term ex vivo organ substitution therapy to date. Despite the success of dialysis at prolonging life, the morbidity and mortality associated with this therapy are undesirably high, and most patients suffer from a poor quality of life (Humes et al., 1995; Wolfe et al. 1999). For example, these patients have increased prevalence of hypertension, cardiovascular diseases such as asymptomatic left ventricular dysfunction, chronic congestive heart failure and atherosclerosis, contributing the most common cause of death among them. While the reasons for this are not entirely clear, it is generally believed that the procedure fails to replicate important functions of the natural organ. The procedure uses an extracorporeal "artificial kidney" to remove excess water and soluble wastes from the blood but does not replicate the important absorptive, metabolic, endocrine, and immunological functions of the natural organ.

It is well documented that patients with ESRD are at significantly higher risk for developing cardiovascular disease, a risk that appears to be correlated with increased oxidative stress (Oberge et al. 2004) and heightened sympathetic tone (Koomans et al., 2004; Joles et al., 2004). Despite the fact that various proteins/hormones have been implicated in ESRD, very few factors involved in ESRD have been identified and characterized. Nevertheless, the identification of such factors is crucial in the development of diagnostics and therapeutics for treatment of ESRD and vascular diseases associated or proteins/hormones secreted by the kidney. Thus, there is long-felt need for the identification and characterization of factors associated with ESRD.

Monoamine oxidase (MAO) is a flavin-adenosine-dinucleotide (FAD)-containing enzyme which converts biogenic amines to their corresponding aldehydes. MAO is present as two isoforms (MAO-A (SEQ ID NO: 11) and MAO-B (SEQ ID NO: 13)), which are separate gene products, that exhibit more than 70% sequence identity and distinct but overlapping substrate specificities in the catabolism of neurotransmitters, such as dopamine, serotonin and norepinephrine (2,3). Both MAO-A and MAO-B are implicated in a large number of neurological disorders and are targets for drugs against Parkinson's disease and depression (4). Mammalian MAOs are bound to the outer mitochondrial membrane and have a FAD molecule covalently bound to the protein via an 8α-thioether linkage to a cysteinyl residue (5). They are expressed in both a tissue-dependent and an age-dependent manner and have been the subject of extensive clinical and pharmacological studies.

MAO-A and MAO-B are anchored through the carboxyl terminus to the outer mitochondrial membrane (Binda et al., 2002). They have overlapping substrate specificity, catabolize neurotransmitters such as epinephrine, norepinephrine, serotonin and dopamine, and are specifically inhibited by pargyline and clorgyline. Polyamine oxidase (PAO), the other known FAD-containing oxidase, is an intracellular oxidase that metabolizes spermine and spermidine, and regulates cell growth (Jalkanen et al., 2001). The crystal structure of human MAO-B has been solved at a resolution of 3.0 A, and reveals a dimer with the FAD cofactor covalently bound to a cysteine side chain (Cys-397) (Binda et al., 2002). MAO-A and MAO-B are coded by adjoining, but separate, genes on the X chromosome, that exhibit over 70% sequence identity and distinct but overlapping substrate specificities in the catabolism of neurotransmitters.

MAO-A and MAO-B differ in tissue distribution, structure and substrate specificity. MAO-A has higher affinity for serotonin, octopamine, adrenaline, and noradrenaline; whereas the natural substrates for MAO-B are phenylethylamine and tyramine. Dopamine is thought to be oxidized by both isoforms. MAO-A and MAO-B are widely distributed in several organs including brain (A. M. Cesura and A. Pletscher, Prog. Drug Research 1992, 38, 171-297). Brain MAO-B activity appears to increase with age. This increase has been attributed to the gliosis associated with aging (C. J. Fowler et al., J. Neural. Transm. 1980, 49, 1-20). Additionally, MAO-B activity is significantly higher in the brains of patients with Alzheimer's disease (P. Dostert et al., Biochem. Pharmacol. 1989, 38, 555-561) and it has been found to be highly expressed in astrocytes around senile plaques (Saura et al., Neuroscience 1994, 70, 755-774). In this context, since oxidative deamination of primary monoamines by MAO produces $NH_3$, aldehydes and $H_2O_2$, agents with established or potential toxicity, it is suggested that there is a rationale for the use of selective MAO-B inhibitors for the treatment of dementia and Parkinson's disease. Inhibition of MAO-B causes a reduction in the enzymatic inactivation of dopamine and thus prolongation of the availability of the neurotransmitter in dopaminergic neurons. The degeneration processes associated with age and Alzheimer's and Parkinson's diseases may also be attributed to oxidative stress due to increased MAO activity and consequent increased formation of $H_2O_2$ by MAO-B. Therefore, MAO-B inhibitors may act by both reducing the formation of oxygen radicals and elevating the levels of monoamines in the brain.

Given the implication of MAO-B in the neurological disorders mentioned above, there is considerable interest to obtain potent and selective inhibitors that would permit control over this enzymatic activity. The pharmacology of some known MAO-B inhibitors is for example discussed by D. Bentue-Ferrer et al. in CNS Drugs 1996, 6, 217-236. Whereas a major limitation of irreversible and non-selective MAO inhibitor activity is the need to observe dietary precautions due to the risk of inducing a hypertensive crisis when dietary tyramine is ingested, as well as the potential for interactions with other medications (D. M. Gardner et al., J. Clin. Psychiatry 1996, 57, 99-104), these adverse events are of less concern with reversible and selective MAO inhibitors, in particular of MAO-B.

By inhibiting MAO activity, MAO inhibitors can regulate the level of monoamines and their neurotransmitter release in different brain regions and in the body (including dopamine, norepinephrine, and serotonin). Thus, MAO inhibitors can affect the modulation of neuroendocrine function, respiration, mood, motor control and function, focus and attention, concentration, memory and cognition, and the mechanisms of substance abuse. Inhibitors of MAO have been demonstrated to have effects on attention, cognition, appetite, substance abuse, memory, cardiovascular function, extrapyramidal function, pain and gastrointestinal motility and function. The distribution of MAO in the brain is widespread and includes the basal ganglia, cerebral cortex, limbic system, and mid and hind-brain nuclei. In the peripheral tissue, the distribution includes muscle, the gastrointestinal tract, the cardiovascular system, autonomic ganglia, the liver, and the endocrinic system.

MAO inhibition by other inhibitors have been shown to increase monoamine content in the brain and body. Regulation of monoamine levels in the body have been shown to be effective in numerous disease states including depression, anxiety, stress disorders, diseases associated with memory function, neuroendocrine problems, cardiac dysfunction, gastrointestinal disturbances, eating disorders, hypertension, Parkinson's disease, memory disturbances, and withdrawal symptoms.

It has been suggested that cigarette smoke may have irreversible inhibitory effect towards monoamine oxidase (MAO). Boulton et al., "Biogenic Amine Adducts, Monoamine Oxidase Inhibitors, and Smoking," Lancet, 1(8577): 114-155 (Jan. 16, 1988), reported that the MAO-inhibiting properties of cigarette smoke may help to explain the protective action of smoking against Parkinson's disease and also observed that patients with mental disorders who smoke heavily do not experience unusual rates of smoking-induced disorders. It was suggested that smoking, as an MAO inhibitor, may protect against dopaminergic neurotoxicity that leads to Parkinson's disease and that the MAO-inhibiting properties of smoking may result in an anti-depressive effect in mental patients.

SUMMARY OF THE INVENTION

Prior to the invention, MAO-A and MAO-B are the only two monoamine oxidases identified in human. While attempting to identify and characterize novel secretory proteins in human using human genomics database, the present inventors identified a new monoamine oxidase. The present invention discloses the identification and characterization of a secretory form of monoamine oxidase that metabolizes biogenic monoamines such as norepinephrine, dopamine and epinephrine. Since the newly identified monoamine oxidase is the third enzyme identified that metabolize monoamines in human, the present inventors designated it by the name 'MAO-C'. Alternatively, because it is a protein secreted by the kidney, it is also termed 'renalase.' Because MAO-C, or renalase, is a new member of the monoamine oxidase family, the enzyme is also expected to play an important role in the brain as do MAO-A and MAO-B.

The present invention relates a nucleic acid encoding a novel mammalian monoamine oxidase (MAO) termed renalase (SEQ ID NO: 2), a novel protein involved in regulating catecholamines. The nucleic acid sequence of human renalase is 27.7% homologous to that of human MAO-A (SEQ ID NO: 10) and 38.2% homologous to that of MAO-B (SEQ ID NO: 12). Renalase has 13% and 12% identity at the amino acid level to MAO-A and MAO-B, respectively. It also has a distinct substrate specificity and inhibitor profile to that of MAO-A and MAO-B, indicating that it represents a brand new class of unique FAD-containing monoamine oxidases.

The human renalase gene resides on chromosome 10, contains 9 exons and spans about 300 Kb. The human renalase gene encodes a 342-amino acid protein that contains an amino-terminal signal sequence, followed by a flavin-adenosine-dinucleotide (FAD)-containing domain and an amino oxidase domain. Tissue Northern blotting studies demonstrated robust expression of renalase in kidney with much lower levels in all other tissues analyzed. In situ hybridization demonstrated the high level of expression of renalase in proximal and distal tubules.

Renalase was highly expressed in in vitro transcription and translation experiments. Human renalase cDNA is translated to produce a protein with a molecular mass of approximately 38-kDa, which is in agreement with the predicted protein size. Western blotting studies using conditioned medium from transfected HEK293 cells indicates that renalase is a secreted protein. Renalase is present in the plasma at a concentration of 5-10 mg/l in healthy individual.

End-Stage Renal Disease (ESRD) is associated with elevated catecholamine levels, which in turn leads to a myriad of conditions, diseases and disorders, including, for example, asymptomatic left ventricular dysfunction, chronic congestive heart failure and atherosclerosis. These conditions, diseases and disorders are a common cause of death among ESRD patients.

Renalase metabolizes catecholamines in the following rank orders: dopamine>epinephrine>norepinephrine. Ranalase is virtually undetectable in patients with ESRD. Thus, the loss or reduced levels of renalase in ESRD patients is at least in part responsible for elevated plasma catecholamine levels, which leads to increased cardiovascular disease, which is a common cause of death among ESRD patients.

In addition, the correlation between renalase levels and renal function make renalase an ideal candidate for a diagnostic marker for renal disease, especially for acute tubular necrosis, a common occurrence in the Intensive Care Unit setting. The biological significance of renalase and its potential clinical relevance are further discussed herein.

The present invention provides a novel FAD-dependent amine oxidase that is secreted into the blood by the kidney. It metabolizes circulating catecholamines and inter alia is a potent regulator of blood pressure and heart rate. Furthermore, its reduced presence in the plasma of patients with ESRD suggests a causal link to the heightened sympathetic tone and increased cardiovascular risks that are well documented in this patient population. The identification of renalase is not only an important step in development of a more detailed understanding of cardiovascular physiology, but also an important step in the quest for providing optimal treatment for patients with kidney disease and/or heart disease and their related complications.

The invention includes an isolated nucleic acid molecule encoding a polypeptide, wherein the nucleic acid molecule shares at least about or greater than about 40% sequence identity with the nucleic acid sequence of SEQ ID NO: 1.

The invention includes an isolated nucleic acid molecule encoding a polypeptide, wherein the nucleic acid molecule shares at least about or greater than about 40% sequence identity with the nucleic acid sequence of nucleic acid residues 24 to 1049 of SEQ ID NO: 1.

In one aspect, the nucleic acid further comprises a nucleic acid encoding a tag polypeptide covalently linked thereto.

In another aspect, the nucleic acid further comprises a nucleic acid specifying a promoter/regulatory sequence operably linked thereto.

In yet another aspect, the invention includes a vector comprising an isolated nucleic acid encoding a polypeptide, wherein the nucleic acid shares at least about or greater than about 40% identity with SEQ ID NO: 1.

In a further aspect, the invention includes a recombinant cell comprising an isolated nucleic acid encoding a polypeptide, wherein the nucleic acid shares at least about or greater than about 40% identity with SEQ ID NO: 1.

The invention includes an isolated nucleic acid complementary to an isolated nucleic acid encoding a polypeptide, or a fragment thereof, the complementary nucleic acid being in an antisense orientation.

In one aspect, a nucleic acid of the present invention shares at least about or greater than about 40% identity with a nucleic acid complementary with a nucleic acid having the sequence of a human renalase (SEQ ID NO: 1).

The invention includes an isolated mammalian renalase peptide, polypeptide or protein.

The invention includes an isolated mammalian polypeptide, wherein the polypeptide comprises an amino acid sequence having at least about or greater than about 15% identity with a polypeptide having the amino acid sequence of SEQ ID NO: 2.

The invention also includes an isolated polypeptide, wherein the polypeptide comprises an amino acid sequence having at least about or greater than about 15% identity with a polypeptide having the amino acid sequence of amino acid residues 24 to 342 of SEQ ID NO: 2.

The invention includes an antibody that specifically binds with a mammalian renalase, or a fragment thereof. The antibody can be a polyclonal antibody, a monoclonal antibody, or a synthetic antibody.

The invention includes a composition comprising an isolated nucleic acid encoding a polypeptide, wherein the nucleic acid shares at least about or greater than about 40% identity with SEQ ID NO:1, and a pharmaceutically-acceptable carrier.

The invention includes a composition comprising an isolated mammalian renalase polypeptide and a pharmaceutically-acceptable carrier.

The invention includes a method of identifying a compound that reduces or inhibits expression of human renalase in a cell. The method comprises contacting a cell in which renalase is expressed with a compound and comparing the level of expression of human renalase in the cell contacted with the compound with the level of expression of human renalase in an otherwise identical cell, wherein a lower level of expression of human renalase in the cell contacted with the compound compared with the level of expression of human renalase in the otherwise identical cell not contacted with the compound, is an indication that the compound inhibits expression of human renalase in the cell. In one aspect, the invention includes a compound identified by this method, wherein such a compound is an antagonist of human renalase.

The invention also includes a method of identifying a compound that enhances or increases expression of human renalase in a cell. The method comprises contacting a cell in which renalase is expressed with a compound and comparing the level of expression of human renalase in the cell contacted with the compound with the level of expression of human renalase in an otherwise identical cell, wherein a higher level of expression of human renalase in the cell contacted with the compound compared with the level of expression of human renalase in the otherwise identical cell not contacted with the compound, is an indication that the compound enhances or increases expression of human renalase in the cell. In one aspect, the invention includes a compound identified by this method, wherein such a compound is an agonist of human renalase.

The invention includes a method of treating a condition, disorder or disease mediated by expression of a human renalase. The method comprises administering to a human patient afflicted with a condition, disorder or disease mediated by expression of a human renalase, a human renalase expression-inhibiting or human renalase expression-reducing amount of a renalase inhibitor, thereby treating a condition, disorder or disease mediated by expression of a human renalase.

The compositions and methods of the present invention may be used to treat any condition, disorder or disease associated with the vascular, cardiac, renal, neural and/or endocrine systems of an organism, including humans. In one aspect, the condition, disorder or disease is selected from the group consisting of ESRD, chronic kidney disease, hypertension, cardiovascular diseases such as asymptomatic left ventricular dysfunction, chronic congestive heart failure, cardiac rhythm disturbances, and atherosclerosis.

In yet another aspect, the renalase inhibitor comprises an isolated nucleic acid complementary to an isolated nucleic acid encoding a human renalase, or a fragment thereof, the complementary nucleic acid being in an antisense orientation.

The invention includes a method of treating hypertension in a mammal, comprising administering renalase, thereby treating hypertension in the mammal.

Also contemplated is a method of treatment of conditions, disorders or diseases of the central nervous system (CNS) including without limitation dementia, Alzheimer's disease, schizophrenia, psychosis, depression, headaches, migraine headache or a tension headache and epilepsy; and treatment and/or prevention of CNS disorders such as major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders and social phobia; dementia of Alzheimer's type, with early or late onset, disorders induced by alcohol, amphetamines, cocaine, hallucinogens, inhalants, opioids, phecyclidine, sedatives, hypnotics, anxiolytics and other substances.

The invention further includes a method of identifying a human patient afflicted with a disease, disorder or condition associated with altered expression of renalase. The method comprises detecting the level of renalase expression in a human and comparing the level of expression of renalase in the human with the level of expression of renalase in a normal human not afflicted with a disease, disorder or condition associated with altered expression of renalase, thereby detecting a human patient afflicted with a disease, disorder or condition associated with altered expression of renalase.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that invention is not limited to the precise arrangements and instrumentalities shown. In the drawings:

FIG. 1C is a deduced amino acid sequence of human renalase (amino acids 1-335 of SEQ ID NO:2) in comparison with MAO-A (amino acids 13-354 of SEQ ID NO:11).

FIG. 2A shows the cDNA and deduced amino acid sequence of human renalase (SEQ ID NO:2). Amino acids residues 1-16 enclosed by a box are believed to code for a signal peptide.

FIG. 2C is an alignment between human MAO-A (SEQ ID NO:11), MAO-B (SEQ ID NO:13), and MAO-C (SEQ ID NO:2).

FIG. 3A is an in situ hybridization analysis of human kidney; Left panel: antisense probe, magnification of 200×, open arrows label the glomerulus, closed arrows indicate proximal tubules; right panel: sense probe control magnification of 100×.

FIG. 3B is an in situ hybridization analysis of human heart; Left panel: antisense probe, magnification of 200×, open arrows label blood vessels, closed arrows indicate ventricular myocytes; right panel: sense probe control.

FIG. 3C is an image of immunolocalization in human kidney; Left panel: anti-renalase antibody, magnification of 630×, closed arrows indicate proximal tubules; right panel: preimmune serum.

FIG. 3D is an image of immunolocalization in human heart; Left panel: anti-renalase antibody, magnification of 630×, open arrows label blood vessels, closed arrows indicate ventricular myocytes; right panel: preimmune serum.

FIGS. 4A through 4C show the expression of a rat renalase-HA-tagged fusion protein in HEK293 cells.

FIG. 4A depicts the construction of expression TAP fragment of renalase.

FIG. 4B is an image depicting the generation and purification of GST-renalase fusion protein. The proteins (100 µg) from crude bacterial lysate and purified GST-renalase (10 µg) were separated on a 10% SDS-polyacrylamide gel, stained with Coomassie blue. Lane A: crude bacterial lysate; lane B: purified renalase protein.

FIG. 4C shows the determination of renalase activity. Purified GST-renalase fusion protein (10 µg for each reaction) was used for each assay. The amino oxidase activity is expressed in arbitrary fluorescence units/10 µg of protein after 30 min incubation with dopamine or norepinephrine (2 mM final concentration). Column 1: Control protein (GST) with dopamine and norepinephrine; Column 2: GST-renalase with norepinephrine; Column 3: GST-renalase with dopamine.

FIGS. 5A through 5B show that renalase is a secreted protein.

FIG. 5A is an image depicting the detection of renalase in culture medium of HEK293 cells transiently transfected with renalase cDNA.

FIG. 5B is an imaging depicting the Western blot analysis of human plasma using an anti-renalase antibody, normal refers to individuals with normal renal function, control is recombinant renalase, ESRD represents patients with end-stage renal disease receiving hemodialysis.

In FIG. 6A, 10 µg of GST-renalase fusion protein was used for each assay; amine oxidase activity is expressed in arbitrary fluorescence units/10 µg of protein; substrates (2 mM) are incubated for 30 min incubation.

In FIG. 6B, as in 6A; 1 µM chlorgyline and 1 µM pargyline was used.

FIG. 6C is an image of affinity purified human renalase. Protein was isolated from human urine using the anti-renalase antibody; lane 1: human urine, lane 2: control with secondary antibody alone.

FIG. 7A shows cardiac response before and after an IV bolus injection of 4 µg/g body weight; arrow denotes the timing of renalase injection; Vp=left ventricular pressure; HR=heart rate; dP/dt=rate of change in left ventricular pressure, a measure of cardiac contractility.

FIG. 7B is the pressure-volume curve before and after renalase injection.

FIG. 7C is an enlargement of a portion of FIG. 7A (see Arrow). HR: heart rate, Vp: left ventricular pressure.

FIG. 7D is the renalase dose-response curve on cardiac contractility.

FIG. 7E is the renalase dose-response curve on mean arterial pressure.

FIG. 7F is the time course of renalase activity on plasma epinephrine.

FIG. 7G is the time course of renalase activity on plasma norepinephrine.

DETAILED DESCRIPTION OF THE INVENTION

Figure 1A:
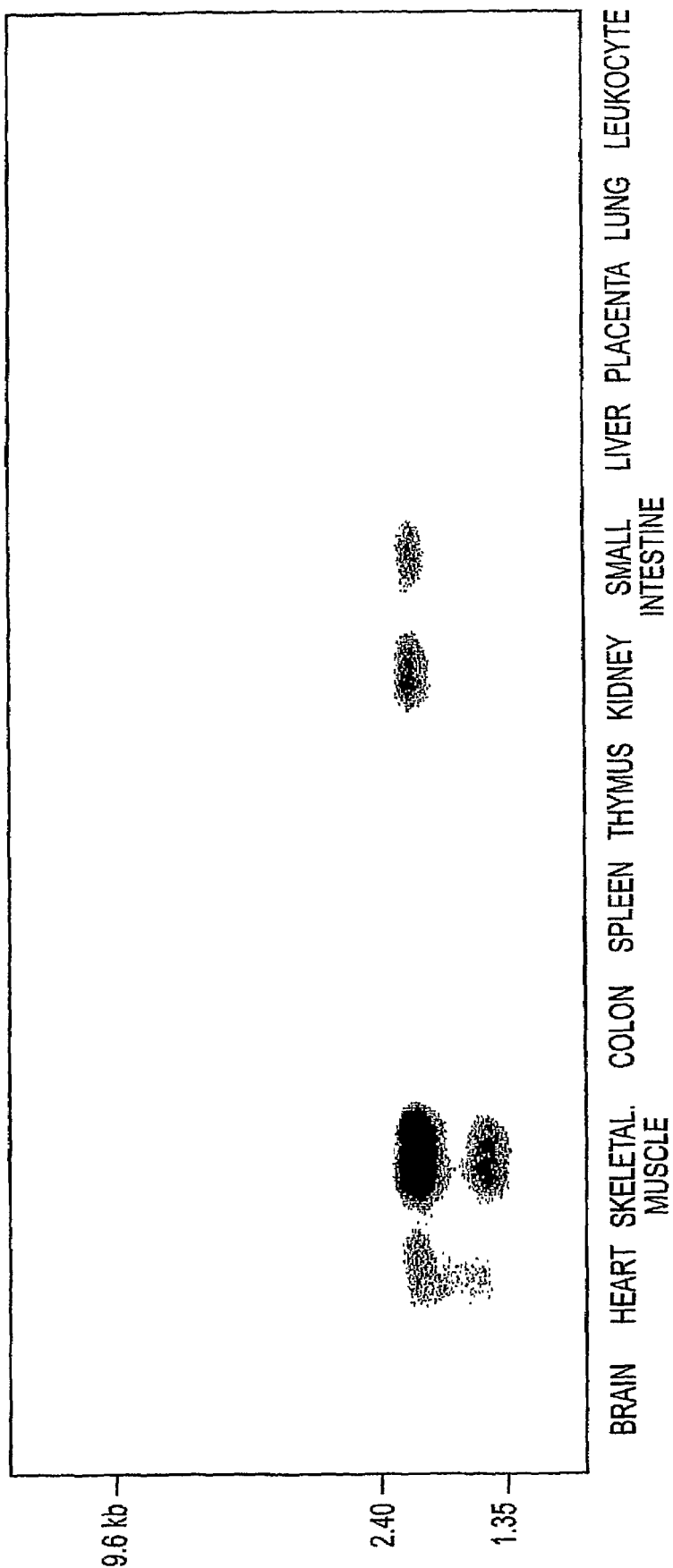
FIG. 1A is a Northern blot analysis of human tissue using the MGC12474 clone as a probe.

All publications and patent applications herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The data disclosed herein do not exclude receptor interaction and they demonstrate that renalase plays a role in, inter alia, degrading circulating catecholamines such as norepinephrine, dopamine, and epinephrine, which are important mediators for the function of the kidney, heart and blood vessels. As described more fully elsewhere herein, renalase therefore also plays a role in acting as a hormone in that it regulates the function of other tissues and/or organs. This may also include the nervous system, as its functions are also mediated in part by catecholamines. Thus, renalase can be provided, for example, to patients who do not produce sufficient amounts of renalase. Identification of renalase has important implications in the development of therapeutics and diagnostics for, among other things, end-stage renal diseases (ESRD) to treat/prevent hypertension, cardiovascular diseases such as asymptomatic left ventricular dysfunction, chronic congestive heart failure and atherosclerosis.

Similar to erythropoietin (EPO), a recombinant protein widely used to treat patients with anemia, renalase is a secreted protein and is expressed in the kidney. Another striking feature of renalase is that, like EPO, it is virtually non-detectable in patients with ESRD, whereas renalase is expressed in the blood of healthy individuals at concentration of about 5-10 mg/L.

The data disclosed herein demonstrate the existence of a novel enzyme that metabolizes catecholamines. In addition to expanding the paradigm of MAO, this new finding has significant clinical implications for, for example, ESRD patients. Strategies whereby renalase levels are replenished to counteract excessive levels of renalase substrates (i.e., catecholamines) are logical approaches to treating patients with ESRD. Furthermore, any other disease caused by excessive levels of catecholamines, regardless of the status of renal function, could be treated through the addition of either supplemental or replenishing amounts of renalase.

Alternatively, renalase can be used as a drug target in order to raise circulatory catecholamine levels in patients with decreased sympathetic tone, and thus improve the outcome of certain cardiovascular complications. Renalase may also allow for the design of drugs more specific for MAO-A or MAO-B, as current MAO inhibitors may unknowingly also target renalase, which may result in unfavorable side-effects.

The identification and characterization of renalase provides a framework for further study of renalase and its role in the pathophysiology of cardiovascular diseases such as chronic heart failure (CHF), myocardial infarction (MI), cardiac rhythm disturbances as these diseases may be precipitated by sudden emotional stress which increases sympathetic stimulation (Wittstein et al., (2005) Neurohumoral features of myocardial stunning due to sudden emotional stress, New England Journal of Medicine, 352, 539-548). Perhaps more importantly, like MAO-A and -B, renalase may provide a potentially useful target for modulating sympathetic activity in human.

In addition to its potential therapeutic role, renalase can be used as a diagnostic marker for acute renal failure (i.e. acute tubular necrosis, or ATN, an ischemic condition in the kidney). As described above, patients without a properly functioning kidney possess lower levels of renalase.

Also included in the invention are methods of diagnosing susceptibility to cardiovascular, heart, kidney and mental related conditions, disorders and diseases based on the measurement of gene expression and enzyme activity of renalase. For example, cardiovascular conditions, disorders and diseases such as hypertension, asymptomatic left ventricular dysfunction, chronic congestive heart failure, myocardial infarction, cardiac rhythm disturbance, and atherosclerosis; mental conditions, disorders and diseases such as depression and anxiety; and heart conditions, disorders and diseases, such as pulmonary hypertension, can all be diagnosed, evaluated and monitored by determining renalase gene expression levels, renalase protein levels, and/or renalase enzyme activity. For example, reduced expression of the renalase gene would be a diagnostic marker for a disorder associated with an increased sympathetic output.

The compositions and methods of the present invention can be used to treat, prevent, reduce or ameliorate hypertension, including systolic hypertension, isolated systolic hypertension and diabetic hypertension. Moreover, the same benefit is anticipated for the more rare hypertensive disorder, pulmonary hypertension. Pulmonary hypertension is a rare blood vessel disorder of the lung in which the pressure in the pulmonary artery (the blood vessel that leads from the heart to the lungs) rises above normal levels and may become life threatening. The similarity in development of elevated blood pressure in the pulmonary bed with the increase in systemic blood pressure in diabetic hypertension and in isolated systolic hypertension suggests similar mechanisms are involved.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the term "adjacent" is used to refer to nucleotide sequences which are directly attached to one another, having no intervening nucleotides. By way of example, the pentanucleotide 5'-AAAAA-3' is adjacent the trinucleotide 5'-TTT-3' when the two are connected thus: 5'-AAAAATTT-3' or 5'-TTTAAAAA-3', but not when the two are connected thus: 5'-AAAAACTTT-3'.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, to "alleviate" a disease, disorder or condition means reducing the severity of one or more symptoms of the disease, disorder or condition. This can include, but is not limited to, increasing the level of renalase expressed in a cell or tissue (e.g., smooth muscle cell, lung tissue, an artery), reducing or increasing the level of renalase in a patient, compared with the level of renalase in the patient prior to or in the absence of the method of treatment, and the like.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, a bronchoscope, a nebulizer, and the like, for administering the renalase nucleic acid, protein, and/or composition of the invention to a mammal.

"Biological sample," as that term is used herein, means a sample obtained from an animal that can be used to assess the level of expression of a renalase, the level of renalase protein present, or both. Such a sample includes, but is not limited to, a blood vessel (e.g., carotid artery, aorta, and the like) sample, a lung tissue sample, and a SMC sample.

By "complementary to a portion or all of the nucleic acid encoding renalase" is meant a sequence of nucleic acid which does not encode a renalase protein. Rather, the sequence which is being expressed in the cells is identical to the non-coding strand of the nucleic acid encoding a renalase protein and thus, does not encode renalase protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

The term "replication defective" as used herein relative to a viral gene therapy vector of the invention means the viral vector cannot independently further replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate.

As used herein, a "retroviral transfer vector" refers to an expression vector that comprises a nucleotide sequence that encodes a transgene and further comprises nucleotide sequences necessary for packaging of the vector. Preferably, the retroviral transfer vector also comprises the necessary sequences for expressing the transgene in cells.

As used herein, "packaging system" refers to a set of viral constructs comprising genes that encode viral proteins involved in packaging a recombinant virus. Typically, the constructs of the packaging system will ultimately be incorporated into a packaging cell.

As used herein, a "second generation" lentiviral vector system refers to a lentiviral packaging system that lacks functional accessory genes, such as one from which the accessory genes, vif, vpr, vpu and nef, have been deleted or inactivated. See, e.g., Zufferey et al., 1997, Nat. Biotechnol. 15:871-875.

As used herein, a "third generation" lentiviral vector system refers to a lentiviral packaging system that has the characteristics of a second generation vector system, and further lacks a functional tat gene, such as one from which the tat gene has been deleted or inactivated. Typically, the gene encoding rev is provided on a separate expression construct. See, e.g., Dull et al., 1998, J. Virol. 72(11):8463-8471.

As used herein, "pseudotyped" refers to the replacement of a native envelope protein with a heterologous or functionally modified envelope protein.

As used herein, "ex vivo administration" refers to a process where primary cells are taken from a subject, a vector is administered to the cells to produce transduced, infected or transfected recombinant cells and the recombinant cells are readministered to the same or a different subject.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid sequence or nucleic acid molecule refers to a segment or portion of a reference full length nucleic acid sequence or molecule, wherein the fragment is less than the full length of the reference nucleic acid sequence or molecule. An example of a fragment nucleic acid sequence or molecule is a segment or portion of the full length renalase cDNA sequence or molecule, respectively. Another example of a fragment nucleic acid sequence or molecule is a segment or portion of a full length genomic renalase DNA sequence or molecule, respectively. A fragment may be any length that is less than the full length of the natural or native cDNA or gene. Examples of fragments include nucleic acids of at least about 20 nucleotides in length, at least about 50 nucleotides, at least about 50 to about 100 nucleotides, at least about 100 to about 200 nucleotides, at least about 200 nucleotides to about 300 nucleotides, at least about 300 to about 350, at least about 350 nucleotides to about 500 nucleotides, at least about 500 to about 600, at least about 600 nucleotides to about 650 nucleotides, at least about 650 to about 800, or at least 800 to about 1000 nucleotides in length.

As used herein, the term "fragment" as applied to an amino acid sequence or amino acid molecule refers to a segment or portion of a reference full length amino acid sequence or molecule, wherein the fragment is less than the full length of the reference amino acid sequence or molecule. An example of a fragment amino acid sequence or molecule is a segment or portion of a polypeptide encoded by the full length renalase cDNA sequence or molecule, respectively. Another example of a fragment amino acid sequence or molecule is a segment or portion of a polypeptide encoded by a full length genomic renalase DNA sequence or molecule, respectively. A fragment may be any length of a polypeptide that is less than the full length polypeptide encoded by a natural or native cDNA or gene. Examples of fragments include amino acids of at least about 20 amino acids in length, or at least about 30 amino acids, or at least about 40, or at least about 50, or at least about 60, or at least about 70, or at least about 80, or at least about 90, or at least about 100, or at least about 110, or at least about 120, or at least about 130, or at least about 130, or at least about 140, or at least about 150, or at least about 160, or at least about 170, or at least about 180, or at least about 190, or at least about 200, or at least about 210, or at least about 220, or at least about 230, or at least about 240, or at least about 250, or at least about 260, or at least about 270, or at least about 280, or at least about 290, or at least about 300, or at least about 310, or at least about 320, or at least about 330, or at least about 340 amino acids in length.

A "genomic DNA" is a DNA strand which has a nucleotide sequence homologous with a gene. By way of example, both a fragment of a chromosome and a cDNA derived by reverse transcription of a mammalian mRNA are genomic DNAs.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity." In addition, when the terms "homology" or "identity" are used herein to refer to the nucleic acids and proteins, it should be construed to be applied to homology or identity at both the nucleic acid and the amino acid sequence levels. A first oligonucleotide anneals with a second oligonucleotide with "high stringency" or "under high stringency conditions" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, In: Molecular Cloning: A Laboratory Manual, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul et al. (1990, J. Mol. Biol. 215:403-410), and can be accessed, for example, at the BLAST site of the National Center for Biotechnology Information (NCBI) world wide web site at the National Library of Medicine (NLM) at the National Institutes of Health (NIH). BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used as available on the website of the National Center for Biotechnology Information of the National Library of Medicine at the National Institutes of Health.

The percent identity between two sequences can be determined using techniques similar to those described above, with or without allowing gaps. In calculating percent identity, typically exact matches are counted.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologs), which have a nucleotide sequence which differs from that of the mouse proteins described herein are within the scope of the invention. Nucleic acid molecules corresponding to natural allelic variants and homologs of a cDNA of the invention can be isolated based on their identity to mouse nucleic acid molecules using the mouse cDNAs, or a portion thereof, as a hybridization probe according to standard hybridization techniques under stringent hybridization conditions. For example, a homolog of a nucleic acid encoding a rat renalase protein of the invention can be isolated based on its hybridization with a nucleic acid molecule encoding all or part of rat and/or human renalase under high stringency conditions.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region. Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene." Two polypeptides do not necessarily need to be adjacent to each other in order to be operably linked.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence. A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides. The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

As used herein, the term "therapeutically effective amount" means the quantity of an agent that is effective in treating a condition, disorder or disease.

A "portion" of a polynucleotide means at least at least about twenty sequential nucleotide residues of the polynucleotide. It is understood that a portion of a polynucleotide may include every nucleotide residue of the polynucleotide. "Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

By "renalase inhibitor" is meant a compound that detectably inhibits the level of renalase in a cell or tissue when compared to the level of renalase in an otherwise identical cell or tissue in the absence of the compound. The level of renalase includes, but is not limited to, the level of expression of a nucleic acid encoding the molecule, the level of renalase detectable, and/or the level of renalase activity. Renalase inhibitors include, but are not limited to, a chemical compound, a cofactor, an antibody, a ribozyme, an antisense molecule, a nucleic acid, and the like.

"Recombinant polynucleotide" refers to a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides. Conventional notation is used herein to portray polypeptide sequences: the left-hand end of a polypeptide sequence is the amino-terminus; the right-hand end of a polypeptide sequence is the carboxyl-terminus.

As used herein, the term "renalase" refers to a novel monoamine oxidase secreted by the kidney that metabolizes biogenic monoamines such as dopamine, norepinephrine, and epinephrine. The renalase molecules disclosed herein are a class of molecules that include those having high and/or significant sequence identity with other polypeptides disclosed herein. More specifically, the putative renalase will share at least about 40% sequence identity with a nucleic acid having the sequence SEQ ID NO: 1. More preferably, a nucleic acid encoding renalase has at least about 45% identity, or at least about 50% identity, or at least about 55% identity, or at least about 60% identity, or at least about 65% identity, or at least about 70% identity, or at least about 75% identity, or at least about 80% identity, or at least about 85% identity, or at least about 90% identity, or at least about 95% identity, or at least about 98%, or at least about 99% sequence identity with SEQ ID NO: 1 disclosed herein. Even more preferably, the nucleic acid is SEQ ID NO:1.

The term "renalase" also includes renalase isoforms. The renalase gene contains 9 exons spanning 310188 bp in chromosome 10 of human genome. The renalase clone (SEQ ID NO: 1, GenBank accession number: BC005364) disclosed herein is the gene containing exons 1, 2, 3, 4, 5, 6, 8. There are at least two additional alternatively-spliced forms of renalase protein as shown in the human genome database. One alternatively spliced form contains exons 1, 2, 3, 4, 5, 6, 9, identified by clones in the human genome database as GenBank accession number AK002080 (SEQ ID NO: 3) and NM_018363 (SEQ ID NO: 4). The other alternatively spliced form contains exons 5, 6, 7, 8, identified by clones in the human genome database as GenBank accession number BX648154 (SEQ ID NO: 5).

Unless otherwise indicated, "renalase" encompasses all known renalases (e.g., rat renalase, and human renalase), and renalases to be discovered, including but not limited to, mouse renalase and chimpanzee renalase, having the characteristics and/or physical features of the renalase disclosed herein.

A "restriction site" is a portion of a double-stranded nucleic acid which is recognized by a restriction endonuclease. A portion of a double-stranded nucleic acid is "recognized" by a restriction endonuclease if the endonuclease is capable of cleaving both strands of the nucleic acid at the portion when the nucleic acid and the endonuclease are contacted.

By the term "specifically binds," as used herein, is meant a compound, e.g., a protein, a nucleic acid, an antibody, and the like, which recognizes and binds a specific molecule, but does not substantially recognize or bind other molecules in a sample.

A first oligonucleotide anneals with a second oligonucleotide "with high stringency" if the two oligonucleotides anneal under conditions whereby only oligonucleotides which are at least about 70%, or at least about 73%, more preferably, at least about 75%, even more preferably, at least about 80%, even more preferably, at least about 85%, yet more preferably, at least about 90%, and most preferably, at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

As used herein, the term "transgene" means an exogenous nucleic acid sequence which exogenous nucleic acid is encoded by a transgenic cell or mammal.

A "recombinant cell" is a cell that comprises a transgene. Such a cell may be a eukaryotic cell or a prokaryotic cell. Also, the transgenic cell encompasses, but is not limited to, an embryonic stem cell comprising the transgene, a cell obtained from a chimeric mammal derived from a transgenic ES cell where the cell comprises the transgene, a cell obtained from a transgenic mammal, or fetal or placental tissue thereof, and a prokaryotic cell comprising the transgene.

By the term "exogenous nucleic acid" is meant that the nucleic acid has been introduced into a cell or an animal using technology which has been developed for the purpose of facilitating the introduction of a nucleic acid into a cell or an animal. By "tag" polypeptide is meant any protein which, when linked by a peptide bond to a protein of interest, may be used to localize the protein, to purify it from a cell extract, to immobilize it for use in binding assays, or to otherwise study its biological properties and/or function.

As used herein, the term "transgenic mammal" means a mammal, the cells of which comprise an exogenous nucleic acid. The exogenous nucleic acid may or may not be integrated into the genome of the mammal.

As used herein, to "treat" means reducing the frequency, extent, severity and/or duration with which symptoms of ESRD, hypertension, cardiovascular diseases, mental disorders, and the like, are experienced by a patient.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the renalase protein or nucleic acid encoding a mammalian renalase, to the patient, or the vector may be a non-viral vector which is suitable for the same purpose.

Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

A "knock-out targeting vector," as the term is used herein, means a vector comprising two nucleic acid sequences each of which is complementary to a nucleic acid regions flanking a target sequence of interest which is to be deleted and/or replaced by another nucleic acid sequence. The two nucleic acid sequences therefore flank the target sequence which is to be removed by the process of homologous recombination.

As used herein, the term "chronic kidney disease" refers to kidney damage for 3 months as defined by structural or functional abnormalities with or without decreased glomerular filtration rate (GFR), or a GFR of 60 mL/min/1.73 m$^2$ or less, with or without kidney damage. GFR is a measure of the kidneys' ability to filter blood, which can be expressed on a continuous scale. GFR can be estimated by using the serum creatinine, the body weight, and age.

As used herein, the term "end stage renal disease (ESRD)" refers to a complete or near complete failure of the kidneys to function to excrete wastes, concentrate urine, and regulate electrolytes. End-stage renal disease (ESRD) occurs when chronic renal failure progresses to the point at which the kidneys are permanently functioning at less than 10% of their capacity. At this point, the kidney function is so low that without dialysis or kidney transplantation, complications are multiple and severe, and death will occur from accumulation of fluids and waste products in the body.

Description

I. Isolated Nucleic Acids

A. Sense Nucleic Acids

The present invention includes an isolated nucleic acid encoding a mammalian kidney expressed molecule, renalase, or a fragment thereof, wherein the nucleic acid shares at least about 40% identity with at least one nucleic acid having the sequence of (SEQ ID NO: 1). Alternatively, the nucleic acid is at least about 45% homologous, or at least about 50% homologous, or at least about 55% homologous, or at least about 60% homologous, or at least about 65% homologous, or at least about 70% homologous, or at least about 75% homologous, or at least about 80% homologous, or at least about 85% homologous, or at least about 90% homologous, or at least about 95% homologous, or at least about 98% homologous, or at least about 99% homologous to SEQ ID NO: 1 disclosed herein. In one embodiment, the nucleic acid sequence or molecule is provided by the sequence of SEQ ID NO: 1.

In another aspect, the present invention includes an isolated nucleic acid encoding a mammalian renalase, or a fragment thereof, wherein the protein encoded by the nucleic acid shares greater than about 15% homology with the amino acid sequence of SEQ ID NO: 2. Alignment studies reveal that renalase has 13.2% amino acid identity with monoamine oxidase A.

Preferably, the protein encoded by the isolated nucleic acid encoding renalase is at least about 15% homologous, or at least about 20% homologous, or at least about 25% homologous, or at least about 30% homologous, or at least about 35% homologous, or at least about 40% homologous, or at least about 45% homologous, or at least about 50% homologous, or at least about 55% homologous, or at least about 60% homologous, or at least about 65% homologous, or at least about 70% homologous, or at least about 75% homologous, or at least about 80% homologous, or at least about 85% homologous, or at least about 90% homologous, or at least about 95% homologous, or at least about 98%, or at least about 99% homologous to SEQ ID NO: 2. In one embodiment, the renalase polypeptide is encoded by the nucleic acid provide in SEQ ID NO:2. As disclosed herein, a nucleic acid of SEQ ID NO:1 can be translated to produce a human renalase protein comprising 342 amino acids with a calculated molecule mass of 37.8 kDa.

The present invention should not be construed as being limited solely to the nucleic and amino acid sequences disclosed herein. Once armed with the present invention, it is readily apparent to one skilled in the art that other nucleic acids encoding renalase polypeptides such as those present in other species of mammals (e.g., ape, gibbon, bovine, ovine, equine, porcine, canine, feline, murine, and the like), can be obtained by following the procedures described herein in the experimental details section for the isolation of the rat, and human renalase nucleic acids encoding renalase polypeptides as disclosed herein (e.g., screening of genomic or cDNA libraries), and procedures that are well-known in the art (e.g., reverse transcription PCR using mRNA samples) or to be developed.

Further, any number of procedures may be used for the generation of mutant, derivative or variant forms of renalase using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York).

Procedures for the introduction of amino acid changes in a protein or polypeptide by altering the DNA sequence encoding the polypeptide are well known in the art and are also described in Sambrook et al. (1989, supra); Ausubel et al. (1997, supra).

The invention further includes a nucleic acid encoding a mammalian renalase wherein a nucleic acid encoding a tag polypeptide is covalently linked thereto. That is, the invention encompasses a chimeric nucleic acid wherein the nucleic acid sequences encoding a tag polypeptide is covalently linked to the nucleic acid encoding at least one human renalase. Such tag polypeptides are well known in the art and include, for instance, green fluorescent protein (GFP), an influenza virus hemagglutinin tag polypeptide, myc, myc-pyruvate kinase (myc-PK), $His_6$, maltose biding protein (MBP), a FLAG tag polypeptide, a HA tag polypeptide, and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention. The nucleic acid comprising a nucleic acid encoding a tag polypeptide can be used to localize renalase within a cell, a tissue (e.g., a blood vessel, bone, and the like), and/or a whole organism (e.g., an amphibian and/or a mammalian embryo, and the like), detect renalase if secreted from a cell, and to study the role(s) of renalase in a cell. Further, addition of a tag polypeptide facilitates isolation and purification of the "tagged" protein such that the proteins of the invention can be produced and purified readily.

B. Antisense Nucleic Acids

In certain situations, it may be desirable to inhibit expression of renalase and the invention therefore includes compositions useful for inhibition of renalase expression. Thus, the invention features an isolated nucleic acid complementary to a portion or the entire length of a nucleic acid encoding a mammalian renalase, which nucleic acid is in an antisense orientation with respect to transcription. The antisense nucleic acid is complementary with a nucleic acid having at least about 40% homology with SEQ ID NO: 1, or a fragment thereof. In other embodiments, the antisense nucleic acid is at least about 45% homologous, or at least about 50% homologous, or at least about 55% homologous, or at least about 60% homologous, or at least about 65% homologous, or at least about 70% homologous, or at least about 75% homologous, or at least about 80% homologous, or at least about 85% homologous, or at least about 90% homologous, or at least about 95% homologous, or at least about 99% homologous to a nucleic acid complementary to a portion or the entire length of a nucleic acid encoding a mammalian renalase having the sequence of SEQ ID NO: 1, or a fragment thereof, which is in an antisense orientation with respect to transcription. Most preferably, the nucleic acid is complementary to a portion or the entire length of a nucleic acid that is SEQ ID NO: 1, or a fragment thereof. Such antisense nucleic acid serves to inhibit the expression, function, or both, of a kidney expressed (renalase) molecule.

Further, antisense nucleic acids complementary to all or a portion of a nucleic acid encoding renalase can be used to detect the expression of renalase mRNA in a cell, tissue, and/or organism, using, for example but not limited to, in situ hybridization. Thus, one skilled in the art would understand, based upon the disclosure provided herein, that the invention encompasses antisense nucleic acids that can be used as probes to assess renalase expression.

Antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

II. Isolated Polypeptides

A. Polypeptides, their Analogs and Modifications

The invention also includes an isolated polypeptide comprising a mammalian renalase. In one embodiment, the isolated polypeptide comprising a mammalian renalase is at least about 15% homologous to a polypeptide having the amino acid sequence of SEQ ID NO:2. In alternative embodiments, the isolated polypeptide comprising a mammalian renalase is at least about 20% homologous, or at least about 25% homologous, or at least about 30% homologous, or at least about 35% homologous, or at least about 40% homologous, or at least about 45% homologous, or at least about 50% homologous, or at least about 55% homologous, or at least about 60% homologous, or at least about 65% homologous, or at least about 70% homologous, or at least about 75% homologous, or at least about 80% homologous, or at least about 85% homologous, or at least about 90% homologous, or at least about 95% homologous, or at least about 98% homologous, or at least about 99% homologous to rat renalase. In one embodiment, the isolated polypeptide comprising a mammalian renalase is that of rat renalase. In another embodiment, the isolated polypeptide comprising a mammalian renalase molecule is SEQ ID NO:2.

The present invention also provides for analogs of proteins or peptides which comprise a renalase as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are renalase peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the renalase peptide of the present invention.

Further, the invention should be construed to include renalase isoforms, and naturally occurring variants or recombinantly derived mutants of renalase sequences, which variants or mutants render the protein encoded thereby either more, less, or just as biologically active as the full-length clones of the invention.

B. Production and Isolation of Polypeptides from Cells

As demonstrated elsewhere herein, the present invention also relates to methods for the production and isolation of renalase polypeptides from cells that produce renalase. The invention also contemplates methods for the production and isolation of renalase from the cellular media in which such cells are grown.

Cells that can be used in such methods include any cells that naturally produce renalase and cells that have been mutated, altered, or treated so as to produce renalase. Such cells include those that produce amounts of renalase typical for that type of cell and those cells that overproduce renalase. Cells that do not naturally produce renalase or produce renalase in low amounts may be mutated, altered or treated so that they produce renalase in amounts physically and/or economically practical for its isolation from such cells and the media in which they are grown.

Once produced by the cells, the renalase can be isolated from the cells and/or their growth media using protein isolation techniques well known to those skilled in the art of protein isolation. If desired or necessary, the isolated renalase may be further purified using purification techniques well known to those skilled in the art of protein purification.

C. Purification of Polypeptides from Bodily Fluids

The present invention also relates to a method for the purification of renalase polypeptides from bodily fluids of animals, particularly mammals. Any animal that produces renalase can be used for the purification of renalase from its bodily fluids. Examples of suitable animals include but are not limited to mice, rats, horses, pigs, dogs, monkeys, cows, and humans.

Purification of the polypeptides including fragments, homologous polypeptides, muteins, analogs, derivatives and fusion proteins is well-known and within the skill of one having ordinary skill in the art. See, e.g., Scopes, Protein Purification, 2d ed. (1987). Purification of chemically-synthesized peptides can readily be effected, e.g., by HPLC. Accordingly, the present invention provides a method of purifying a renalase polypeptide from at least one bodily fluid. The bodily fluids include, but are not limited to, blood, serum, plasma, saliva, urine, lymph fluid, whole blood, spinal fluid tissue culture medium, and cellular extracts. Purification of renalase from bodily fluids may be conducted by any protein purification known in the art, including but are not limited to, procedures of ion exchange chromatography, adsorption chromatography, ligand-bound affinity chromatography and gel permeation chromatography, solely or in combination.

It is an aspect of the present invention to provide the isolated proteins of the present invention in pure or substantially pure form in the presence or absence of a stabilizing agent. Stabilizing agents include both proteinaceous or non-proteinaceous material and are well-known in the art. Stabilizing agents, such as albumin and polyethylene glycol (PEG) are known and are commercially available.

Although high levels of purity are preferred when the isolated proteins of the present invention are used as therapeutic agents, such as in vaccines and as replacement therapy, the isolated proteins of the present invention are also useful at lower purity. For example, partially purified proteins of the present invention can be used as immunogens to raise antibodies in laboratory animals.

D. Activity of Polypeptides

The present invention further provides a pharmaceutical composition comprising a cofactor for enzyme activation. As more fully disclosed elsewhere herein, renalase is a flavin-adenosine-dinucleotide (FAD)-containing enzyme that requires the cofactor FAD for its functionality. Once armed with the present invention, it is readily apparent to one skilled in the art that other enzyme cofactors such as those which may function in a manner substantially similar to FAD and those well-known in the art can be employed to activate or deactivate renalase activity. These cofactors include, but are not limited to, FAD analogs, nicotinamide adenine dinucleotide (NAD), nicotinamide adenine dinucleotide phosphate (NADP), thiamine pyrophosphate, flavin adenine dinucleotide (FAD), flavin mononucleotide (FMN), pyridoxal phosphate, coenzyme A, tetrahydrofolate, adenosine triphosphate, guanosine triphosphate and S-adenosyl methionine (SAM), metal ion, metal porphyrin, e.g. heme groups, biotin, α2-microglobulin, thiamine pyrophosphate, coenzyme A, pyridoxal phosphate, coenzyme B12, biocytine, tetrahydrofolate, and lipoic acid.

Renalase activity may also be regulated by the formation of a homomultimer or a heteromultimer. A homomultimer may be a polypeptide consisting of three or more identical subunits. On the other hand, the multimeric polypeptide may be a heterodimer, i.e. a polypeptide consisting of two different subunits, or a heteromultimer consisting of three or more subunits wherein at least two of these subunits are different. For example, the multimeric polypeptide is comprised of a plurality of subunits which form a "single" multimeric polypeptide or a complex of a plurality of functionally associated polypeptides which may in turn be monomeric and/or multimeric polypeptides.

Figure 6C:
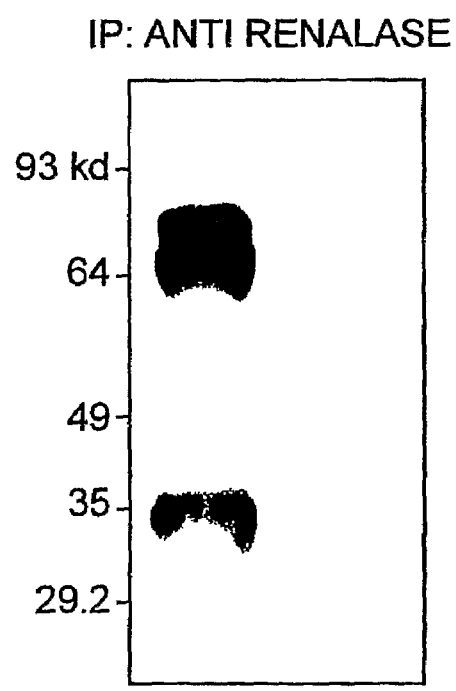
FIGS. 6A through 6C show enzymatic activity and function of renalase.

Homodimers or homomultimers may be formed by a spontaneous association of several identical polypeptide subunits. Heterodimers or heteromultimers may be formed by a spontaneous association of several different polypeptide subunits. There is evidence that renalase forms a dimer or multidimer complex (FIG. 6C). It is believed that dimerization or multimerization of renalase may positively or negatively affect the enzyme activity. Accordingly, it is expected that disruption or stabilization of the dimer or multimer complex of renalase may be particularly useful for various therapeutic purposes.

E. Uses of Polypeptides

The nucleic acids, and peptides encoded thereby, are useful tools for elucidating the function(s) of renalase molecules in a cell. Further, nucleic and amino acids comprising mammalian renalase molecules are useful targets that can be used, for example, to identify a compound that affects renalase expression, and the like, and is a potential therapeutic drug candidate for high blood pressure, kidney diseases, heart diseases and the like. The nucleic acids, the proteins encoded thereby, or both, can be administered to a mammal to increase or decrease expression or activity of renalase in the mammal. This can be beneficial for the mammal in situations where under or over-expression of renalase in the mammal mediates a disease or condition associated with altered expression of renalase compared with normal expression of renalase in a healthy mammal. Such conditions that can be affected by modulating renalase expression or activity thereby providing a therapeutic benefit include, but are not limited to, high blood pressure, kidney diseases, heart diseases and the like. This is because, as more fully disclosed elsewhere herein, infusion of renalase in rats has been shown to lower the blood pressure and heart rate.

Additionally, the nucleic and amino acids of the invention can be used to produce recombinant cells and transgenic non-human mammals which are useful tools for the study of renalase action, the identification of novel diagnostics and therapeutics for treatment, and for elucidating the cellular role(s) of renalase, among other things. For instance, transgenic animals can be used to study kidney and vascular disease related conditions.

Further, the nucleic and amino acids of the invention can be used diagnostically, either by assessing the level of gene expression or the level of protein expression, to assess severity and prognosis of ESRD, high blood pressure, heart diseases, kidney diseases, cardiovascular diseases, and the like. The nucleic acids, peptides, polypeptides and proteins of the invention are also useful in the development of assays to assess the efficacy of a treatment for preventing ESRD, high blood pressure, cardiovascular diseases, and the like. That is, the nucleic acids, peptides, polypeptides and proteins of the invention can be used to detect the effect of various therapies on renalase expression, thereby ascertaining the effectiveness of the therapies such as, but not limited to, assessment of treatment efficacies for ESRD, high blood pressure, heart diseases, kidney diseases, and cardiovascular diseases.

F. Small Molecule Inhibitors of the Polypeptides

In addition to antibodies, ribozymes, interfering RNA's (i.e., RNAi), and antisense nucleic acid molecules as disclosed herein, the present invention further provides methods of using small molecules to modulate renalase activity. As used herein, the term "potential small molecule inhibitor" refers to a small molecule which binds to a selected protein but for which the ability to inhibit a biological activity (e.g., reduce the catalytic rate of an enzyme) of the enzyme has not yet been tested. Following confirmation of such inhibitory characteristic, the small molecule can be referred to as a "small molecule inhibitor" or, more generally, an "inhibitor".

The term "small molecule" refers to a compound which has a molecular mass equal to or less than about 5000 Daltons (5 kD), or less than about 3 kD, or less than about 2 kD, or less than about 1 kD. In some cases it is preferred that a small molecule have a molecular mass equal to or less than about 700 Da.

As provided in the Examples, the proteins and nucleic acids of the invention, such as the protein having the amino acid sequence of SEQ ID NO. 2, are involved in catecholamine metabolism. Small molecules that modulate or down-regulate the expression of the protein or agents such as agonists or antagonists of at least one activity of the protein may be used to modulate biological and pathologic processes associated with the protein's function and activity.

Pathological processes refer to a category of biological processes which produce a deleterious effect. For example, lack of expression or down-regulation of expression of a protein of the invention may be associated with certain diseases such as ESRD. As used herein, a small molecule inhibitor is said to modulate a pathological process when the agent reduces the degree or severity of the process. For instance, a disease may be prevented or disease progression modulated by the administration of agents which reduce or modulate in some way the expression or at least one activity of a protein of the invention.

The small molecule inhibitor of the present invention can be provided alone, or in combination with other agents that modulate a particular pathological process. As used herein, two small molecules are said to be administered in combination when the two small molecules are administered simultaneously or are administered independently in a fashion such that the agents will act at the same time.

The small molecule inhibitors of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

III. Vectors

A. Vectors for In Vitro Expression

In other related aspects, the invention includes an isolated nucleic acid encoding a mammalian renalase operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, supra), and Ausubel et al. (1997, supra).

Expression of renalase, either alone or fused to a detectable tag polypeptide, in cells which either do not normally express the renalase or which do not express renalase fused with a tag polypeptide, may be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, both of which were used in the experiments disclosed herein, as well as the Rous sarcoma virus promoter, and the like. Moreover, inducible and tissue specific expression of the nucleic acid encoding renalase may be accomplished by placing the nucleic acid encoding renalase, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Expressing renalase using a vector allows the isolation of large amounts of recombinantly produced protein. Further, where the lack or decreased level of renalase expression causes a disease, disorder, or condition associated with such expression, the expression of renalase driven by a promoter/regulatory sequence can provide useful therapeutics including, but not limited to, gene therapy whereby renalase is provided. A disease, disorder or condition associated with a increased level of expression, level of protein, or decreased activity of the protein, for which administration of renalase can be useful therapeutics including, but not limited to, gene therapy whereby renalase is provided. Therefore, the invention includes not only methods of inhibiting renalase expression, translation, and/or activity, but it also includes methods relating to increasing renalase expression, protein level, and/or activity since both decreasing and increasing renalase expression and/or activity can be useful in providing effective therapeutics.

Selection of any particular plasmid vector or other DNA vector is not a limiting factor in this invention and a wide variety of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook, supra, and Ausubel, supra.

The invention thus includes a vector comprising an isolated nucleic acid encoding a mammalian renalase. The incorporation of a desired nucleic acid into a vector and the choice of vectors is well-known in the art as described in, for example, Sambrook et al., supra, and Ausubel et al., supra.

The invention also includes cells, viruses, proviruses, and the like, containing such vectors. Methods for producing cells comprising vectors and/or exogenous nucleic acids are well-known in the art. See, e.g., Sambrook et al., supra; Ausubel et al., supra.

The nucleic acids encoding renalase can be cloned into various plasmid vectors. However, the present invention should not be construed to be limited to plasmids or to any particular vector. Instead, the present invention should be construed to encompass a wide plethora of vectors which are readily available and/or well-known in the art and no vector at all.

B. Vectors for In Vivo and Ex Vivo Expression

The renalase polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

The present invention contemplates the use of any of a variety of vectors for introduction of constructs comprising the coding sequence for two or more polypeptides or proteins and a self processing cleavage sequence into cells such that protein expression results. Numerous examples of expression vectors are known in the art and may be of viral or non-viral origin. Non-viral gene delivery methods which may be employed in the practice of the invention, include but are not limited to plasmids, liposomes, nucleic acid/liposome complexes, cationic lipids and the like.

Viral vectors can efficiently transduce cells and introduce their own DNA into a host cell. In generating recombinant viral vectors, non-essential genes are replaced with a gene encoding a protein or polypeptide of interest. Exemplary vectors include but are not limited to viral and non-viral vectors, such a retroviral vector (including lentiviral vectors), adenoviral (Ad) vectors including replication competent, replication deficient and gutless forms thereof, adeno-associated virus (AAV) vectors, simian virus 40 (SV-40) vectors, bovine papilloma vectors, Epstein-Barr vectors, herpes vectors, vaccinia vectors, Moloney murine leukemia vectors, Harvey murine sarcoma virus vectors, murine mammary tumor virus vectors, Rous sarcoma virus vectors and nonviral plasmids.

The vector typically comprises an origin of replication and the vector may or may not in addition comprise a "marker" or "selectable marker" function by which the vector can be identified and selected. While any selectable marker can be used, selectable markers for use in recombinant vectors are generally known in the art and the choice of the proper selectable marker will depend on the host cell. Examples of selectable marker genes which encode proteins that confer resistance to antibiotics or other toxins include, but are not limited to ampicillin, methotrexate, tetracycline, neomycin (Southern et al., J., J Mol Appl Genet. 1982; 1(4):327-41 (1982)), mycophenolic acid (Mulligan et al., Science 209:1422-7 (1980)), puromycin, zeomycin, hygromycin (Sugden et al., Mol Cell Biol. 5(2):410-3 (1985)) and G418. As will be understood by those of skill in the art, expression vectors typically include an origin of replication, a promoter operably linked to the coding sequence or sequences to be expressed, as well as ribosome binding sites, RNA splice sites, a polyadenylation site, and transcriptional terminator sequences, as appropriate to the coding sequence(s) being expressed.

Reference to a vector or other DNA sequences as "recombinant" merely acknowledges the operable linkage of DNA sequences that are not typically operably linked as isolated from or found in nature. Regulatory (expression and/or control) sequences are operatively linked to a nucleic acid coding sequence when the expression and/or control sequences regulate the transcription and, as appropriate, translation of the nucleic acid sequence. Thus expression and/or control sequences can include promoters, enhancers, transcription terminators, a start codon (i.e., ATG) 5' to the coding sequence, splicing signals for introns and stop codons.

Adenovirus gene therapy vectors are known to exhibit strong transient expression, excellent titer, and the ability to transduce dividing and non-dividing cells in vivo (Hitt et al., Adv in Virus Res 55:479-505, 2000). The recombinant Ad vectors of the instant invention comprise: (1) a packaging site enabling the vector to be incorporated into replication-defective Ad virions; (2) the coding sequence for two or more proteins or polypeptide of interest, and (3) a sequence encoding a self-processing cleavage site alone or in combination with an additional proteolytic cleavage site. Other elements necessary or helpful for incorporation into infectious virions, include the 5' and 3' Ad ITRs, the E2 genes, portions of the E4 gene and optionally the E3 gene.

Replication-defective Ad virions encapsulating the recombinant Ad vectors of the instant invention are made by standard techniques known in the art using Ad packaging cells and packaging technology. Examples of these methods may be found, for example, in U.S. Pat. No. 5,872,005. The coding sequence for two or more polypeptides or proteins of interest is commonly inserted into adenovirus in the deleted E3 region of the virus genome. Preferred adenoviral vectors for use in practicing the invention do not express one or more wild-type Ad gene products, e.g., E1a, E1b, E2, E3, and E4. Preferred embodiments are virions that are typically used together with packaging cell lines that complement the functions of E1, E2A, E4 and optionally the E3 gene regions. See, e.g. U.S. Pat. Nos. 5,872,005, 5,994,106, 6,133,028 and 6,127,175. Thus, as used herein, "adenovirus" and "adenovirus particle" refer to the virus itself or derivatives thereof and cover all serotypes and subtypes and both naturally occurring and recombinant forms, except where indicated otherwise. Such adenoviruses may be wildtype or may be modified in various ways known in the art or as disclosed herein. Such modifications include modifications to the adenovirus genome that is packaged in the particle in order to make an infectious virus. Such modifications include deletions known in the art, such as deletions in one or more of the E1a, E1b, E2a, E2b, E3, or E4 coding regions. Exemplary packaging and producer cells are derived from 293, A549 or HeLa cells. Adenovirus vectors are purified and formulated using standard techniques known in the art.

Adeno-associated virus (AAV) is a helper-dependent human parvovirus that is able to infect cells latently by chromosomal integration. Because of its ability to integrate chromosomally and its nonpathogenic nature, AAV has significant potential as a human gene therapy vector. For use in practicing the present invention rAAV virions are produced using standard methodology, known to those of skill in the art and are constructed such that they include, as operatively linked components in the direction of transcription, control sequences including transcriptional initiation and termination sequences, and the coding sequence(s) of interest. More specifically, the recombinant AAV vectors of the instant invention comprise: (1) a packaging site enabling the vector to be incorporated into replication-defective AAV virions; (2) the coding sequence for two or more proteins or polypeptide of interest; (3) a sequence encoding a self-processing cleavage site alone or in combination with an additional proteolytic cleavage site. AAV vectors for use in practicing the invention are constructed such that they also include, as operatively linked components in the direction of transcription, control sequences including transcriptional initiation and termination sequences. These components are flanked on the 5' and 3' end by functional AAV ITR sequences. By "functional AAV ITR sequences" is meant that the ITR sequences function as intended for the rescue, replication and packaging of the AAV virion.

Recombinant AAV vectors are also characterized in that they are capable of directing the expression and production of selected recombinant proteins or polypeptides of interest in target cells. Thus, the recombinant vectors comprise at least all of the sequences of AAV essential for encapsidation and the physical structures for infection of the recombinant AAV (rAAV) virions. Hence, AAV ITRs for use in the vectors of the invention need not have a wild-type nucleotide sequence (e.g., as described in Kotin, Hum. Gene Ther., 5:793-801, 1994), and may be altered by the insertion, deletion or substitution of nucleotides or the AAV ITRs may be derived from any of several AAV serotypes. Generally, an AAV vector is a vector derived from an adeno-associated virus serotype, including without limitation, AAV-1, AAV-2, AAV-3, AAV4, AAV-5, AAV-6, AAV-7, AAV-8, etc. Preferred rAAV expression vectors have the wild type REP and CAP genes deleted in whole or part, but retain functional flanking ITR sequences.

Typically, an AAV expression vector is introduced into a producer cell, followed by introduction of an AAV helper construct, where the helper construct includes AAV coding regions capable of being expressed in the producer cell and which complement AAV helper functions absent in the AAV expression vector. As used herein, the term "AAV helper functions" refers to AAV coding regions capable of being expressed in the host cell to complement AAV viral functions missing from the rAAV vector. Typically, the AAV helper functions include the AAV rep coding region and the AAV cap coding region. The helper construct may be designed to down regulate the expression of the large Rep proteins (Rep78 and Rep68), typically by mutating the start codon following p5 from ATG to ACG, as described in U.S. Pat. No. 6,548,286.

Introduction of an AAV expression vector into a producer cell is typically followed by introduction of helper virus and/or additional vectors into the producer cell, wherein the helper virus and/or additional vectors provide accessory functions capable of supporting efficient rAAV virus production.

"Accessory functions" refer to functions that are required by AAV for replication, but are not provided by the AAV virion itself. Thus, these accessory functions and factors must be provided by the host cell, a virus (e.g., adenovirus, herpes simplex virus or vaccinia virus), or by an expression vector that is co-expressed in the same cell. Generally, the E1A and E1B, E2A, E4 and VA coding regions of adenovirus are used to supply the necessary accessory function required for AAV replication and packaging (Matsushita et al., Gene Therapy 5:938 [1998]).

The producer cells are then cultured to produce rAAV. These steps are carried out using standard methodology. Replication-defective AAV virions encapsulating the recombinant AAV vectors of the instant invention are made by standard techniques known in the art using AAV packaging cells and packaging technology. Examples of these methods may be found, for example, in U.S. Pat. Nos. 5,436,146; 5,753,500, 6,040,183, 6,093,570 and 6,548,286. Further compositions and methods for packaging are described in Wang et al. (US 2002/0168342) and include those techniques within the knowledge of those of skill in the art. Both AAV vectors and AAV helper constructs can be constructed to contain one or more optional selectable marker genes. Selectable marker genes which confer antibiotic resistance or sensitivity to an appropriate selective medium are generally known in the art.

The term "AAV virion" refers to a complete virus particle, such as a "wild-type" (wt) AAV virus particle (comprising a linear, single-stranded AAV nucleic acid genome associated with an AAV capsid protein coat). In contrast, a "recombinant AAV virion," and "rAAV virion" refers to an infectious viral particle containing a heterologous DNA sequence of interest, flanked on both sides by AAV ITRs.

In practicing the invention, host cells for producing rAAV virions include mammalian cells, insect cells, microorganisms and yeast. Host cells can also be packaging cells in which the AAV rep and cap genes are stably maintained in the host cell or producer cells in which the AAV vector genome is stably maintained and packaged. Exemplary packaging and producer cells are derived from 293, A549 or HeLa cells. AAV vectors are purified and formulated using standard techniques known in the art.

Retroviral vectors are also a common tool for gene delivery (Miller, Nature 357: 455-460, 1992). Retroviral vectors and more particularly lentiviral vectors may be used in practicing the present invention. Accordingly, the term "retrovirus" or "retroviral vector", as used herein is meant to include "lentivirus" and "lentiviral vectors" respectively. Retroviral vectors have been tested and found to be suitable delivery vehicles for the stable introduction of genes of interest into the genome of a broad range of target cells. The ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell-surface receptor as compared to the native envelope protein) may also find utility in practicing the present invention. The ability to direct the delivery of retroviral vectors encoding one or more target protein coding sequences to specific target cells is desirable in practice of the present invention.

The present invention provides retroviral vectors which include e.g., retroviral transfer vectors comprising one or more transgene sequences and retroviral packaging vectors comprising one or more packaging elements. In particular, the present invention provides pseudotyped retroviral vectors encoding a heterologous or functionally modified envelope protein for producing pseudotyped retrovirus.

The core sequence of the retroviral vectors of the present invention may be readily derived from a wide variety of retroviruses, including for example, B, C, and D type retroviruses as well as spumaviruses and lentiviruses (RNA Tumor Viruses, Second Edition, Cold Spring Harbor Laboratory, 1985). An example of a retrovirus suitable for use in the compositions and methods of the present invention includes, but is not limited to, a lentivirus. Other retroviruses suitable for use in the compositions and methods of the present invention include, but are not limited to, Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Preferred Murine Leukemia Viruses include 4070A and 1504A (Hartley and Rowe, J. Virol. 19:19-25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. Other lentiviruses include a sheep Visna/maedi virus, a feline immunodeficiency virus (FIV), a bovine lentivirus, simian immunodeficiency virus (SIV), an equine infectious anemia virus (EIAV), and a caprine arthritis-encephalitis virus (CAEV).

The various genera and strains of retroviruses suitable for use in the compositions and methods are well known in the art (see, e.g., Fields Virology, Third Edition, edited by B. N. Fields et al., Lippincott-Raven Publishers (1996), see e.g., Chapter 58, Retroviridae: The Viruses and Their Replication, Classification, pages 1768-1771.

The packaging systems of the present invention comprise at least two packaging vectors, a first packaging vector which comprises a first nucleotide sequence comprising a gag, a pol, or gag and pol genes and a second packaging vector which comprises a second nucleotide sequence comprising a heterologous or functionally modified envelope gene. In a preferred embodiment, the retroviral elements are derived from a lentivirus, such as HIV. Preferably, the vectors lack a functional tat gene and/or functional accessory genes (vif, vpr, vpu, vpx, nef). In a further preferred embodiment, the system further comprises a third packaging vector that comprises a nucleotide sequence comprising a rev gene. The packaging system can be provided in the form of a packaging cell that contains the first, second, and, optionally, third nucleotide sequences.

The invention is applicable to a variety of systems, and those skilled in the art will appreciate the common elements shared across differing groups of retroviruses. The description herein uses lentiviral systems as a representative example. However, all retroviruses share the features of enveloped virions with surface projections and containing one molecule of linear, positive-sense single stranded RNA, a genome consisting of a dimer, and the common proteins gag, pol and env.

Lentiviruses share several structural virion proteins in common, including the envelope glycoproteins SU (gp120) and TM (gp41), which are encoded by the env gene; CA (p24), MA (p17) and NC (p7-11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, e.g., by mutation or deletion.

First generation lentiviral vector packaging systems provide separate packaging constructs for gag/pol and env, and typically employ a heterologous or functionally modified envelope protein for safety reasons. In second generation lentiviral vector systems, the accessory genes, vif, vpr, vpu and nef, are deleted or inactivated. Third generation lentiviral vector systems are preferred for use in practicing the present invention and include those from which the tat gene has been deleted or otherwise inactivated (e.g., via mutation).

Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., a liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

Typically, the packaging vectors are included in a packaging cell, and are introduced into the cell via transfection, transduction or infection. Methods for transfection, transduction or infection are well known by those of skill in the art. A retroviral/lentiviral transfer vector of the present invention can be introduced into a packaging cell line, via transfection, transduction or infection, to generate a producer cell or cell line.

The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400-11406, which describe packaging cells. Further description of stable cell line production can be found in Dull et al., 1998, J. Virology 72(11):8463-8471; and in Zufferey et al., 1998, J. Virology 72(12):9873-9880.

Zufferey et al., 1997, Nature Biotechnology 15:871-875, teach a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

Preferred packaging vectors may contain additional changes to the packaging functions to enhance lentiviral protein expression and to enhance safety. For example, all of the HIV sequences upstream of gag can be removed. Also, sequences downstream of the envelope can be removed. Moreover, steps can be taken to modify the vector to enhance the splicing and translation of the RNA.

Optionally, a conditional packaging system is used, such as that described by Dull et al., J. Virology 72(11):8463-8471, 1998. Also preferred is the use of a self-inactivating vector (SIN), which improves the biosafety of the vector by deletion of the HIV-1 long terminal repeat (LTR) as described, for example, by Zufferey et al., 1998, J. Virology 72(12):9873-9880. Inducible vectors can also be used, such as through a tet-inducible LTR.

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995). A person of ordinary skill in the art would be familiar with well-known techniques for use of HSV as vectors.

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

Other viral vectors may be employed as constructs in the present invention. For example, vectors derived from viruses such as poxvirus may be employed. A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997). It is contemplated in the present invention, that VEE virus may be useful in targeting dendritic cells.

A polynucleotide may be housed within a viral vector that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Any vector for use in practicing the invention will include heterologous control sequences, such as a constitutive promoter, e.g., the cytomegalovirus (CMV) immediate early promoter, the RSV LTR, the MoMLV LTR, and the PGK promoter; tissue or cell type specific promoters including mTTR, TK, HBV, HAAT, regulatable or inducible promoters, enhancers, etc. Preferred promoters include the LSP promoter (III et al., Blood Coagul. Fibrinolysis 8S2:23-30, 1997), the EF1-alpha promoter (Kim et al., Gene 91(2):217-23, 1990) and Guo et al., Gene Ther. 3(9):802-10, 1996). Most preferred promoters include the elongation factor 1-alpha (EF1a) promoter, a phosphoglycerate kinase-1 (PGK) promoter, a cytomegalovirus immediate early gene (CMV) promoter, chimeric liver-specific promoters (LSPs), a cytomegalovirus enhancer/chicken beta-actin (CAG) promoter, a tetracycline responsive promoter (TRE), a transthyretin promoter (TTR), an simian virus 40 (SV40) promoter and a CK6 promoter. The sequences of these and numerous additional promoters are known in the art. The relevant sequences may be readily obtained from public databases and incorporated into vectors for use in practicing the present invention.

The present invention also contemplates the inclusion of a gene regulation system for the controlled expression of the coding sequence for two or more polypeptides or proteins of interest. Gene regulation systems are useful in the modulated expression of a particular gene or genes. In one exemplary approach, a gene regulation system or switch includes a chimeric transcription factor that has a ligand binding domain, a transcriptional activation domain and a DNA binding domain. The domains may be obtained from virtually any source and may be combined in any of a number of ways to obtain a novel protein. A regulatable gene system also includes a DNA response element which interacts with the chimeric transcription factor. This element is located adjacent to the gene to be regulated.

Exemplary gene regulation systems that may be employed in practicing the present invention include, the *Drosophila* ecdysone system (Yao et al., Proc. Nat. Acad. Sci., 93:3346 (1996)), the *Bombyx* ecdysone system (Suhr et al., Proc. Nat. Acad. Sci., 95:7999 (1998)), the Valentis GeneSwitch® synthetic progesterone receptor system which employs RU486 as the inducer (Osterwalder et al., Proc Natl Acad Sci 98(22): 12596-601 (2001)); the Tet™ & RevTet™ Systems (BD Biosciences Clontech), which employs small molecules, such as tetracycline (Tc) or analogues, e.g. doxycycline, to regulate (turn on or off) transcription of the target (Knott et al., Biotechniques 32(4):796, 798, 800 (2002)); ARIAD Regulation Technology which is based on the use of a small molecule to bring together two intracellular molecules, each of which is linked to either a transcriptional activator or a DNA binding protein. When these components come together, transcription of the gene of interest is activated. Ariad has two major systems: a system based on homodimerization and a system based on heterodimerization (Rivera et al., Nature Med, 2(9): 1028-1032 (1996); Ye et al., Science 283: 88-91 (2000)), either of which may be incorporated into the vectors of the present invention.

Preferred gene regulation systems for use in practicing the present invention are the ARIAD Regulation Technology and the Tet™ & RevTet™ Systems.

C. Non-viral Vectors

Several non-viral methods for the transfer of expression vectors into cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and liofectamine-DNA complex, cell sonication (Fechheimer et al., 1987), gene bombardment using high velocity microprojectiles (Yang et al., 1990), polycations (Bousssif et al., 1995) and receptor-mediated transfection (Wu and Wu, 1987; Wu and Wu, 1988). Some of these techniques may be successfully adapted for in vivo or ex vivo use. A person of ordinary skill in the art would be familiar with the techniques pertaining to use of nonviral vectors, and would understand that other types of nonviral vectors than those disclosed herein are contemplated by the present invention.

In a further embodiment of the invention, the expression cassette may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL). One of ordinary skill in the art would be familiar with techniques utilizing liposomes and lipid formulations.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use subcutaneous, intradermal, or intracranial injection to avoid the toxicity and stability problems associated with cationic lipids in the circulation. The interaction of liposomes and plasma proteins is responsible for the disparity between the efficiency of in vitro (Felgner et al., 1987) and in vivo gene transfer (Zhu et al., 1993; Solodin et al., 1995; Thierry et al., 1995; Tsukamoto et al., 1995; Aksentijevich et al., 1996).

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

D. Delivery of Nucleic Acid Constructs Including Protein or Polypeptide Coding Sequences to Cells The vector constructs that may be employed by the invention comprising nucleic acid sequences encoding heterologous proteins or polypeptides, and a self-processing cleavage site alone or in combination with a sequence encoding an additional proteolytic cleavage site may be introduced into cells in vitro, ex vivo or in vivo for expression of heterologous coding sequences by cells, e.g., somatic cells in vivo, or for the production of recombinant polypeptides by vector-transduced cells, in vitro or in vivo.

The vector constructs of the invention may be introduced into cells in vitro or ex vivo using standard methodology known in the art. Such techniques include transfection using calcium phosphate, microinjection into cultured cells (Capecchi, Cell 22:479-488 (1980)), electroporation (Shigekawa et al., BioTechn., 6:742-751 (1988)), liposome-mediated gene transfer (Mannino et al., BioTechn., 6:682-690 (1988)), lipid-mediated transduction (Felgner et al., Proc. Natl. Acad. Sci. USA 84:7413-7417 (1987)), and nucleic acid delivery using high-velocity microprojectiles (Klein et al., Nature 327:70-73 (1987)).

For in vitro or ex vivo expression, any cell effective to express a functional protein may be employed. Numerous examples of cells and cell lines used for protein expression are known in the art. For example, prokaryotic cells and insect cells may be used for expression. In addition, eukaryotic microorganisms, such as yeast may be used. The expression of recombinant proteins in prokaryotc, insect and yeast systems are generally known in the art and may be adapted for protein or polypeptide expression using the compositions and methods of the present invention.

Exemplary host cells useful for expression further include mammalian cells, such as fibroblast cells, cells from non-human mammals such as ovine, porcine, murine and bovine cells, insect cells and the like. Specific examples of mammalian cells include COS cells, VERO cells, HeLa cells, Chinese hamster ovary (CHO) cells, 293 cell, NSO cells, 3T3 fibroblast cells, W138 cells, BHK cells, HEPG2 cells, DUX cells and MDCK cells.

Host cells are cultured in conventional nutrient media, modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium (MEM), Sigma), RPMI 1640 (Sigma), and Dulbecco's Modified Eagle's Medium (DMEM, Sigma) are typically suitable for culturing host cells. A given medium is generally supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The appropriate culture conditions for a particular cell line, such as temperature, pH and the like, are generally known in the art, with suggested culture conditions for culture of numerous cell lines for example in the ATCC Catalogue available on line at "http://www.atcc.org/SearchCatalogs/AllCollections.cfm"

The vectors of the invention may be administered in vivo via various routes (e.g., intradermally, intravenously, intratumorally, into the brain, intraportally, intraperitoneally, intramuscularly, into the bladder etc.), to deliver multiple genes connected via a self processing cleavage sequence to express two or more proteins or polypeptides in animal models or human subjects. Dependent upon the route of administration, the therapeutic proteins elicit their effect locally (e.g., in brain or bladder) or systemically (other routes of administration). The use of tissue specific promoters 5' to the open reading frame(s) for a protein or polypeptide in the vectors of the invention may be used to effect tissue specific expression of the two or more proteins or polypeptides encoded by the vector.

Various methods that introduce a recombinant vector carrying a transgene into target cells in vitro, ex vivo or in vivo have been previously described and are well known in the art. The present invention provides for therapeutic methods, vaccines, and cancer therapies by transducing target cells with recombinant vectors of the invention.

For example, in vivo delivery of the recombinant vectors of the invention may be targeted to a wide variety of organ types including, but not limited to brain, liver, blood vessels, muscle, heart, lung and skin.

In the case of ex vivo gene transfer, the target cells are removed from the host and genetically modified in the laboratory using recombinant vectors of the present invention and methods well known in the art.

The recombinant vectors of the invention can be administered using conventional modes of administration including but not limited to the modes described above. The recombinant vectors of the invention may be provided in any of a variety of formulations such as liquid solutions and suspensions, microvesicles, liposomes and injectable or infusible solutions. The preferred form depends upon the mode of administration and the therapeutic application. A from appropriate to the route of delivery may be readily determined using knowledge generally available to those of skill in the relevant art.

The many advantages to be realized in using the inventive recombinant vector constructs of the invention in recombinant protein and polypeptide production in vivo include administration of a single vector for long-term and sustained expression of two or more recombinant protein or polypeptide ORFs in patients; in vivo expression of two or more recombinant protein or polypeptide ORFs having biological activity; and the natural posttranslational modifications of the recombinant protein or polypeptide generated in human cells.

One preferred aspect is use of the recombinant vector constructs of the present invention for the in vitro production of recombinant proteins and polypeptides. Methods for recombinant protein production are well known in the art and self processing cleavage site-containing vector constructs of the present invention may be utilized for expression of recombinant proteins and polypeptides using such standard methodology.

In one exemplary aspect of the invention, vector introduction or administration to a cell (transfection) is followed by one or more of the following steps:

(1) culturing the transfected cell under conditions to selecting for a cell expressing the recombinant protein or polypeptide;

(2) evaluating expression of the recombinant protein or polypeptide; and (3) collecting the recombinant protein or polypeptide.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980-990 (1989), or any other promoter (e.g., cellular promoters such as eukaryotic cellular promoters including, but not limited to, the histone, pol III, and beta.-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Ψ-2, Ψ-AM, PA12, T19-14X, VT-19-17-H2, ΨCRE, . ΨCRIP, GP+E-86, GP+envAm12, and DAN cell lines as described in Miller, Human Gene Therapy, Vol. 1, pgs. 5-14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

IV. Host Cells Containing an Exogenously Supplied Coding Nucleic Acid Molecule

The present invention further provides host cells transformed with a nucleic acid molecule that encodes an renalase protein. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line, and other immortalized cell lines. Preferred eukaryotic host cells include Chinese hamster ovary (CHO) cells available from the ATCC as CCL61, NIH Swiss mouse embryo cells NIH/3T3 available from the ATCC as CRL 1658, baby hamster kidney cells (BHK), and the like eukaryotic tissue culture cell lines, and other immortalized cell line.

Any prokaryotic host can be used to express a rDNA molecule encoding a protein of the invention. The preferred prokaryotic host is E. coli.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al., Proc. Natl. Acad. Sci. USA 69:2110, 1972; and Maniatis et al., *Molecular Cloning, A Laboratory Mammal*, Cold Spring Harbor Laboratory, Cold Spring Harbor, N.Y. (1982). With regard to transformation of vertebrate cells with vectors containing rDNAs, electroporation, cationic lipid or salt treatment methods are typically employed, see, for example, Graham et al., Virol. 52:456, 1973; Wigler et al., *Proc. Natl. Acad. Sci. USA* 76:1373-76, 1979.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, *J. Mol. Biol.* 98:503, 1975, or Berent et al., *Biotech.* 3:208, 1985 or the proteins produced from the cell assayed via an immunological method.

V. Antisense Molecules, Ribozymes, and Interfering RNA

Further, the invention includes a recombinant cell comprising an antisense nucleic acid which cell is a useful model for elucidating the role(s) of renalase in cellular processes. That is, the increased expression of renalase in balloon-injured vessels and, more specifically, in the adventitia thereof, indicate that renalase is involved in cell proliferation associated with negative remodeling and arterial restenosis. Accordingly, a transgenic cell comprising an antisense nucleic acid complementary to renalase but in an antisense orientation is a useful tool for the study of the mechanism(s) of action of renalase and its role(s) in the cell and for the identification of therapeutics that ameliorate the effect(s) of renalase expression.

One skilled in the art can appreciate, based upon the disclosure provided herein, that an antisense nucleic acid complementary to a nucleic acid encoding renalase can be used to transfect a cell and the cell can be studied to determine the effect(s) of altered expression of renalase in order to study the function(s) of renalase and to identity useful therapeutics and diagnostics.

Further, methods of decreasing renalase expression and/or activity in a cell can provide useful diagnostics and/or therapeutics for diseases, disorders or conditions mediated by or associated with increased renalase expression, increased level of renalase protein in a cell or secretion therefrom, and/or increased renalase activity.

One skilled in the art will appreciate that one way to decrease the levels of renalase mRNA and/or protein in a cell is to inhibit expression of the nucleic acid encoding the protein. Expression of renalase may be inhibited using, for example, antisense molecules, and also by using ribozymes or double-stranded RNA as described in, for example, Wianny and Kemicka-Goetz (2000, Nature Cell Biol. 2:70-75).

RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., Nature (1998) 391(19):306-311; Timmons et al., Nature (1998) 395:854; Montgomery et al., TIG (1998) 14(7):255-258; David R. Engelke, Ed., RNA Interference (RNAi) Nuts & Bolts of RNAi Technology, DNA Press (2003); and Gregory J. Hannon, Ed., RNAi A Guide to Gene Silencing, Cold Spring Harbor Laboratory Press (2003). Therefore, the present invention also includes methods of silencing the gene encoding renalase by using RNAi technology.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262: 40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue (1993, U.S. Pat. No. 5,190,931).

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see Cohen, supra; Tullis, 1991, U.S. Pat. No. 5,023,243, incorporated by reference herein in its entirety).

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053, incorporated by reference herein in its entirety). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is that, because they are sequence-specific, only mRNAs with particular sequences are inactivated.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of renalase can be designed by incorporating target sequences into the basic ribozyme structure which are complementary to the mRNA sequence of the renalase encoded by renalase or having at least about 33% homology to SEQ ID NO:1. Preferably, the sequence is at least about 35% homologous, even more preferably, at least about 40% homologous, even more preferably, at least about 45% homologous, yet more preferably, at least about 50% homologous, more preferably, at least about 55% homologous, more preferably, at least about 60% homologous, even more preferably, at least about 65% homologous, yet more preferably, at least about 70% homologous, more preferably, at least about 75% homologous, even more preferably, at least about 80% homologous, yet more preferably, at least about 85% homologous, more preferably, at least about 90% homologous, even more preferably, at least about 95% homologous, and most preferably, at least about 99% homologous to SEQ ID NO: 1. Ribozymes targeting renalase may be synthesized using commercially available reagents (Applied Biosystems, Inc., Foster City, Calif.) or they may be genetically expressed from DNA encoding them.

V. Recombinant Cells and Transgenic Non-human Mammals

The invention includes a recombinant cell comprising, inter alia, an isolated nucleic acid encoding renalase, an antisense nucleic acid complementary thereto, a nucleic acid encoding an antibody that specifically binds renalase, and the like. In one aspect, the recombinant cell can be transiently transfected with a vector (e.g., a plasmid, and the like) encoding a portion of the nucleic acid encoding renalase. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, fibroblasts, mouse stem cells, amphibian oocytes, osteoblasts, smooth muscle cells, endothelial cells, and the like.

In one aspect, the recombinant cell comprising an isolated nucleic acid encoding mammalian renalase is used to produce a transgenic non-human mammal. That is, the exogenous nucleic acid, or "transgene" as it is also referred to herein, of the invention is introduced into a cell, and the cell is then used to generate the non-human transgenic mammal. The cell into which the transgene is introduced is preferably an embryonic stem (ES) cell. However, the invention should not be construed to be limited solely to ES cells comprising the transgene of the invention nor to cells used to produce transgenic animals. Rather, a transgenic cell of the invention includes, but is not limited to, any cell derived from a transgenic animal comprising a transgene, a cell comprising the transgene derived from a chimeric animal derived from the transgenic ES cell, and any other comprising the transgene which may or may not be used to generate a non-human transgenic mammal.

Further, it is important to note that the purpose of transgene-comprising, i.e., recombinant, cells should not be construed to be limited to the generation of transgenic mammals. Rather, the invention should be construed to include any cell type into which a nucleic acid encoding a mammalian renalase is introduced, including, without limitation, a prokaryotic cell and a eukaryotic cell comprising an isolated nucleic acid encoding mammalian renalase.

When the cell is a eukaryotic cell, the cell may be any eukaryotic cell which, when the transgene of the invention is introduced therein, and the protein encoded by the desired gene is no longer expressed therefrom, a benefit is obtained. Such a benefit may include the fact that there has been provided a system in which lack of expression of the desired gene can be studied in vitro in the laboratory or in a mammal in which the cell resides, a system wherein cells comprising the introduced gene deletion can be used as research, diagnostic and therapeutic tools, and a system wherein animal models are generated which are useful for the development of new diagnostic and therapeutic tools for selected disease states in a mammal including, for example, ESRD and hypertension.

Alternatively, the invention includes a eukaryotic cell which, when the transgene of the invention is introduced therein, and the protein encoded by the desired gene is expressed therefrom where it was not previously present or expressed in the cell or where it is now expressed at a level or under circumstances different than that before the transgene was introduced, a benefit is obtained. Such a benefit may include the fact that there has been provided a system in the expression of the desired gene can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal.

Such cell expressing an isolated nucleic acid encoding renalase can be used to provide renalase to a cell, tissue, or whole animal where a higher level of renalase can be useful to treat or alleviate a disease, disorder or condition associated with low level of renalase expression and/or activity. Such diseases, disorders or conditions can include, but are not limited to, ESRD, hypertension, cardiovascular diseases. Additional expression of renalase could thus lead to lower blood pressure. Therefore, the invention includes a cell expressing renalase to increase or induce renalase expression, translation, and/or activity, where increasing renalase expression, protein level, and/or activity can be useful to treat or alleviate a disease, disorder or condition.

One of ordinary skill would appreciate, based upon the disclosure provided herein, that a "knock-in" or "knock-out" vector of the invention comprises at least two sequences homologous to two portions of the nucleic acid which is to be replaced or deleted, respectively. The two sequences are homologous with sequences that flank the gene; that is, one sequence is homologous with a region at or near the 5' portion of the coding sequence of the nucleic acid encoding renalase and the other sequence is further downstream from the first. One skilled in the art would appreciate, based upon the disclosure provided herein, that the present invention is not limited to any specific flanking nucleic acid sequences. Instead, the targeting vector may comprise two sequences which remove some or all (i.e., a "knock-out" vector) or which insert (i.e., a "knock-in" vector) a nucleic acid encoding renalase, or a fragment thereof, from or into a mammalian genome, respectively. The crucial feature of the targeting vector is that it comprise sufficient portions of two sequences located towards opposite, i.e., 5' and 3', ends of the renalase open reading frame (ORF) in the case of a "knock-out" vector, to allow deletion/insertion by homologous recombination to occur such that all or a portion of the nucleic acid encoding renalase is deleted from or inserted into a location on a mammalian chromosome.

The design of transgenes and knock-in and knock-out targeting vectors is well-known in the art and is described in standard treatises such as Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the renalase coding region to be used in the targeting vector may be easily selected based upon known methods and following the teachings disclosed herein based on the disclosure provided herein including the nucleic and amino acid sequences of both rat and human renalase. Armed with these sequences, one of ordinary skill in the art would be able to construct the transgenes and knock-out vectors of the invention.

The invention further includes a knock-out targeting vector comprising a nucleic acid encoding a selectable marker such as, for example, a nucleic acid encoding the $neo^R$ gene thereby allowing the selection of transgenic a cell where the nucleic acid encoding renalase, or a portion thereof, has been deleted and replaced with the neomycin resistance gene by the cell's ability to grow in the presence of G418. However, the present invention should not be construed to be limited to neomycin resistance as a selectable marker. Rather, other selectable markers well-known in the art may be used in the knock-out targeting vector to allow selection of recombinant cells where the renalase gene has been deleted and/or inactivated and replaced by the nucleic acid encoding the selectable marker of choice. Methods of selecting and incorporating a selectable marker into a vector are well-known in the art and are describe in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

As noted herein, the invention includes a non-human transgenic mammal comprising an exogenous nucleic acid inserted into a desired site in the genome thereof thereby deleting the coding region of a desired endogenous target gene, i.e., a knock-out transgenic mammal. Further, the invention includes a transgenic non-human mammal wherein an exogenous nucleic acid encoding renalase is inserted into a site the genome, i.e., a "knock-in" transgenic mammal. The knock-in transgene inserted may comprise various nucleic acids encoding, for example, a tag polypeptide, a promoter/regulatory region operably linked to the nucleic acid encoding renalase not normally present in the cell or not typically operably linked to renalase.

The generation of the non-human transgenic mammal of the invention is preferably accomplished using the method which is now described. However, the invention should in no way be construed as being limited solely to the use of this method, in that, other methods can be used to generate the desired knock-out mammal. In the preferred method of generating a non-human transgenic mammal, ES cells are generated comprising the transgene of the invention and the cells are then used to generate the knock-out animal essentially as described in Nagy and Rossant (1993, In: Gene Targeting, A Practical Approach, pp. 146-179, Joyner ed., IRL Press). ES cells behave as normal embryonic cells if they are returned to the embryonic environment by injection into a host blastocyst or aggregate with blastomere stage embryos. When so returned, the cells have the full potential to develop along all lineages of the embryo. Thus, it is possible, to obtain ES cells, introduce a desired DNA therein, and then return the cell to the embryonic environment for development into mature mammalian cells, wherein the desired DNA may be expressed.

Precise protocols for the generation of transgenic mice are disclosed in Nagy and Rossant (1993, In: Gene Targeting, A Practical Approach, Joyner ed. IRL Press, pp. 146-179). and are therefore not repeated herein. Transfection or transduction of ES cells in order to introduce the desired DNA therein is accomplished using standard protocols, such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York). Preferably, the desired DNA contained within the transgene of the invention is electroporated into ES cells, and the cells are propagated as described in Soriano et al. (1991, Cell 64:693-702).

Introduction of an isolated nucleic acid into the fertilized egg of the mammal is accomplished by any number of standard techniques in transgenic technology (Hogan et al., 1986, Manipulating the Mouse Embryo: A Laboratory Manual, Cold Spring Harbor, NY). Most commonly, the nucleic acid is introduced into the embryo by way of microinjection.

Once the nucleic acid is introduced into the egg, the egg is incubated for a short period of time and is then transferred into a pseudopregnant mammal of the same species from which the egg was obtained as described, for example, in Hogan et al. (1986, Manipulating the Mouse Embryo: A Laboratory Manual, Cold Spring Harbor, N.Y.). Typically, many eggs are injected per experiment, and approximately two-thirds of the eggs survive the procedure. About twenty viable eggs are then transferred into pseudopregnant animals, and usually four to ten of the viable eggs so transferred will develop into live pups.

Any mammalian renalase gene may be used in the methods described herein to produce a transgenic mammal or a transgenic cell harboring a transgene comprising a deletion of all or part of that mammalian renalase gene.

The transgenic mammal of the invention can be any species of mammal. Thus, the invention should be construed to include generation of transgenic mammals encoding the chimeric nucleic acid, which mammals include mice, hamsters, rats, rabbits, pigs, sheep and cattle. The methods described herein for generation of transgenic mice can be analogously applied using any mammalian species. Preferably, the transgenic mammal of the invention is a rodent and even more preferably, the transgenic mammal of the invention is a mouse. By way of example, Lukkarinen et al. (1997, Stroke 28:639-645), teaches that gene constructs which enable the generation of transgenic mice also enable the generation of other transgenic rodents, including rats. Similarly, nullizygous mutations in a genetic locus of an animal of one species can be replicated in an animal of another species having a genetic locus highly homologous to the first species.

To identify the transgenic mammals of the invention, pups are examined for the presence of the isolated nucleic acid using standard technology such as Southern blot hybridization, PCR, and/or RT-PCR. Expression of the nucleic acid in the cells and in the tissues of the mammal is also assessed using ordinary technology described herein. Further, the presence or absence of renalase in the circulating blood of the transgenic animal can be determined, if the protein is secreted, by using, for example, Western blot analysis, or using standard methods for protein detection that are well-known in the art.

Cells obtained from the transgenic mammal of the invention, which are also considered "transgenic cells" as the term is used herein, encompass such as cells as those obtained from the renalase (+/−) and (−/−) transgenic non-human mammal described elsewhere herein, are useful systems for modeling diseases and symptoms of mammals which are believed to be associated with altered levels of renalase expression such as ESRD, hypertension, cardiovascular diseases. and any other disease, disorder or condition associated with an altered level of renalase expression.

Particularly suitable are cells derived from a tissue of the non-human knock-out or knock-in transgenic mammal described herein, wherein the transgene comprising the renalase gene is expressed or inhibits expression of renalase in various tissues. By way of example, cell types from which such cells are derived include fibroblasts and like cells of (1) the renalase (+/+), (+/−) and (−/−) non-human transgenic liveborn mammal, (2) the renalase (+/+), (−/−) or (+/−) fetal animal, and (3) placental cell lines obtained from the renalase (+/+), (−/−) and (+/−) fetus and liveborn mammal.

One skilled in the art would appreciate, based upon this disclosure, that cells comprising decreased levels of renalase protein, decreased level of renalase activity, or both, include, but are not limited to, cells expressing inhibitors of renalase expression (e.g., antisense or ribozyme molecules).

Methods and compositions useful for maintaining mammalian cells in culture are well known in the art, wherein the mammalian cells are obtained from a mammal including, but not limited to, cells obtained from a mouse such as the transgenic mouse described herein.

Alternatively, recombinant cells expressing renalase can be administered in ex vivo and in vivo therapies where administering the recombinant cells thereby administers the protein to a cell, a tissue, and/or an animal. Additionally, the recombinant cells are useful for the discovery of renalase ligand(s) and renalase signaling pathway(s).

The recombinant cell of the invention may be used to study the effects of elevated or decreased renalase levels on cell homeostasis and cell proliferation and/or migration since renalase has been hypothesized to play a role in cell migration, adventitial fibrosis, arterial restenosis, negative remodeling, and the like The recombinant cell of the invention, wherein the cell has been engineered such that it does not express renalase, or expresses reduced or altered renalase lacking biological activity, can also be used in ex vivo and in vivo cell therapies where either an animal's own cells (e.g., fibroblasts, and the like), or those of a syngeneic matched donor, are recombinantly engineered as described elsewhere herein (e.g., by insertion of an antisense nucleic acid or a knock-out vector such that renalase expression and/or protein levels are thereby reduced in the recombinant cell), and the recombinant cell is administered to the recipient animal. In this way, recombinant cells that express renalase at a reduced level can be administered to an animal whose own cells express increased levels of renalase thereby treating or alleviating a disease, disorder or condition associated with or mediated by increased renalase expression as disclosed elsewhere herein.

The transgenic mammal of the invention, rendered susceptible to adventitial fibrosis, arterial restenosis, and the like, such as, for example, a renalase knock-out mouse, can be used to study the pathogenesis of these diseases and the potential role of renalase therein.

Further, the transgenic mammal and/or cell of the invention may be used to further study the subcellular localization of renalase. Also, the transgenic mammal (both +/– and –/– live born and fetuses) and/or cell of the invention may be used to study to role(s) of renalase in catecholamine circulation to elucidate the target(s) of renalase action as well as any receptor(s) and/or ligands that bind with renalase to mediate its effect(s) in the cell.

VI. Antibodies

The invention also includes an antibody that specifically binds renalase, or a fragment thereof. One skilled in the art would understand, based upon the disclosure provided herein, that an antibody that specifically binds renalase, binds with a protein of the invention, such as, but not limited to human renalase or an immunogenic portion thereof. In one embodiment, the antibody is directed to rat renalase comprising the amino acid sequence of SEQ ID NO:2.

Polyclonal antibodies are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the renalase portion is rendered immunogenic (e.g., renalase conjugated with keyhole limpet hemocyanin, KLH) and a portion comprising the respective rodent and/or human renalase amino acid residues. The chimeric proteins are produced by cloning the appropriate nucleic acids encoding renalase (e.g., SEQ ID NO: 1) into a plasmid vector suitable for this purpose, such as but not limited to, pMAL-2 or pCMX.

However, the invention should not be construed as being limited solely to these antibodies or to these portions of the protein antigens. Rather, the invention should be construed to include other antibodies, as that term is defined elsewhere herein, to rat and human renalase, or portions thereof. Further, the present invention should be construed to encompass antibodies, inter alia, bind with renalase and they are able to bind renalase present on Western blots, in immunohistochemical staining of tissues thereby localizing renalase in the tissues, and in immunofluorescence microscopy of a cell transiently transfected with a nucleic acid encoding at least a portion of renalase.

One skilled in the art would appreciate, based upon the disclosure provided herein, that the antibody can specifically bind with any portion of the protein and the full-length protein can be used to generate antibodies specific therefor. However, the present invention is not limited to using the full-length protein as an immunogen. Rather, the present invention includes using an immunogenic portion of the protein to produce an antibody that specifically binds with mammalian renalase. That is, the invention includes immunizing an animal using an immunogenic portion, or antigenic determinant, of the renalase protein. The antibodies can be produced by immunizing an animal such as, but not limited to, a rabbit or a mouse, with a protein of the invention, or a portion thereof, or by immunizing an animal using a protein comprising at least a portion of renalase, or a fusion protein including a tag polypeptide portion comprising, for example, a maltose binding protein tag polypeptide portion covalently linked with a portion comprising the appropriate renalase amino acid residues. One skilled in the art would appreciate, based upon the disclosure provided herein, that smaller fragments of these proteins can also be used to produce antibodies that specifically bind renalase.

One skilled in the art would appreciate, based upon the disclosure provided herein, that various portions of an isolated renalase polypeptide can be used to generate antibodies to either highly conserved regions of renalase or to non-conserved regions of the polypeptide. As disclosed elsewhere herein, renalase comprises various conserved domains including, but not limited to, a putative signal peptide from at the N terminus, a FAD binding domain (amino acid residues from about 4 to 35); an amine oxidase domain (amino acid residues from about 75 to 339).

Once armed with the sequence of renalase and the detailed analysis localizing the various conserved and non-conserved domains of the protein, the skilled artisan would understand, based upon the disclosure provided herein, how to obtain antibodies specific for the various portions of a mammalian renalase polypeptide using methods well-known in the art or to be developed, as well as methods disclosed herein.

Further, the skilled artisan, based upon the disclosure provided herein, would appreciate that the non-conserved regions of a protein of interest can be more immunogenic than the highly conserved regions which are conserved among various organisms. Further, immunization using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of each renalase molecule can be used to produce antibodies that are specific only for that renalase and do not cross-react non-specifically with other renalases or with other proteins.

Alternatively, the skilled artisan would also understand, based upon the disclosure provided herein, that antibodies developed using a region that is conserved among one or more renalase molecule can be used to produce antibodies that react specifically with one or more renalase molecule. Methods for producing antibodies that specifically bind with a conserved protein domain which may otherwise be less immunogenic than other portions of the protein are well-known in the art and include, but are not limited to, conjugating the protein fragment of interest to a molecule (e.g., keyhole limpet hemocyanin, and the like), thereby rendering the protein domain immunogenic, or by the use of adjuvants (e.g., Freund's complete and/or incomplete adjuvant, and the like), or both. Thus, the invention encompasses antibodies that recognize at least one renalase and antibodies that specifically bind with more than one renalase, including antibodies that specifically bind with all renalase.

One skilled in the art would appreciate, based upon the disclosure provided herein, which portions of renalase are less homologous with other proteins sharing conserved domains. However, the present invention is not limited to any particular domain; instead, the skilled artisan would understand that other non-conserved regions of the renalase proteins of the invention can be used to produce the antibodies of the invention as disclosed herein.

Therefore, the skilled artisan would appreciate, based upon the disclosure provided herein, that the present invention encompasses antibodies that neutralize and/or inhibit renalase activity (e.g., by inhibiting necessary renalase receptor/ligand interactions) which antibodies can recognize one or more renalases, including, but not limited to human renalase, as well as renalases from various species (e.g., mouse renalase).

The invention should not be construed as being limited solely to the antibodies disclosed herein or to any particular immunogenic portion of the proteins of the invention. Rather, the invention should be construed to include other antibodies, as that term is defined elsewhere herein, to renalase, or portions thereof, or to proteins sharing at least about 15% homology with a polypeptide having the amino acid sequence of SEQ ID NO: 2. In other embodiments, the polypeptide is at least about 20% homologous, or at least about 25% homologous, or at least about 30% homologous, or at least about 35% homologous, or at least about 40% homologous, or at least about 45% homologous, or at least about 50% homologous, or at least about 55% homologous, or at least about 60% homologous, or at least about 65% homologous, or at least about 70% homologous, or at least about 75% homologous, or at least about 80% homologous, or at least about 85% homologous, or at least about 90% homologous, or at least about 95% homologous, or at least about 99% homologous to human renalase. In another embodiment, the polypeptide that specifically binds with an antibody specific for mammalian renalase is human renalase.

The invention encompasses polyclonal, monoclonal, synthetic antibodies, and the like. One skilled in the art would understand, based upon the disclosure provided herein, that the crucial feature of the antibody of the invention is that the antibody bind specifically with renalase. That is, the antibody of the invention recognizes renalase, or a fragment thereof (e.g., an immunogenic portion or antigenic determinant thereof), as demonstrated by antibody binding renalase on Western blots, in immunostaining of cells, and/o immunoprecipitation of renalase, using standard methods well-known in the art.

One skilled in the art would appreciate, based upon the disclosure provided herein, that the antibodies can be used to localize the relevant protein in a cell and to study the role(s) of the antigen recognized thereby in cell processes. Moreover, the antibodies can be used to detect and or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art.

In addition, the antibody can be used to decrease the level of renalase in a cell thereby inhibiting the effect(s) of renalase in a cell. Thus, by administering the antibody to a cell or to the tissues of an animal or to the animal itself, the required renalase receptor/ligand interactions are therefore inhibited such that the effect of renalase-mediated signaling are also inhibited. One skilled in the art would understand, based upon the disclosure provided herein, that detectable effects upon inhibiting renalase ligand/receptor interaction using an anti-renalase antibody can include, but are not limited to, decreased proliferation of cells, decreased cell migration, decreased negative modeling, decreased adventitial fibrosis, decreased arterial restenosis, decreased fibrosis in any organ or tissue, decreased ossification or bone formation, and the like.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein.

Further, the antibody of the invention may be "humanized" using the technology described in, for example, Wright et al. (supra), and in the references cited therein, and in Gu et al. (1997, Thrombosis and Hematocyst 77:755-759), and other methods of humanizing antibodies well-known in the art or to be developed.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

VII. Compositions

The invention includes a composition comprising an isolated nucleic complementary to a nucleic acid, or a portion thereof, encoding a mammalian renalase, which is in an antisense orientation with respect to transcription. Preferably, the composition comprises a pharmaceutically acceptable carrier.

The invention includes a composition comprising an isolated mammalian renalase polypeptide as described herein. Preferably, the composition comprises a pharmaceutically-acceptable carrier.

The invention also includes a composition comprising an antibody that specifically binds renalase. Preferably, the composition comprises a pharmaceutically-acceptable carrier.

The invention further includes a composition comprising an isolated nucleic acid encoding a mammalian renalase. Preferably, the composition comprises a pharmaceutically acceptable carrier.

The compositions can be used to administer renalase to a cell, a tissue, or an animal or to inhibit expression of renalase in a cell, a tissue, or an animal. The compositions are useful to treat a disease, disorder or condition mediated by altered expression of renalase such that decreasing or increasing renalase expression or the level of the protein in a cell, tissue, or animal, is beneficial to the animal. That is, where a disease, disorder or condition in an animal is mediated by or associate with altered level of renalase expression or protein level, the composition can be used to modulate such expression or protein level of renalase.

For administration to the mammal, a polypeptide, or a nucleic acid encoding it, and/or an antisense nucleic acid complementary to all or a portion thereof, can be suspended in any pharmaceutically acceptable carrier, for example, HEPES buffered saline at a pH of about 7.8.

Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers known to those skilled in the art are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

As used herein, "nanoparticle" is defined as a particle having a diameter of from 1 to 1000 nanometers, having any size, shape or morphology. The nanoparticle may even be a "nanoshell," which is a nanoparticle having a discrete dielectric or semiconducting core section surrounded by one or more conducting shell layers. A "nanoshell" is a subspecies of nanoparticles characterized by the discrete core/shell structure. Both nanoshells and nanoparticles may contain dopants for binding to, e.g., negatively charged molecules such as DNA, RNA and the like. Examples of commonly used, positively charged dopands include $Pr^3$, $Er^3$, and $Nd^3$. As used herein, "shell" means one or more shells that will generally surround at least a portion of one core. Several cores may be incorporated into a larger nanoshell. In one embodiment, the nanoparticles are administered to the animal using standard methods.

As used herein, the term "delivering" nanoparticles is used to describe the placement of the nanoparticles attached to, next to, or sufficiently close to the target location, e.g., intravenously, in order to maximize the number of particles that will be able to contact cells at the target location.

The compositions of the present invention include nucleic acid sequences bound in, to or about nanoparticles, and methods for their use. The bound nanoparticles can be used for the delivery of the nucleic acid sequences to a variety of biological targets, such as endothelial cells. In one embodiment, the nucleic acids, e.g., a nucleic acid gene under the control of a promoter for gene expression is attached to a positively doped nanocore, which is then surrounded by a shell that includes a targeting ligand that is specific for a ligand target on, e.g., a cell of interest.

One embodiment of the invention relates to nucleic acid sequences bound in/to a nanoparticle. The nanoparticle is prepared by assembly of a "nanoparticle precursor." The nucleic acid sequence can generally be any nucleic acid sequence selected for delivery into a biological target. The nucleic acid sequence can be DNA, RNA, PNA, or other synthetic or modified nucleic acid sequences. In one embodiment, the nucleic acid sequence is a DNA sequence encoding human renalase (GenBank Accession No. BC 005364). The DNA sequence may be a naturally occurring sequence, a modified version of a naturally occurring sequence, or a synthetic sequence. In one embodiment, the nucleic acid is modified to maximize the percentage of codon usage of the target host. The naturally occurring sequence may be a human, monkey, cow, pig, horse, cat, dog, rat, mouse, bear, rabbit, moose, fish, sheep, or other animal sequence. The sequence may be modified to add or delete particular sequences. For example, a DNA sequence could be modified to, e.g., remove restriction sites, eliminate common cleavage or mutation sites, maximize binding to a nanocore. The sequence may be further modified to include additional sequences that aid in transcription, translation, localization, elimination of protein cleavage sites, addition of cleavage and/or processing sites, and addition or removal of glycosylation sites.

In one embodiment, the nanoparticle precursor includes a nucleic acid sequence bound to a nanoparticle polymer. The bond between a nanoparticle precursor and a nucleic acid may be non-covalent or covalent. The nanoparticle polymer may be any polymer that can assemble into a nanoparticle. For example, the nucleic acid sequence can be non-covalently bound to a first polymer. This first polymer can be a DNA binding cationic polymer such as polyethyleneimine ("PEI"). The first polymer can be covalently bound to a second polymer. The second polymer can be a hydrophilic polymer such as polyethylene glycol (PEG). For example, the second polymer can be conjugated to a fraction of the primary amines of PEI.

The hydrophilic polymer can be bound to a ligand such as an antibody. The antibody can be a polyclonal antibody or a monoclonal antibody, with a monoclonal antibody being presently preferred. The antibody can be specific for a biological receptor or other cellularly expressed protein. For example, the antibody can bind the lectin-like oxidized low density lipoprotein (LDL) receptor-1, Lox-1. Antibodies provide attractive binding abilities, but have relatively high steric bulk. Smaller antibody fragments or other binding peptides or molecules may be used as a ligand in various embodiments of the invention.

When the nanoparticle precursor self-assembles, the nucleic acid molecule is encapsulated within the formed nanoparticle, and the antibody or ligand is presented on the surface of the nanoparticle. The encapsulated nucleic acid molecule is partially or fully protected from degradation by the environment, enzymes, hydrolysis, or other degrading forces.

The assembled nanoparticle can generally have an average diameter of about 1 nm to about 1000 nm. More narrow ranges of diameters include about 10 nm to about 250 nm, and about 40 nm to about 100 nm.

An additional embodiment of the invention relates to the assembled nanoparticle. The assembled nanoparticle comprises nanoparticle precursors that have assembled in solution. The assembled nanoparticles preferably contain nucleic acid sequences in the internal volume of the nanoparticles, and antibodies or other binding peptides presented on the external face of the nanoparticles. The nanoparticles can generally be any shape, with about spherical being presently preferred. The antibodies preferably maintain their natural conformation, allowing binding to their natural targets.

The assembled nanoparticles can be present in a variety of formulations including in solution, dried, in liposomes, and so on. Specific examples of formulations include fullerene nanoparticles, aqueous nanoparticles comprised of oppositely charged polymers polyethylenimine (PEI) and dextran sulfate (DS) with zinc as a stabilizer, calcium phosphate nanoparticles, end-capped oligomers derived from Tris(hydroxymethyl)aminomethane bearing either a hydro- or a fluorocarbon tail; conjugated poly(aminopoly(ethylene glycol) cyanoacrylate-co-hexadecyl cyanoacrylate (poly(H(2) NPEGCA-co-HDCA) nanoparticles, biodegradable nanoparticles formulated from poly (D,L-lactide-co-glycolide) (PLGA), and water soluble, biodegradable polyphosphoester, poly(2-aminoethyl propylene phosphate) (PPE-EA) nanoparticles.

Aspects of the invention also relate to methods of preparing the assembled nanoparticles. The methods can comprise formation of a polymer conjugate, and contacting the polymer conjugate with nucleic acid to form a nanoparticle. The polymer conjugate includes a first polymer, a second polymer, and a ligand. The first polymer preferably binds in a non-covalent manner to nucleic acids. A presently preferred first polymer is a DNA binding cationic polymer such as polyethyleneimine ("PEI"). The second polymer can be a hydrophilic polymer such as polyethylene glycol ("PEG"). The ligand is presently preferred to be an antibody.

It is presently preferred that the parts of the polymer conjugate be connected by covalent bonds. The specific order of assembly of the polymer conjugate can be varied. For example, the first polymer and second polymer can be connected, then the ligand can be connected. Alternatively, the second polymer and the ligand can be connected, then the first polymer can be connected. The methods can further comprise an isolation or purification step to be performed after the contacting step. The described assembled nanoparticles can be used in a variety of applications. The nanoparticles can be used in in vitro or in vivo applications.

The present invention also provides a pharmaceutical composition of renalase in a microcrystalline form. Various methods for obtaining protein crystals have been developed, including the free interface diffusion method (Salemme, F. R. (1972) Arch. Biochem. Biophys. 151:533-539), vapor diffusion in the hanging or sitting drop method (McPherson, A. (1982) Preparation and Analysis of Protein Crystals, John Wiley and Son, New York, pp 82-127), and liquid dialysis (Bailey, K. (1940) Nature 145:934-935). Compared to non-crystalline proteins, crystalline proteins provide significant improvements in stability and concentration of proteins which leads to the opportunity for oral and parenteral delivery of proteins. In some instances, particular crystalline forms of a molecule may have more bioactive, dissolve faster, decompose less readily, and/or be easier to purify.

Proteins, glycoproteins, enzymes, antibodies, hormones and peptide crystals or crystal formulations can be encapsulated into compositions for biological delivery to humans and animals. Methods for crystallizing proteins, preparing stabilized formulations using pharmaceutical ingredients or excipients and optionally encapsulating them in a polymeric carrier to produce compositions and using such protein crystal formulations and compositions for biomedical applications, including delivery of therapeutic proteins and vaccines are well known in the art. For example, U.S. Pat. No. 6,541, 606, discloses that protein crystals or crystal formulations are encapsulated within a matrix comprising a polymeric carrier to form a composition. The formulations and compositions enhance preservation of the native biologically active tertiary structure of the proteins and create a reservoir which can slowly release active protein where and when it is needed. Such polymeric carriers include biocompatible and biodegradable polymers. The biologically active protein is subsequently released in a controlled manner over a period of time, as determined by the particular encapsulation technique, polymer formulation, crystal geometry, crystal solubility, crystal crosslinking and formulation conditions used.

The compositions of the invention may be administered via numerous routes, including, but not limited to, oral, rectal, vaginal, parenteral, topical, pulmonary, intranasal, buccal, or ophthalmic administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer renalase and/or a nucleic acid encoding the same according to the methods of the invention.

Compounds which are identified using any of the methods described herein may be formulated and administered to a mammal for treatment of arterial restenosis, adventitial fibrosis, fibrosis in any organ or tissue, negative remodeling, excessive bone formation, excessive ossification, and the like, are now described. The invention encompasses the preparation and use of pharmaceutical compositions comprising a compound useful for treatment of arterial restenosis, adventitial fibrosis, negative remodeling, and the like, as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject. As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyamide and cyanate scavengers.

Controlled- or sustained-release formulations of a pharmaceutical composition of the invention may be made using conventional technology. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water. A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration.

The compound can be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc. Vectors for Use in Practicing the Invention VIII. Methods A. Methods of Treating or Alleviating a Disease, Disorder or Condition Associated with or Mediated by Renalase Expression In one aspect of the present invention, there is provided a method to treat diseases, disorders, and conditions associated with or mediated by mammalian renalase. Such disease, disorders and conditions include, but are not limited to, ESRD, chronic hypertension, systolic hypertension, isolated systolic hypertension, diabetic hypertension, pulmonary hypertension, acute severe hypertension, asymptomatic left ventricular dysfunction, chronic congestive heart failure (CHF), myocardial infarction (MI), cardiac rhythm disturbance, stroke, atherosclerosis, depression, anxiety, mania and schizophrenia and the like.

The data disclosed herein suggest that over-expression of renalase, under-expression of renalase, overactive renalase, and inactive renalase are associated with various diseases, disorders or conditions such that methods of decreasing the level of renalase, increasing the level of renalase, decreasing the activity of renalase, and increasing the activity of renalase can potentially produce benefits, wherein the chosen method depends on the specific disorder, condition and/or disease under consideration. Therefore, a method of affecting the level of renalase to treat/alleviate a wide plethora of diseases, disorders, or conditions is disclosed herein, where the level of renalase is either decreased or increased compared with the level of renalase in the cell prior to treatment, or compared with the level of renalase in an otherwise identical cell that is obtained from a mammal known not to be afflicted with a disease, disorder or condition associated with, or mediated by, an altered level of renalase.

Whether expression of renalase, levels of the polypeptide, or its activity, is increased or decreased, one skilled in the art would appreciate, based on this disclosure, that methods of reducing or inducing renalase encompass administering naturally occurring or non-naturally occurring renalase, a renalase inhibitor, or a recombinant cell that either expresses or lacks expression of renalase. Thus, one skilled in the art would appreciate, based on the disclosure provided herein, that the present invention encompasses methods of treatments known in the art to effect either a detectable increase or decrease in the level of renalase expression or activity in a mammal.

The compositions of the present invention can be used to administer renalase to a cell, a tissue, or an animal or to promote expression of renalase in a cell, a tissue, or an animal. The compositions are useful to treat a disease, disorder or condition mediated by altered expression of renalase such that decreasing or increasing renalase expression or the level of the protein in a cell, tissue, or animal, is beneficial to the animal. That is, where a disease, disorder or condition in an animal is mediated by or associate with altered level of renalase expression or protein level, the composition can be used to modulate such expression or protein level of renalase.

One skilled in the art would understand, based upon the disclosure provided herein, that it may be useful to increase the level or activity of renalase in a cell. That is, the data disclosed herein demonstrating the association between renalase expression and hypertension, indicate that overexpression or an increase in renalase activity can lower blood pressure. This can be useful to treat or alleviate a disease, disorder of condition associated with or mediated by decreased expression, level, or activity of renalase (e.g., hypertension), when compared to the expression, level or activity of renalase in otherwise identical cell, tissue, or animal that does not suffer from the disease, disorder or condition, by administering naturally occurring or non-naturally occurring renalase. Such diseases, disorders or conditions include, but are not limited to ESRD, hypertension, a cardiovascular disorder, or a mental disorder.

The data disclosed herein demonstrate that renalase can regulate systemic blood pressure. Thus, the skilled artisan would appreciate, based upon the disclosure provided herein, that renalase, by metabolize catecholamines, can be used to treat cardiovascular diseases. Therefore, the present invention encompasses a method of increasing catecholamine metabolism comprising increasing the activity of renalase in circulation or the expression of renalase in a cell. For example, ESRD can be treated by administering to a mammal an effective amount of renalase. This is because, the data disclosed herein demonstrate that renalase is associated with ESRD. That is, the data demonstrate that lack of expression of renalase is correlated with ESRD. Further, the data disclosed herein demonstrate that infusion of recombinant renalase into rats results in a reduction in the rats' blood pressure, suggesting that renalase can be used to treat ESRD induced hypertension and other cardiovascular diseases.

In yet another embodiment, the invention includes a method of alleviating a disease, disorder or condition mediated by altered expression or activity of renalase by administering to a mammal an inhibitor that inhibits renalase expression and/or activity. Just like MAO inhibitors, a renalase inhibitor may prove useful in the treatment of CNS disorders such as mood disorders. Therefore, decreasing expression of renalase or decreasing activity of renalase with, for example, a chemical compound, a peptidomimetic, a small molecule, ribozymes, antisense nucleic acids, antibodies, and intrabodies that inhibit renalase, will increase monoamine content in the brain leading to the alleviation of the symptoms of these disorders. Thus, one of ordinary skill in the art would understand that inhibiting renalase, which can be accomplished by a variety of methods as more fully set forth elsewhere herein, is a useful treatment for CNS disorders, in particular mood disorders.

The CNS disorders include, but art not limited to, dementia, Alzheimer's disease, schizophrenia, psychosis, depression, headaches, and migraine headache. As used herein, the term "depression" includes depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

Other mood disorders encompassed within the term "depression" include dysthymic disorder with early or late onset and with or without atypical features; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

The compositions of the present invention are useful for the treatment of anxiety. As used herein, the term "anxiety" includes anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalized anxiety disorders.

"Generalized anxiety" is typically defined as an extended period (e.g. at least six months) of excessive anxiety or worry with symptoms on most days of that period. The anxiety and worry is difficult to control and may be accompanied by restlessness, being easily fatigued, difficulty concentrating, irritability, muscle tension, and disturbed sleep.

"Panic disorder" is defined as the presence of recurrent panic attacks followed by at least one month of persistent concern about having another panic attack. A "panic attack" is a discrete period in which there is a sudden onset of intense apprehension, fearfulness or terror. During a panic attack, the individual may experience a variety of symptoms including palpitations, sweating, trembling, shortness of breath, chest pain, nausea and dizziness. Panic disorder may occur with or without agoraphobia.

"Phobias" includes agoraphobia, specific phobias and social phobias. "Agoraphobia" is characterized by an anxiety about being in places or situations from which escape might be difficult or embarrassing or in which help may not be available in the event of a panic attack. Agoraphobia may occur without history of a panic attack. A "specific phobia" is characterized by clinically significant anxiety provoked by exposure to a specific feared object or situation. Specific phobias include the following subtypes: animal type, cued by animals or insects; natural environment type, cued by objects in the natural environment, for example storms, heights or water; blood-injection-injury type, cued by the sight of blood or an injury or by seeing or receiving an injection or other invasive medical procedure; situational type, cued by a specific situation such as public transportation, tunnels, bridges, elevators, flying, driving or enclosed spaces; and other type where fear is cued by other stimuli. Specific phobias may also be referred to as simple phobias. A "social phobia" is characterized by clinically significant anxiety provoked by exposure to certain types of social or performance circumstances. Social phobia may also be referred to as social anxiety disorder.

Other anxiety disorders encompassed within the term "anxiety" include anxiety disorders induced by alcohol, amphetamines, caffeine, *cannabis*, cocaine, hallucinogens, inhalants, phencyclidine, sedatives, hypnotics, anxiolytics and other substances, and adjustment disorders with anxiety or with mixed anxiety and depression.

Anxiety may be present with or without other disorders such as depression in mixed anxiety and depressive disorders. The compositions of the present invention are therefore useful in the treatment of anxiety with or without accompanying depression.

The invention further provides a method of alleviating a disease, disorder or condition mediated by altered expression of renalase by administering an antisense nucleic acid complementary to a nucleic acid encoding renalase to a patient afflicted with a disease, disorder or condition mediated by increased renalase expression compared to the level of renalase expression in otherwise identical but normal tissue, i.e., tissue which does not exhibit any detectable clinical parameters associated with the disease, disorder or condition being treated or alleviated. This, in turn, mediates a decrease in renalase expression thereby alleviating a disease, disorder or condition mediated by abnormal expression of renalase.

Although inhibition of renalase is exemplified by administering an antisense to a cell thereby inhibiting expression of renalase in the cell, one skilled in the art would appreciate that there are a wide plethora of methods for inhibiting protein expression and/or activity in a cell. Such methods include, but are not limited to, inhibiting expression of renalase using ribozymes, and inhibiting activity of the protein in a cell by, for instance, administering an antibody to the cell by, e.g., administering a nucleic acid encoding the antibody to the cell such that the antibody is expressed in the cell thus delivering the antibody to the cell cytosol. The use of these "intrabodies" to inhibit the intracellular activity of a protein are well-known in the art. See, e.g., Verma et al. (1997, Nature 389:239-242; Benhar & Pastan, 1995, J. Biol. Chem. 270:23373-23380; Willuda et al., 1999, Cancer Res. 59:5758-5767; and Worn et al., 2000, J. Biol. Chem. 275:2795-2803). Therefore, the present invention encompasses any method of inhibiting the activity of a protein of interest in a cell using such methods as are known in the art or to be developed in the future.

In another embodiment of the invention, an individual suffering from a disease, disorder or a condition that is associated with or mediated by renalase expression can be treated by supplementing, augmenting and/or replacing defective cells with cells that lack renalase expression. The cells can be derived from cells obtained from a normal syngeneic matched donor or cells obtained from the individual to be treated. The cells may be genetically modified to inhibit renalase expression. Alternatively, the cells can be modified to increase renalase expression using recombinant methods well-known in the art. Also, the invention encompasses using normal cells obtained from an otherwise identical donor that does not suffer from any disease or disorder associated with altered renalase expression, which cells can be administered to a mammal in need thereof.

Additionally, the invention includes ex vivo techniques where a cell is obtained from the mammal, modified to express increased or decreased level of renalase, and reintroduced into the mammal. Moreover, cells from the mammal which express a normal level of renalase, compared with the level of renalase expressed in an otherwise identical cell obtained from a like mammal not suffering from any condition associated with altered renalase expression, can be grown and expanded and an effective number of the cells can be reintroduced into the mammal. Such methods include cell and gene therapy techniques relating to use of bone marrow stromal cells which methods are well-known in the art. Thus, one skilled in the art would appreciate that cell therapy and gene therapy relating to cells that have or lack detectable renalase expression wherein the cells are administered in vivo are encompassed in the present invention.

In addition to replacing defective cells with repaired cells or normal cells from syngeneic, immunologically-matched donors, the method of the invention may also be used to facilitate expression of a desired protein that when secreted in an animal, has a beneficial effect. That is, cells may be isolated, furnished with a gene encoding renalase and introduced into the donor or into a syngeneic matched recipient wherein expression of exogenous renalase exerts a therapeutic effect.

One skilled in the art would understand, based upon the disclosure provided herein, that secretion of renalase from a cell is contemplated in the present invention. That is, the routineer would appreciate, based upon the disclosure provided herein, that secretion of renalase from a cell can be a useful therapeutic method and that the present invention includes secretion of renalase from a cell. Secretion of renalase from a cell can be effected according to standard methods well-known in the art and methods to be developed in the future. Such methods include, but are not limited to, covalently linking a nucleic acid encoding a signal peptide of a secreted molecule to the 5' end of an isolated nucleic acid encoding renalase. A wide plethora of signal sequences that can be used to mediate secretion of a protein from a cell are available and well-known in the art and the invention includes those as well as sequences to be developed in the future to drive secretion of a protein from a cell.

This aspect of the invention relates to gene therapy in which therapeutic amounts of renalase are administered to an individual. That is, according to some aspects of the present invention, recombinant cells transfected with either nucleic acid encoding renalase, antisense nucleic acids, or a knockout targeting vector of the invention, can be used as cell therapeutics to treat a disease, disorder or a condition characterized by altered expression of renalase, including the lack of expression of renalase.

In particular, a gene construct that comprises a heterologous gene which encodes renalase is introduced into cells. These recombinant cells are used to purify isolated renalase, which was is administered to an animal. One skilled in the art would understand, based upon the disclosure provided herein, that instead of administering an isolated renalase polypeptide, renalase can be administered to a mammal in need thereof by administering to the mammal the recombinant cells themselves. This will benefit the recipient individual who will benefit when the protein is expressed and secreted by the recombinant cell into the recipient's system.

According to the present invention, gene constructs comprising nucleotide sequences of the invention are introduced into cells. That is, the cells, referred to herein as "recombinant cells," are genetically altered to introduce a nucleic acid encoding renalase or a nucleic acid that inhibits renalase expression in and/or secretion by the recombinant cell (e.g., an antisense renalase nucleic acid, a nucleic acid encoding an anti-renalase antibody, and the like), thereby mediating a beneficial effect on an recipient to which the recombinant cell is administered. According to some aspects of the invention, cells obtained from the same individual to be treated or from another individual, or from a non-human animal, can be genetically altered to replace a defective renalase gene and/or to introduce a renalase gene whose expression has a beneficial effect on the individual, or to inhibit renalase expression which can have a beneficial effect on the individual.

In some aspects of the invention, an individual suffering from a disease, disorder or a condition can be treated by supplementing, augmenting and/or replacing defective or deficient nucleic acid encoding renalase by providing an isolated recombinant cells containing gene constructs that include normal, functioning copies of a nucleic acid encoding renalase. This aspect of the invention relates to gene therapy in which the individual is provided with a nucleic encoding renalase for which they are deficient in presence and/or function. The isolated nucleic acid encoding renalase provided by the cell compensates for the defective renalase expression of the individual, because, when the nucleic acid is expressed in the individual, a protein is produced which serves to alleviate or otherwise treat the disease, disorder or condition in the individual. Such nucleic acid preferably encodes a renalase polypeptide that is secreted from the recombinant cell.

In all cases in which a gene construct encoding renalase is transfected into a cell, the nucleic acid is operably linked to an appropriate promoter/regulatory sequence which is required to achieve expression of the nucleic acid in the recombinant cell. Such promoter/regulatory sequences include but are not limited to, constitutive and inducible and/or tissue specific and differentiation specific promoters, and are discussed elsewhere herein. Constitutive promoters include, but are not limited to, the cytomegalovirus immediate early promoter and the Rous sarcoma virus promoter. In addition, housekeeping promoters such as those which regulate expression of housekeeping genes may also be used. Other promoters include those which are preferentially expressed in cells of the central nervous system, such as, but not limited to the promoter for the gene encoding glial fibrillary acidic protein. In addition, promoter/regulatory elements may be selected such that gene expression is inducible. For example, a tetracycline inducible promoter may be used (Freundlich et al., 1997, Meth. Enzymol. 283:159-173).

The gene construct is preferably provided as an expression vector which includes the coding sequence of a mammalian renalase of the invention operably linked to essential promoter/regulatory sequences such that when the vector is transfected into the cell, the coding sequence is expressed by the cell. The coding sequence is operably linked to the promoter/regulatory elements necessary for expression of the sequence in the cells. The nucleotide sequence that encodes the protein may be cDNA, genomic DNA, synthesized DNA or a hybrid thereof or an RNA molecule such as mRNA. The gene construct, which includes the nucleotide sequence encoding renalase operably linked to the promoter/regulatory elements, may remain present in the cell as a functioning episomal molecule or it may integrate into the chromosomal DNA of the cell. Genetic material may be introduced into cells where it remains as separate genetic material in the form of a plasmid. Alternatively, linear DNA which can integrate into a host cell chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

In order for genetic material in an expression vector to be expressed, the promoter/regulatory elements must be operably linked to the nucleotide sequence that encodes the protein. In order to maximize protein production, promoter/regulatory sequences may be selected which are well suited for gene expression in the desired cells. Moreover, codons may be selected which are most efficiently transcribed in the cell. One having ordinary skill in the art can produce recombinant genetic material as expression vectors which are functional in the desired cells.

It is also contemplated that promoter/regulatory elements may be selected to facilitate tissue specific expression of the protein. Thus, for example, specific promoter/regulatory sequences may be provided such that the heterologous gene will only be expressed in the tissue where the recombinant cells are implanted. Additionally, the skilled artisan would appreciate, based upon the disclosure provided herein, that the renalase promoter can be operably linked to a nucleic acid of interest thereby directing the expression of the nucleic acid at the site of tissue or organ. Similarly, the renalase promoter can drive expression of a nucleic acid of interest where such expression is beneficial where high catecholamine circulation is a problem.

One skilled in the art would understand, based upon the disclosure provided herein, that the preferred tissues where the expression or lack of expression of renalase is to be targeted include, but are not limited to, ulcerations of the skin, bone fractures, and the like. In addition, promoter/regulatory elements may be selected such that gene expression is inducible. For example, a tetracycline inducible promoter may be used (Freundlich et al., 1997, Meth. Enzymol. 283:159-173).

Without wishing to be bound by any particular theory, the nucleic acid encoding renalase preferably includes a putative signal sequence as disclosed elsewhere herein (e.g., amino acids at N terminus of human renalase), which may direct the transport and secretion of the renalase encoded by the isolated nucleic acid in the recombinant cell. The signal sequence is likely processed and removed upon secretion of the mature renalase protein from the cell. Alternatively, without wishing to be bound by any particular theory, the putative signal sequence may not be cleaved, but may instead be a transmembrane domain.

In addition to providing cells with recombinant genetic material that either corrects a genetic defect in the cells, that encodes a protein which is otherwise not present in sufficient quantities and/or functional condition so that the genetic material corrects a genetic defect in the individual, and/or that encodes a protein which is useful as beneficial in the treatment or prevention of a particular disease, disorder or condition associated therewith, and that inhibits expression of renalase in the cell (e.g., a knock-out targeting vector, an antisense nucleic acid, and the like), genetic material can also be introduced into the recombinant cells used in the present invention to provide a means for selectively terminating such cells should such termination become desirable. Such means for targeting recombinant cells for destruction may be introduced into recombinant cells.

According to the invention, recombinant cells can be furnished with genetic material which renders them specifically susceptible to destruction. For example, recombinant cells may be provided with a gene that encodes a receptor that can be specifically targeted with a cytotoxic agent. An expressible form of a gene that can be used to induce selective cell death can be introduced into the recombinant cells. In such a system, cells expressing the protein encoded by the gene are susceptible to targeted killing under specific conditions or in, the presence or absence of specific agents. For example, an expressible form of a herpes virus thymidine kinase (herpes tk) gene can be introduced into the recombinant cells and used to induce selective cell death. When the introduced genetic material that includes the herpes tk gene is introduced into the individual, herpes tk will be produced. If it is desirable or necessary to kill the implanted recombinant cells, the drug gangcyclovir can be administered to the individual which will cause the selective killing of any cell producing herpes tk. Thus, a system can be provided which allows for the selective destruction of implanted recombinant cells.

One skilled in the art would understand, based upon the disclosure provided herein, that the present invention encompasses production of recombinant cells to either provide renalase to or inhibit renalase expression in a mammal. That is, the cells can be used to administer renalase to an animal or to deliver a molecule (e.g., a knock-out targeting vector, an antisense nucleic acid, a ribozyme, and antibody that specifically binds with renalase, and the like).

Administration of renalase to an animal can be used as a model system to study the mechanism of action of renalase or to develop model systems useful for the development of diagnostics and/or therapeutics for diseases, disorders or conditions associated with renalase expression.

Further, the delivery of renalase to an animal mediated by administration of recombinant cells expressing and secreting renalase can also be used to treat or alleviate a disease, disorder or condition where increasing the level of renalase mediates a therapeutic effect. More specifically, administration of renalase to an animal by administering a recombinant cell expressing a nucleic acid encoding renalase can be useful for treatment of ESRD, hypertension, cardiovascular diseases, among other things.

Alternatively, administration of recombinant cells comprising a nucleic acid the expression of which inhibits or reduces renalase expression, activity, and/or secretion from a cell, can be used as a model for the development of diagnostics and/or therapeutics useful for diseases, disorders or conditions associated with or mediated by renalase expression, activity, and/or secretion. The present invention encompasses that the recombinant cells can produce the molecule that inhibits renalase expression thereby providing such molecule to the animal. Alternatively, without wishing to be bound by any particular theory, the recombinant cells themselves, which are otherwise functional cells, except for the inability to express renalase, can perform the functions of otherwise identical but non-recombinant cells, without being subject to the renalase signaling pathway.

Cells, both obtained from an animal, from established cell lines that are commercially available or to be developed, or primary cells cultured in vitro, can be transfected using well known techniques readily available to those having ordinary skill in the art. Thus, the present invention is not limited to obtaining cells from a donor animal or from the patient animal itself. Rather, the invention includes using any cell that can be engineered using a nucleic acid of the invention such that the recombinant cell either expresses renalase (where it did not express renalase prior to being engineered, or where the cell produced renalase at a different level prior to the introduction of the nucleic acid into the cell) or the recombinant cell does not express renalase or expresses it at a lower level (where it expressed renalase before or expressed renalase at a different level prior to introduction of the nucleic acid into the cell).

Nucleic acids can be introduced into the cells using standard methods which are employed for introducing a gene construct into cells which express the protein encoded by the gene or which express a molecule that inhibits renalase expression. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA having a desired sequence into the cell. In some embodiments, recombinant retrovirus vectors are used to introduce DNA having a desired sequence into the cell. In some embodiments, standard calcium phosphate, DEAE dextran or lipid carrier mediated transfection techniques are employed to incorporate a desired DNA into dividing cells. Standard antibiotic resistance selection techniques can be used to identify and select transfected cells. In some embodiments, DNA is introduced directly into cells by microinjection. Similarly, well known electroporation or particle bombardment techniques can be used to introduce foreign DNA into cells. A second gene is usually co-transfected with and/or covalently linked to the nucleic acid encoding renalase, or knock-out targeting vector or antisense molecule thereto. The second gene is frequently a selectable antibiotic-resistance gene. Transfected recombinant cells can be selected by growing the cells in an antibiotic that kills cells that do not take up the selectable gene. In most cases where the two genes are unlinked and co-transfected, the cells that survive the antibiotic treatment contain and express both genes.

Methods for assessing the level of renalase (e.g., using anti-renalase antibodies in Western blot or other immune-based analyses such as ELISA) and/or methods for assessing the level of renalase expression in a cell and/or tissues (e.g., using Northern blot analysis, RT-PCR analysis, in situ hybridization, and the like) are disclosed herein or are well known to those skilled in the art. Such assays can be used to determine the "effective amount" of renalase (whether using an isolated nucleic acid, antibody, antisense nucleic acid, ribozyme, recombinant cell, and the like) to be administered to the animal in order to reduce or increase the level of renalase to a desired level.

B. Methods of Identifying Useful Compounds

The present invention further includes a method of identifying a compound that affects expression and/or activity of renalase in a cell. The method comprises contacting a cell with a test compound and comparing the level of expression and/or activity of renalase in the cell so contacted with the level of expression and/or activity of renalase in an otherwise identical cell not contacted with the compound. If the level of expression and/or activity of renalase is higher or lower in the cell contacted with the test compound compared to the level of expression and/or activity of renalase in the otherwise identical cell not contacted with the test compound, this is an indication that the test compound affects expression and/or activity of renalase in a cell.

Similarly, the present invention includes a method of identifying a compound that reduces expression and/or activity of renalase in a cell. The method comprises contacting a cell with a test compound and comparing the level of expression and/or activity of renalase in the cell contacted with the compound with the level of expression and/or activity of renalase in an otherwise identical cell, which is not contacted with the compound. If the level of expression and/or activity of renalase is lower in the cell contacted with the compound compared to the level in the cell that was not contacted with the compound, then that is an indication that the test compound affects reduces expression and/or activity of renalase in a cell.

One skilled in the art would appreciate, based on the disclosure provided herein, that the level of expression and/or activity of renalase in the cell can be measured by determining the level of expression and/or activity of mRNA encoding renalase. Alternatively, the level of expression and/or activity of mRNA encoding renalase can be determined by using immunological methods to assess renalase production from such mRNA as exemplified herein using Western blot analysis using an anti-renalase antibody of the invention. Further, nucleic acid-based detection methods, such as Northern blot and PCR assays and the like, can be used as well. In addition, the level of renalase activity in a cell can also be assessed by determining the level of various parameters which can be affected by renalase activity such as, for example, the level of renalase expression and/or activity in kidney, heart, skeletal muscle, and small intestine, and the like. Alternatively, the level of renalase activity can be assessed in an amine oxidase assay. Thus, one skilled in the art would appreciate, based upon the extensive disclosure and reduction to practice provided herein, that there are a plethora of methods which can be used to assess the level of expression and/or activity of renalase in a cell including those methods disclosed herein, methods well-known in the art, and other methods to be developed in the future.

Further, one skilled in the art would appreciate based on the disclosure provided herein that, as disclosed in the examples below, a cell which lacks endogenous renalase expression and/or activity can be transfected with a vector comprising an isolated nucleic acid encoding renalase whereby expression and/or activity of renalase is effected in the cell. The transfected cell is then contacted with the test compound thereby allowing the determination of whether the compound affects the expression and/or activity of renalase. Therefore, one skilled in the art armed with the present invention would be able to, by selectively transfecting a cell lacking detectable levels of renalase using renalase-expressing vectors, identify a compound which selectively affects renalase expression and/or activity.

The skilled artisan would further appreciate, based upon the disclosure provided herein, that where an isolated nucleic acid encoding renalase is administered to a cell lacking endogenous detectable levels of renalase expression and/or activity such that detectable renalase is produced by the cell, the isolated nucleic acid can comprise an additional nucleic acid encoding, e.g., a tag polypeptide, covalently linked thereto. This allows the detection of renalase expression and/or activity by detecting the expression and/or activity of the tag polypeptide. Thus, the present invention encompasses methods of detecting renalase expression and/or activity by detecting expression and/or activity of another molecule which is co-expressed with renalase.

The invention includes a method of identifying a protein that specifically binds with renalase. Renalase binds with at least one other protein, whereby such interaction with other protein(s) may affect the biological function of renalase. Thus, the invention encompasses methods, which are well-known in the art or to be developed, for identifying a protein that specifically binds with and/or associates with renalase. Such methods include, but are not limited to, protein binding assays wherein the target protein, i.e., renalase, is immobilized on an appropriate support and incubated under conditions that allow renalase binding with a renalase-associated protein. Renalase can be immobilized on a support using standard methods such as, but not limited to, production of renalase comprising a glutathione-S-transferase (GST) tag, a maltose binding protein (MBP) tag, or a $His_6$-tag, where the fusion protein is then bound to glutathione-Sepharose beads, a maltose-column, or a nickel chelation resin (e.g., His-Bind resin, Novagen, Madison, Wis.), respectively. The solid support is washed to remove proteins which may be non-specifically bound thereto and any renalase-associated protein can then be dissociated from the matrix thereby identifying a renalase-associated protein.

In addition, a protein that specifically binds with renalase, e.g., a receptor, a ligand, and/or other renalase-associated protein, can be identified using, for example, a yeast two hybrid assay. Yeast two hybrid assay methods are well-known in the art and can be performed using commercially available kits (e.g., MATCHMAKER™ Systems, Clontech Laboratories, Inc., Palo Alto, Calif., and other such kits) according to standard methods. Therefore, once armed with the teachings provided herein, e.g., the full amino and nucleic acid sequences of the "bait" protein, renalase, one skilled in the art can easily identify a protein that specifically binds with renalase such as, but not limited to, a renalase receptor protein, a renalase ligand, and the like.

One skilled in the art would understand, based upon the disclosure provided herein, that the invention encompasses any molecule identified using the methods discussed elsewhere herein. That is, molecules that associate with renalase, such as but not limited to, a renalase receptor protein, a renalase ligand protein, or both, can be used to develop therapeutics and diagnostics for diseases, disorders or conditions mediated by renalase interaction with a renalase-associated protein such as ESRD, hypertension, cardiovascular diseases, and the like. That is, one skilled in the art would appreciate, as more fully set forth elsewhere herein in discussing antibodies that specifically bind with renalase, that a renalase-associated protein can be used to develop therapeutics that inhibit renalase activity in a cell by inhibiting necessary renalase receptor/ligand interactions and other renalase binding interactions, which are required for renalase activity.

Renalase-associated proteins identified by the above-disclosed methods can be used directly to inhibit renalase interactions by contacting a cell with the renalase-associated protein, or a portion thereof, or they can be used to develop antibodies and/or peptidomimetics that can inhibit the renalase-associated interaction with renalase thereby inhibiting renalase function and activity. Thus, renalase-associated proteins, including a renalase receptor/ligand protein, are useful and are encompassed by the invention.

C. Methods of Diagnosis and Assessment of Therapies

The present invention includes methods of diagnosis certain diseases, disorders, or conditions such as, but not limited to ESRD, chronic kidney disease, hypertension, cardiovascular diseases such as asymptomatic left ventricular dysfunction, chronic congestive heart failure and atherosclerosis. Renalase can also be used as a diagnostic marker for acute renal failure (i.e. acute tubular necrosis, or ATN), and the like.

The method comprises obtaining a biological sample from the mammal and comparing the level of renalase (expression, amount, activity) in the sample with the level of renalase in a sample from a person who is not afflicted with a renal disease. A lower level of renalase in the sample from the patient compared with the level of renalase in the sample obtained from a person not afflicted with ESRD, ANT, or hypertension is an indication that the patient is afflicted with ESRD, ANT, or hypertension.

The invention includes a method of assessing the effectiveness of a treatment for ESRD in a mammal. The method comprises assessing the level of renalase expression, amount, and/or activity, before, during and after a specified course of treatment for ESRD since ESRD is associated with decreased renalase expression. This is because, as stated previously elsewhere and demonstrated by the data disclosed herein, renalase expression, amount and/or activity is associated with or increased catecholamine circulation which is feature of certain disease states (e.g., ESRD and hypertension). Thus, assessing the effect of a course of treatment upon renalase expression/amount/activity indicates the efficacy of the treatment such that a increased level of renalase expression, amount, or activity indicates that the treatment method is successful.

Without further description, one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way.

EXAMPLES

Overview

The experiments presented in this example may be summarized as follows. First, renalase was identified. To isolate this novel kidney-secreted proteins, the existing public databases, specifically the Mammalian Gene Collection Project (MGC) was utilized. A total of 114 candidate genes encoding novel secretory proteins was identified based on the following criteria: (i) candidate genes encode novel proteins, with less than 20% similarity/identity to existing proteins in the data base; (ii) putative proteins are predicted to harbor the signal peptide sequence (using 2 different methods of predicting signal peptide sequence); (iii) putative proteins do not contain transmembane domains (since some membrane proteins, such as type I membrane proteins, also harbor a signal peptide sequence).

This strategy offers several distinct advantages: analysis is restricted to novel genes only; it bypasses the cumbersome cloning process, trimming months or even years off of the search for an interesting gene; it allows immediate verification of gene expression in tissues, and of biochemical and function studies. Indeed, using this algorithm, one clone, MGC12474, was found to be highly expressed in the kidney (see below). Thus, this clone was chosen for further study.

It was found that MGC12474 encodes a protein with monoamine oxidase (MAO) activity. MAO is a flavin-adenosine-dinucleotide (FAD)-containing enzyme, which converts biogenic monoamines to their corresponding aldehydes. The enzymatic reaction (Massey et al., 2000) catalyzes the oxidation of monoamines via an oxidative cleavage of the α-CH bond of the substrate to form an imine product with the concomitant reduction of the flavin cofactor. The imine product is then hydrolyzed to the corresponding aldehyde and ammonia. The reduced flavin coenzyme reacts with oxygen to form hydrogen peroxide and the oxidized form of the flavin to complete the catalytic cycle.

Rabbit anti-renalase polyclonal antibody was also raised using a synthetic peptide derived from amino acid position 226-238 that is identical between human and mouse. Western blot study showed that this antibody recognized the same 37 Kd renalase-HA fusion protein as anti-HA antibody.

Moreover, it was found that renalase is secreted to the blood (see below for detail) in human, further demonstrating the nature of renalase being a secretory protein.

In order to facilitate the detection of the protein product, a HA tag at the C-terminus of renalase was engineered. Western blotting with both anti-HA and anti-renalase antibodies revealed a 37 Kd protein in the culture medium of kidney-derived HEK293 cells, indicating that renalase has a functional N-terminal signal sequence, and is secreted in the cell culture model used in these studies.

Figure 3A:
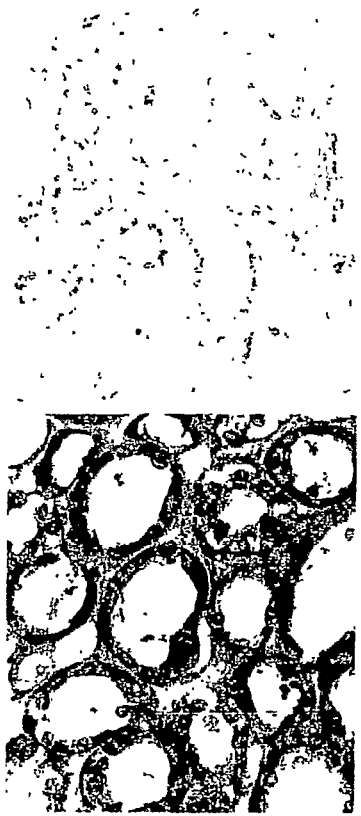
FIGS. 3A-3D show subcellular localization of renalase in the human kidney and heart.
Figure 3B:
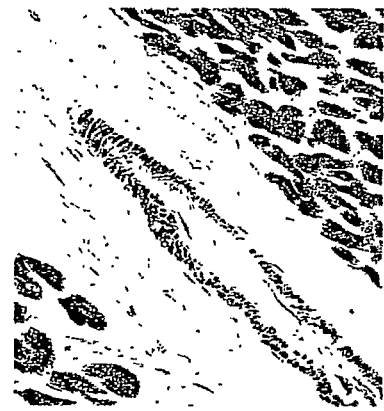
Figure 3C:
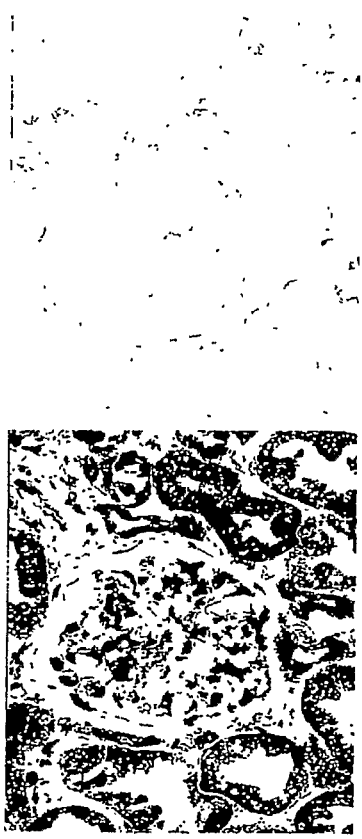

Furthermore, human blood was examined by western blotting using a renalase specific polyclonal antibody. FIG. 3b indicates that renalase is easily detectable in blood. To determine if the kidney is the major source of circulating renalase, we tested if blood levels were reduced in patients with severe kidney disease and decrease renal function. As shown in FIG. 3b, renalase was virtually undetectable in the blood of patients with ESRD receiving hemodialysis.

The experiments are described in more detail below.

Example 1

Identification and Analysis of the Gene Encoding Renalase

Material and Methods
Bioinformatics Analysis of MGC Database

All 12,563 distinct human full-ORF cDNAs available from *Mammalian Gene Collection Project* MGC as of the date of this experiment, were subjected to 3 rounds of sequential screening. The initial analysis of MGC was conducted on Dec. 24, 2001. First, genes without a GenBank Definition were chosen for more detailed analysis. Second, the predicted amino acid sequences encoded by genes selected in round 1 were analyzed using BLAST (http://www.ncbi.nlm.nih.gov/BLAST) and those encoding proteins with less than 20% identity with known proteins were chosen. Third, the presence of putative signal sequences was assessed using SignalP V2.0 (www.cbs.dtu.dk/services/SignalP-2.0/) and SOSUI signal Beta_Version (http://sosui.proteome.bio.tuat.ac.jp). Novel proteins with signal peptide sequence predicted by both methods were then subjected to domain search using Pfam. The cDNA clone encoding clones of interest were purchased from ATCC, sequenced on both strands (Yale University, Keck Foundation Biotechnology Resource Laboratory) and analyzed using BLAST.

MGC

The MGC project is a new effort by the NIH to generate full-length cDNA resources to facilitate the functional studies of human genes. This project provides publicly accessible resources to the worldwide research community. The MGC project entails the production of libraries, sequencing, and database and repository development, as well as the support of library construction, sequencing, and analytic technologies aimed at obtaining a full set of human and other mammalian full-length (open reading frame) sequences and clones of expressed genes (Rozanski et al., 1999; Tendera et al., 2001). Most importantly, MGC has established robust informatics tools to ensure that the selected clones potentially encode complete sequences. MGC produced 12,563 distinct human full-ORF cDNAs as of the date of this experiment, about 20% of which are novel genes (novel genes are defined as less than 20% similarity/identity to known proteins).

DNA Sequence

MGC12474 cDNA clone encoding renalase was purchased from ATCC and was sequenced on both strands (Yale University Keck Foundation Biotechnology Resource Laboratory) and analyzed for DNA sequence identity/similarity to the published sequence using BLASTN at the National Center for Biotechnology Information website (www.ncbi.nlm.nih.gov/BLAST/).

Northern Blot Analysis

Human multiple tissue Northern blot was obtained from CLONTECH and hybridized with the renalase cDNA labeled with [α-$^{32}$P]dCTP. Hybridizations were carried out in Rapid-hyb buffer (Amersham Pharmacia Biotech) containing labeled probe (~2×10$^6$ cpm/ml) at 62-68° C. for 1-2 h or overnight. The blot was washed under stringent conditions and exposed to Kodak XAR films. Glyceraldehyde-3-phosphate dehydrogenase cDNA was used as probe for the internal control for equal RNA loading.

Statistical Analysis

Standard paired Student's t-tests were used for comparisons between two groups. Standard unpaired Student's t-tests were used for group comparisons at equivalent periods. All data are means±SE, and P<0.05 was accepted as a statistically significant difference.

Results

Figure 1B:
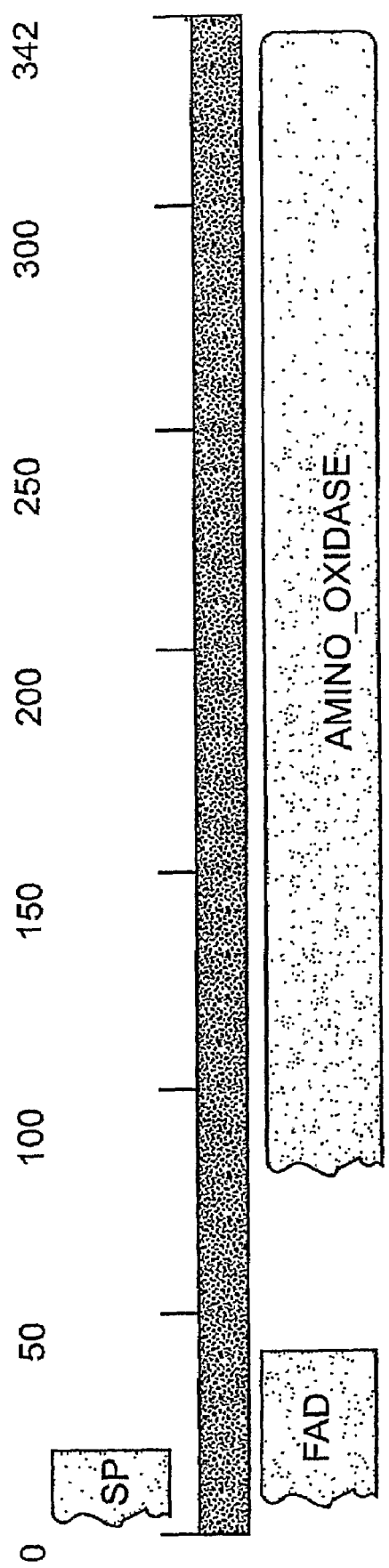
FIG. 1B depicts putative structural motifs detected in renalase: FAD: flavin adenine dinucleotide, SP: signal peptide.
Figure 1D:
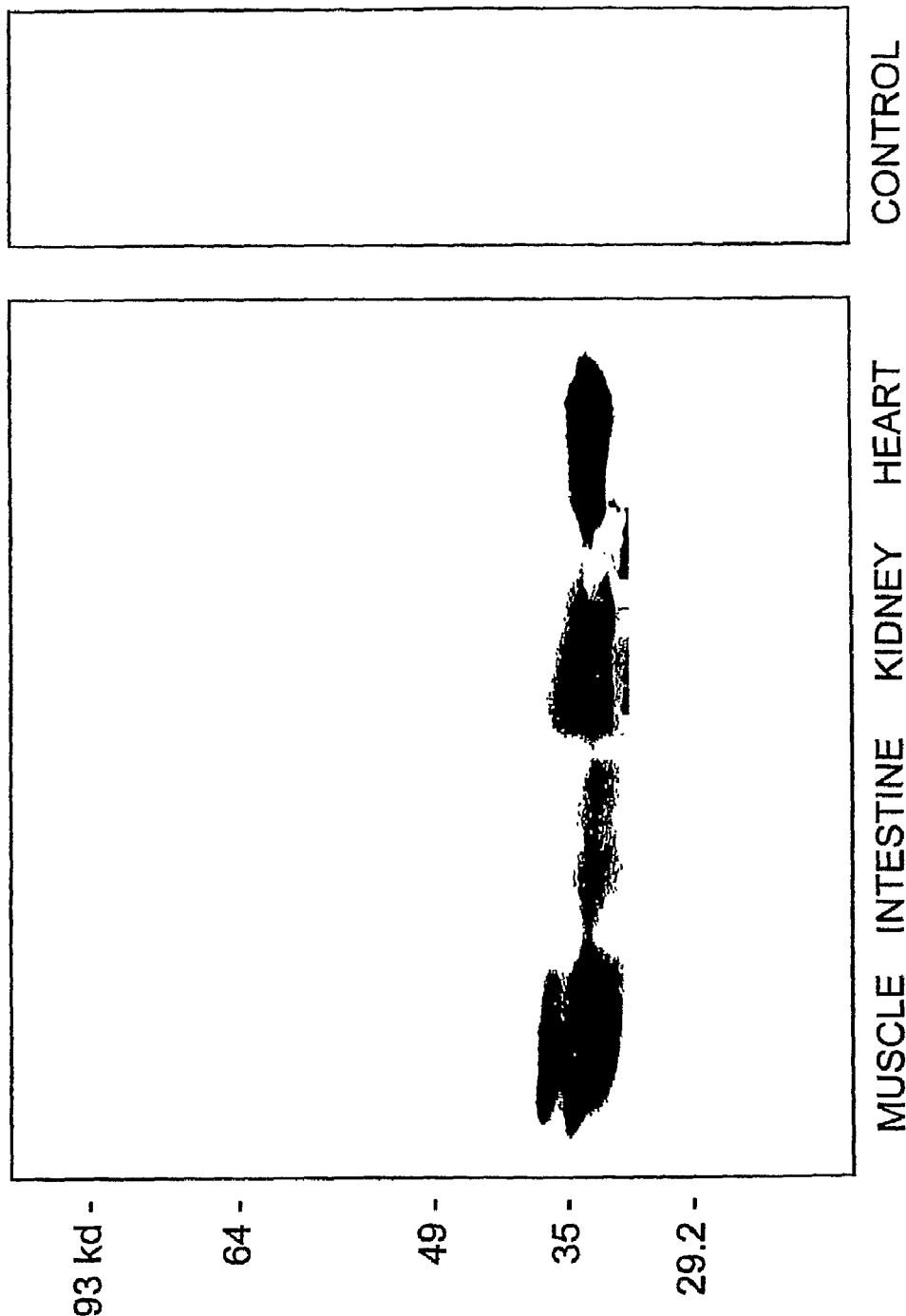
FIG. 1D is a Western blot analysis of rat tissue using a renalase polycolonal antibody.
Figure 2B:
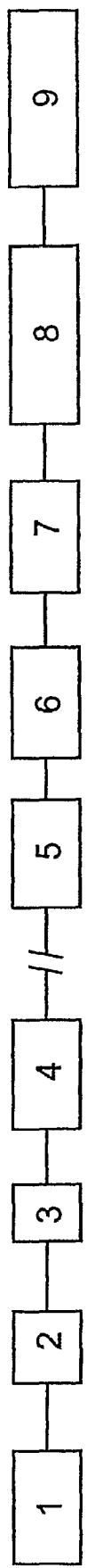
FIG. 2B depicts the genomic structure of renalase.

In order to isolate novel proteins with import biological roles, the existing public databases, specifically the Mammalian Gene Collection Project (MGC) were screened (Strausberg et al., 1999), using an algorithm designed to select new proteins that are likely to be secreted by the kidney. The MGC project is a new effort by the NIH to generate full-length cDNA resources in human and mouse to facilitate the functional study of the gene products (Strausberg et al., 1999; http://mgc.nci,nih.gov). To select candidate genes encoding secreted proteins, all the clones published by the MGC were studied. MGC produced 12,563 distinct human full-ORF cDNAs as of the date of these experiments, about 20% of which are novel genes (novel genes are defined as less than 20% similarity/identity to known proteins). By the time the MGC data analysis was completed on Aug. 1, 2003, a total of 114 candidate genes encoding novel secretory proteins were identified based on the following criteria: (i) candidate genes encode novel proteins, with less than 20% similarity/identity to existing proteins in the data base (ii) putative proteins are predicted to harbor the signal peptide sequence (using 2 different methods of predicting signal peptide sequence); (iii) putative proteins do not contain transmembane domains (since some of membrane proteins, such as type I membrane proteins, also harbor a signal peptide sequence). Tissue expression of each candidate gene was assessed by Northern blot analysis and revealed robust and preferential expression of one of these clones (MGC12474, GenBank accession # BC005364) in human kidney (FIG. 1A). MGC12474 has 1,474 nucleotides, and its longest open reading frame (nucleotides 22-1047) encodes a novel protein with 342 amino acids with a calculated molecular mass of 37.8 kDa (FIG. 2A). The human gene, which is named renalase, has 7 exons spanning approximately 311,000 bp and resides on chromosome 10 at q23.33 (FIG. 2B). Analysis, using MotifScan, revealed a signal peptide at the N terminus, a FAD binding site (amino acid 4-35), and an amine oxidase domain at amino acids 11-339 (FIG. 1B). Renalase has 13.2% amino acid identity with monoamine oxidase A (MAO-A) (FIG. 1C) and has a weak similarity to MAO-B (FIG. 2C).

Example 2

Renalase is Secreted by the Kidney

Construction of Gene Expression Cassettes (TAP Fragments)

We used a PCR-based approach that after two sequential PCR reactions, the 5'-CMV promoter and 3'-SV40pA were added to the 5'- and 3'-end of each candidate clone respectively. The detailed methodology is described by Liang et al. In brief, this method is comprised of two sequential PCR steps. The first step is carried out using primers (0.4 µg each) containing universal TAP ends and sequences specific to the target gene. The 5' universal end sequences are complementary to the DNA fragment containing the CMV immediate early gene promoter and are used in the second PCR step to attach the CMV promoter to the amplified gene. The 3' universal end overlaps with a DNA fragment that contains the SV40 early gene transcription terminator and is also used in the second-step PCR to attach the transcription terminator sequence to the amplified gene. To generate TAP fragment containing renalase, the 5'- and 3'-primers used for the first step PCR are as follows: 5'-oligo=5'-TGCAGGCAC-CGTCGTCGACTTAACAatgcgacccagggccccgccg (SEQ ID NO: 6, upper case is the 5'-TAP universal sequence which is used as an anchor for second step PCR, lower case is the clone #2-specific sequence starting at the ATG initiation site); 3'-oligo=5'-CATCAATGTATCTTATCATGTCTGAT-CAACCAGCTACCCATA CGATGTTCCAGAT-TACGCTttttggtagttcttcaataag (SEQ ID NO: 7, the first 25 bases are 3'-TAP universal sequence which is used as an anchor for second step PCR, underlined sequence encode HA followed by a stop codon TGA, lower case is the clone renalase-specific sequence starting at 3'-end minus the stop codon). The 5'- and 3'-primers used for the second step PCR are provided by the manufacturer (Gene Therapy Systems, Inc. San Diego. Calif.).

Gene Delivery and Expression

In vitro transfection was carried out using GenePORTER (Gene Therapy Systems, Inc. San Diego. Calif.) following the procedures recommended by the manufacturer. We consistently obtained 40-60% transfection efficiency as assessed using a Green Florescence Protein TAP fragment as control.

In vitro Translation

Renalase cDNA was cloned into pDNR-LIB which contains a T7 before the 5'-end of the insert. Renlase mRNA was transcribed and subsequently translated using the single tube protein® system 3 (Novagen, Calif.). A Luciferase T7 cDNA was used as a positive control. In vitro transcription-translation was carried out with 1 µg of plasmid DNA in 50 µl of reaction mixture supplemented with 50 µCi of [$^{35}$S] methionine (Amersham Pharmacia Biotech, NJ) according to manufacturer's instruction. 10 µl of the products were separated by 10% SDS-polyacrylamide gel electrophoresis, followed by autoradiography and Western blotting.

Gene Delivery and Expression

In vitro transfection was carried out using GenePORTER (Gene Therapy Systems, Inc.) following the procedures recommended by the manufacturer. We consistently obtained 40-60% transfection efficiency using the Green Florescence Protein TAP fragment as control. To test whether renalase is a secreted protein, we employed a PCR-based approach to generate transcriptionally active PCR (TAP) fragments that were used directly in in vivo expression experiments (Liang et al., 2002).

Renalase Antibody Generation.

The rabbit anti-renalase polyclonal antibody was generated by Proteintech Group, Chicago) using recombinant GST-renalase fusion protein as antigen. Ten weeks later, rabbits were boosted with the GST-renalase fusion protein. 6-8 weeks after the second injection of antigen, rabbits were bled and the anti-renalase antibody was affinity-purified.

Western Blot Analysis.

HEK 239 cells were grown in Dulbecco's modified Eagle's medium supplemented with 10% fetal bovine serum, 2 mM L-glutamine, and antibiotics. Cells were grown in six-well plates to 60-80% confluence and then transfected with TAP fragments containing renalase-HA fusion protein using Geneporter according to manufacturer's instruction. 48-72 h after transfection, the proteins from cell lysate were separated on a 10% SDS-polyacrylamide gel, transferred onto nitrocellulose membrane, and immunoblotted with an anti-HA monoclonal antibody (Roche Chemicals).

Immunocomplexes were detected with a secondary antibody conjugated to horseradish peroxidase (Pierce) and visualized with SuperSignal West Pico Luminol/enhancer solution (Pierce). To examine the secretory properties of the proteins encoded by the candidate genes, the culture media were subjected to Western blot analysis in parallel to the cell lysate. To examine the human plasma renalase, 10 microliters of plasma were analyzed by Western blot using a renalase-specific antibody.

In Situ Hybridization

In situ hybridization was performed as described previously. In brief, a 426-bp DNA fragment from MGC clone # 12474 was isolated by restriction enzyme HindIII and PstI digestion. It was then subcloned into the pBluescript® II KS(+) vector and in vitro transcribed into DIG-labeled RNA probes with DIG-labeling kit (Roche Biochemicals). The anti-sense was used to detect renalase, while the sense strand was used as control. These probes were used to hybridize with the sections cut from the heart and kidney tissues embedded in paraffin. The heart and kidney tissues of human adult were obtained from autopsy cases with the consent of family members and the approval of the university clinical research ethics committee. Tissues were fixed overnight with 4% parafomaldehyde in phosphate-buffered saline (PBS). The postmortem delay was 7 hours. The tissues were dehydrated through grade ethanol, cleared with xylene, and embedded in Parafilm, and 5-µm-thick sections were prepared.

After dewaxing and hydration, the sections were digested with Proteinase K (20 µg/ml) at 37° C. for 10 min. They were then post-fixed with 4% paraformaldehyde in PBS for 10 min. Hybridization was performed at 50° C. in a hybridization buffer containing 4×SSC, 10% dextran sulfate, 1×Denhardt's solution, 5 mM EDTA, 0.1% CHAPS, 50% deionized formamide, 200 µg/ml salmon sperm DNA, and 200 ng/ml DIG-labeled probe. The slides were washed four times for 15 min each in 2×SSC and then twice for 15 min each in 0.2×SSC/0.1% SDS at 50° C. Colorimetric detections were performed using an anti-DIG antibody conjugated to alkaline phosphatase followed by incubation with NBT/BCIP color substrates using a digoxygenin-nucleic acid detection kit (Roche, Germany). For human renalase, 5 min was needed for the color development in NBT/BCIP color substrate solution.

Results

Figure 3D:
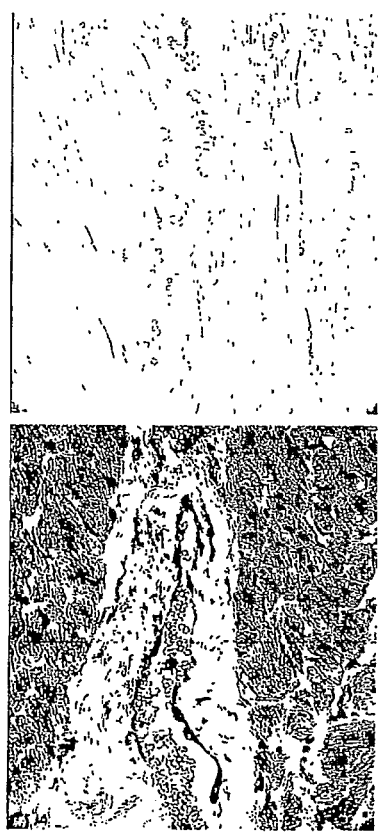

To determine the tissue distribution of renalase mRNA, we performed Northern blotting on panels of human tissues. The results depicted in FIG. 1A show that renalase mRNA is highly expressed in kidney with lower levels in several other tissue types. In situ hybridization studies were carried out to determine the spatial distribution of renalase mRNA in various human tissues (FIG. 3). A specific signal was detected in renal glomeruli, proximal tubules (FIG. 3A, left panel), and in cardiac myocytes (FIG. 3B, left panel). This distribution was confirmed by immunocytochemical experiments, as evidenced by the detection of renalase protein in renal glomeruli, proximal tubules (FIG. 3C, left panel), and in cardiac myocytes (FIG. 3D, left panels). These results indicate that high level renalase mRNA expression is tissue-specific, suggesting that it may have functions specific for cells found in kidney, skeletal muscles, heart and liver.

Figure 4A:
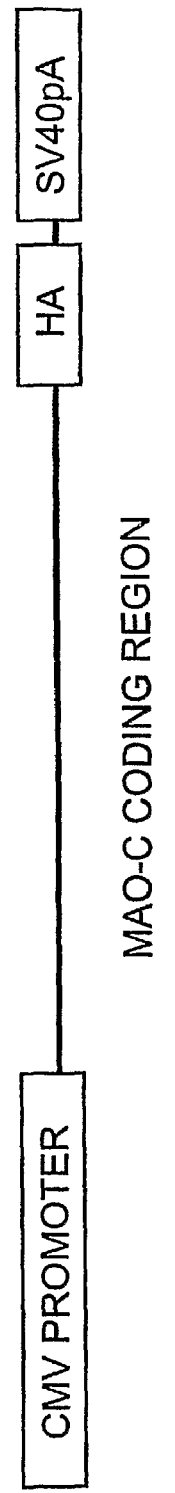

To test whether the candidate genes encode secreted proteins, we employed a PCR-based approach to generate transcriptionally active PCR (TAP) fragments that are used directly in in vivo expression experiments (6). In order to facilitate the detection of protein product, we also engineered a HA tag at the C-terminus of renalase (we avoided the N-terminus to preserve the integrity of the signal peptide). As shown in FIG. 4a, we fused the 5'-CMV promoter and 3'-SV40pA to the renalase-HA, we transfected the TAP fragment into HEK293 cells. Western blotting with anti-HA antibody revealed an expressed protein product of expected 37 Kd in the culture medium (FIG. 4b), consistent with the presence of a putative N-terminal signal sequence.

Unlike MAO-A, MAO-B and PAO that are either membrane-bound or confined to intracellular compartments, renalase is secreted into the blood, where it is detectable by western blotting. Amine oxidase activity has been measured in human plasma, and is believed to be mediated by vascular adhesion protein 1 (VAP-1), a copper-containing semicarbizide sensitive amine oxidase that is secreted by smooth muscle, adipocytes and endothelial cells (Salmi et al., 2001). VAP-1's substrate specificity and inhibitor profile are very different that of renalase. It metabolizes benzylamine and methylamine, and is inhibited by semicarbizide and hydroxylamine. Therefore, renalase is the only known amine oxidase that is secreted into circulation and that metabolizes circulating catecholamines.

Renalase expression appears limited to the kidney, heart, skeletal muscle and small intestine. The kidney exhibits the highest expression level and appears to be responsible for the bulk of circulating renalase. Indeed, renalase levels are dramatically reduced in patients with end-stage renal disease (ESRD) who are undergoing dialysis. The possibility cannot be excluded that the metabolic abnormalities associated with severe renal failure could decrease renalase secretion by the heart and skeletal muscles. Nonetheless, it is likely that the kidney is an important contributor to circulating renalase pool.

Interestingly, recent studies have shown that plasma dopamine and norepinephrine levels and sympathetic tone are consistently increased in patients with ESRD (Joles et al., 2004; Zoccali et al., 2002; Hausberg et al., 2002). A recent study has also found that sudden emotional stress may increase sympathetic stimulation leading to myocardial stunning (Wittstein et al., (2005) Neurohumoral features of myocardial stunning due to sudden emotional stress, New England Journal of Medicine. 352, 539-548). Heightened sympathetic tone may contribute to the pathogenesis of cardiovascular complications such as hypertension, left ventricular hypertrophy and dysfunction. These disturbances are likely contributors to the high mortality rate observed in patients with ESRD. Thus, it is possible that low renalase blood levels lead to the heightened sympathetic tone observed in ESRD patients, and that renalase administration may decrease the incidence of cardiovascular complication and improve survival.

Example 3

Renalase Degrades Catecholamines In vitro and Regulates Cardiac Function and Systemic Blood Pressure In vivo In vitro Transcription/translation MGC12474 clone was cloned into pDNR-LIB which contains a T7 before the 5'-end of the insert. renalase mRNA was transcribed and subsequently translated using the single tube protein® system 3 (Novagen, Cat # 70192). A Luciferase T7 cDNA was used as a positive control. In vitro transcription-translation was carried out with 1 μg of plasmid DNA in 50 μl of reaction mixture supplemented with 50 μCi of [$^{35}$S] methionine (Amersham Pharmacia Biotech) according to manufacturer's instruction. 10 μl of the products were separated by 10% SDS-polyacrylamide gel electrophoresis, followed by autoradiography and Western blotting.

Generation of GST-renalase Recombinant Protein

The renalase coding region (nt 24-1052) is amplified with sense primer 5'-TTTT GGA TCC ATG GCG CAG GTG CTG ATC GTG (SEQ ID NO: 8) and antisense: 3'-TTTT GAA TTC CTA AAT ATA ATT CTT TAA AGC (SEQ ID NO: 9). The PCR fragment, after digesting with Bam HI and Eco RI, was cloned into the pGEX-4T (Promega) in frame with GST tag (26 kDa) at the N-terminus. After verifying the correct cloning by DNA sequencing, the recombinant GST-renalase plasmid was transformed into E. Coli BL21 for recombinant fusion production. After transformation, 6 liter of bacterial culture was grown at 37° C. at 220 rpm for 16 hours with IPTG (0.5 mM) added in the last 3.5 hours of culture. 10 μM of FAD was also added at the time of IPTG induction. The presence of renalase was confirmed by Western Blotting with 40 μg protein of total bacterium lysates.

Renalase proteins can be purified directly from bacterial lysates with a one-step method using GSTrap column. The binding buffer contains PBS pH 7.0 (140 mM NaCl, 2.7 mM KCl, 10 mM $Na_2HPO_4$, and 1.8 mM $KH_2PO_4$, pH 7.0. The elution buffer. 50 mM Tris™-HCl and 10 mM reduced glutathione, pH 8.0. For sample preparation, 10 g E. coli sample was centrifuged and resuspened in binding buffer on ice. The sample was sonicated to release the GST-renalase fusion protein. The procedure of column purification is as follows:

1) Equilibrate the column with 5 column volumes of binding buffer,
2) Apply the sample use a flow rate of 0.2 ml/min,
3) Wash with 5-10 column volumes of binding buffer or until no material appears in the effluent
4) Elute with 5-10 column volumes of elution buffer.

One of the most important parameters affecting the binding of GST fusion proteins or other glutathione binding proteins to GSTrap is the flow rate. Due to the relatively slow binding kinetics between GST and glutathione, it is important to keep the flow rate low during sample application for maximum binding capacity. Volumes and times used for elution may vary among different batch proteins. Additional elutions with higher concentrations of glutathione may be required. Flow-through, wash and eluted material from the column should be monitored for GST fusion proteins using SDS-PAGE in combination with Western Blot if necessary.

GST-renalase Denaturation

Renalase protein denaturation by urea has been a subject of intense studies and controversy. The study of renalase denaturation is carried out as follows:

1. Prepare each of the two protein samples to be compared in 50 µl of sample buffer containing 50 mM Tris-HCl (pH 8) at a final protein concentration of approximately 1 mg/ml.

2. Denature the proteins by adding 50 µl of sample (from step 1) to 18 mg solid urea for a final urea concentration of 6 M.

3. Reduce the proteins by adding 5 µl of freshly-prepared 100 mM DTT (prepared in High-grade $H_2O$) and mix by vortexing. Incubate the solutions at room temperature for 1 hour.

GST-renalase Refolding

Efficient refolding process of denatured renalase, produced and purified to homogeneity, was denatured with 8M urea at neutral pH and rapidly diluted using various buffers. Rapid dilution with neutral pH buffers yielded low protein recovery. Reduction of protein concentration in the refolding solution did not improve protein recovery. Rapid dilution with alkaline buffers also yielded low protein recovery. However, dilution with mildly acidic buffers showed quantitative protein recovery with partial enzymatic activity, indicating that recovered protein was still arrested in the partially refolded state. Therefore, we further investigated the efficient refolding procedures of partially refolded renalase formed in the acidic buffers at low temperature (4° C.). Renalase enzymatic activity remained constant at pH 4. The same pH titration with incubation shorter than 12 h yielded less enzymatic activity. Refolding trials performed at room temperature led to aggregation, with almost half of the activity yield obtained at 4 degrees C. We conclude that rapid dilution of urea denatured Renalase under acidic pH at low temperature results in specific conformations that can then be converted to the native state by titration to physiological pH. The process is carried out as follows:

1. Purify renalase protein as inclusion bodies and solublize in neutral buffered 8M urea. Supplement the buffer with DTT as required by the protein.

2. Adjust the protein concentration to 0.1 mg/ml.

3. Dialysed 1000 µl of each protein against dialysis buffers as showing in order.

4. Slowly add 1000 µl of the protein solution to each dialysis tube while mixing the solution gently.

5. Dialysis at 4° C. for 12 hour according the buffer sequence.

6. Collect the Renalase by microfuge for 5 min.

7. Carefully pipette the liquid into a clean tube. This should contain refolded, soluble protein.

8. Assess successful refolding as follows:

It is best to perform a functional assay to determine if any active protein is present. Misfolded or aggregated protein will have a different activity reading than the correctly folded protein. Successful refolding is achieved when >30% of the input protein or activity is recovered in the soluble fraction.

Buffers used in the experiment include the following:

Buffer 1: 50 mM MES pH 5.5, 10 mM NaCl, 0.4 mM KCl, 2 mM MgCl2, 2 mM CaCl2, 0.75 M Guanidine HCl, 0.5% Triton X-100, 1 mM DTT, 0.1 mM FAD Buffer 2: 50 mM MES pH 5.5, 10 mM NaCl, 0.4 mM KCl, 2 mM MgCl2, 2 mM CaCl2, 0.5 M arginine, 0.05% polyethylene glycol 3,550, 1 mM GSH, 0.1 mM GSSH Buffer 3: 50 mM MES pH 5.5, 10 mM NaCl, 0.4 mM KCl, 1 mM EDTA, 0.4 M sucrose, 0.75 M Guanidine HCl, 0.5% Triton X-100, 0.05% polyethylene glycol 3,550, 1 mM DTT Buffer 4: 50 mM MES pH 5.5, 200 mM NaCl, 10 mM KCl, 2 mM MgCl2, 2 mM CaCl2, 0.5 M arginine, 0.5% Triton X-100, 1 mM GSH, 0.1 mM GSSH Buffer 5: 50 mM MES pH 5.5, 200 mM NaCl, 10 mM KCl, 1 mM EDTA, 0.4 M sucrose, 0.75 M Guanidine HC, 1 mM DTT Buffer 6: 50 mM MES pH 5.5, 200 mM NaCl, 10 mM KCl, 1 mM EDTA, 0.5 M arginine, 0.4 M sucrose, 0.5% Triton X-100, 0.05% polyethylene glycol 3,550, 1 mM GSH, 0.1 mM GSSH.

Amine Oxidase Assay

Enzyme assay of renalase was carried out using an Amplex Red Monoamine Oxidase Assay Kit (Molecular Probes, Cat # A-12214) that provides one-step fluorometric method for the continuous measurement of amine oxidase activity using a fluorescence microplate reader. The assay is based on the detection of $H_2O_2$ in a horseradish peroxidase-coupled reaction using 10-acetyl-3,7-dihydroxy-phenoxazine (Amplex Red reagent), a highly sensitive and stable probe for $H_2O_2$. Experiments were carried out according to manufacturer's instruction with a final substrate concentration of 2 mM.

Results

Structural analysis revealed that renalase contains an amino oxidase domain, suggesting it may play a role in amine oxidation. Therefore, we tested whether it had oxidase activity using a battery of amines as substrates. Renalase fusion protein in *E. Coli* was generated by cloning renalase cDNA into a Glutathione-S-Transferase (GST)-1-containing pGEX expression vector using the GST Gene Fusion System. As shown in FIG. 4*a*, renalase specifically metabolizes cathecholamines with the following rank order potency: dopamine>epinephrine>norepinephrine. Its enzymatic activity was unaffected by inhibitors of the FAD-containing amine oxidases, MAO-A and MAO-B (FIG. 4*b*).

Figure 5B:
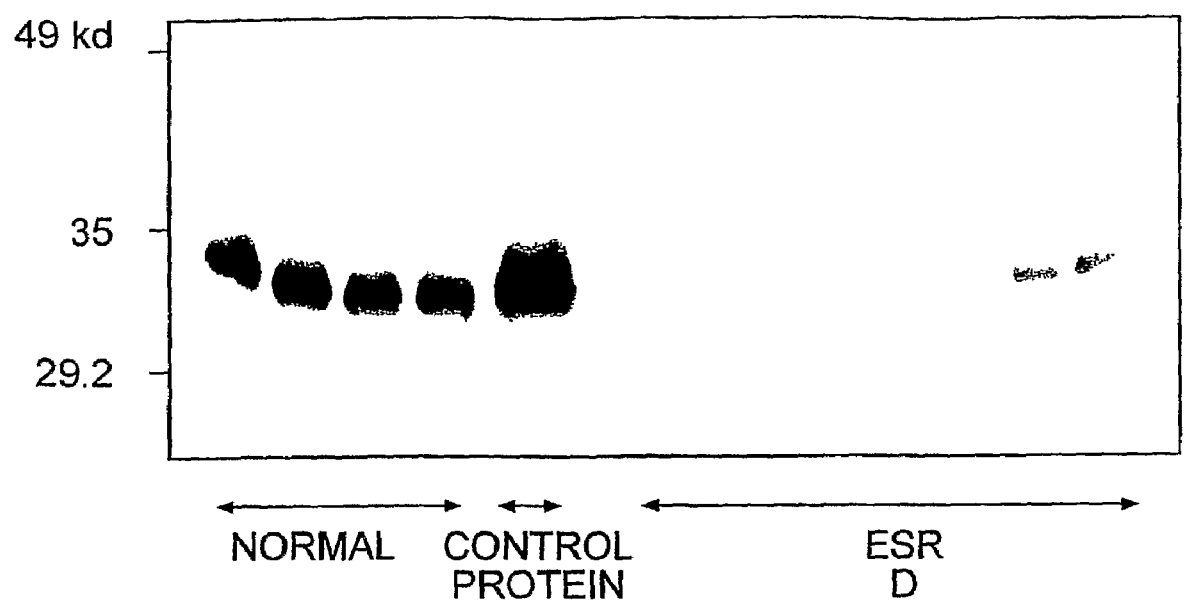

The GST-renalase fusion protein was purified to homogeneity using a Glutathione Sepharose column (FIG. 5*a*). The purified fusion protein has a MW of ~64 KD, in agreement with the MW of GST tag (26 KD) plus the predicted MW of renalase (37.8 KD). Since renalase is highly expressed in the kidney and is a secretory protein, it is conceivable that renalase is present in the circulation and that individuals with ESRD have much reduced level of renalase. When plasma samples are analyzed with the renalase-specific antibody by Western blot (FIG. 5B), we found the levels of renalase in patients with ESRD on hemodialysis are virtually undetectable, whereas the normal individuals have a circulating renalase concentration of about 7 mg/l.

Figure 6A:
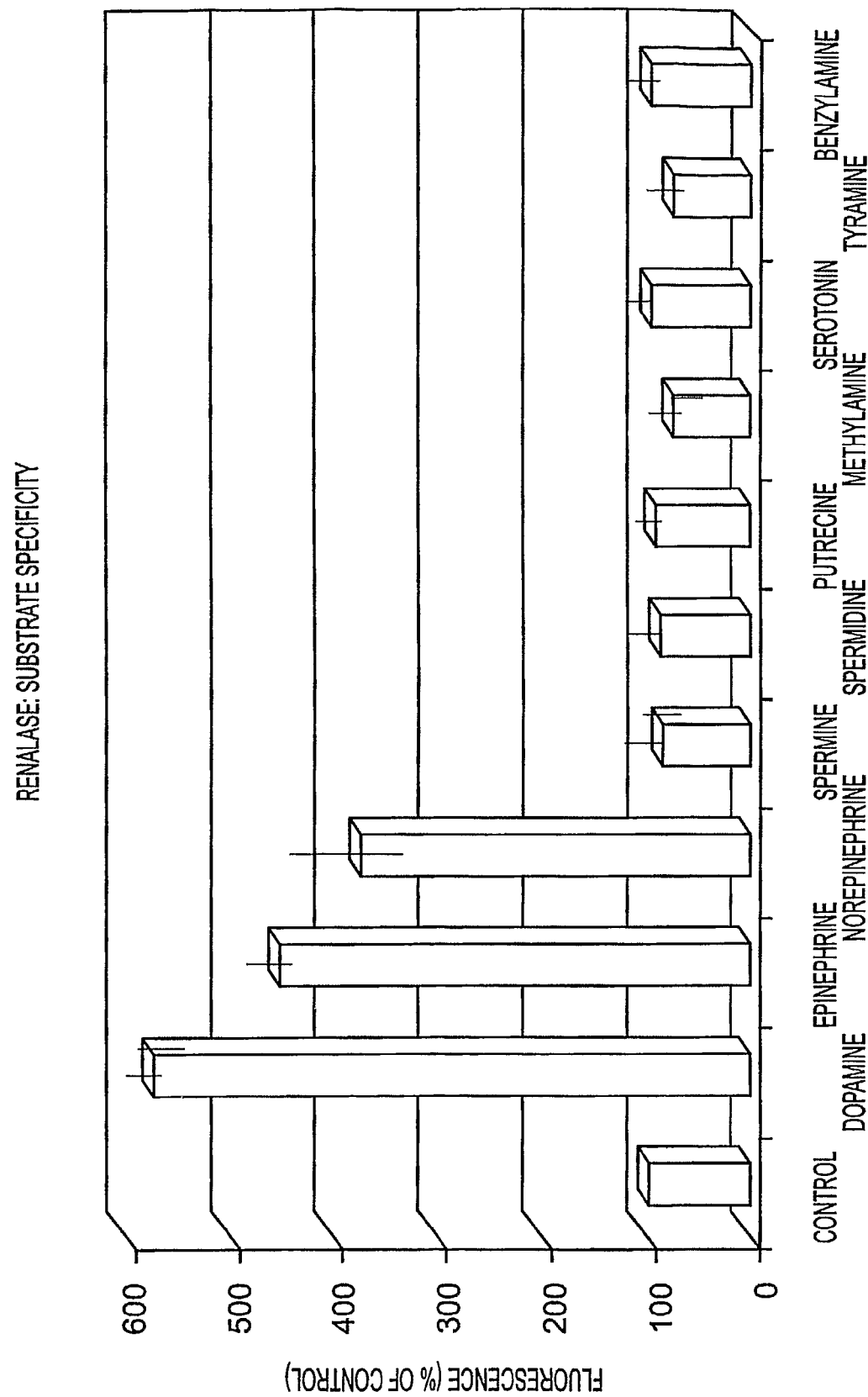
Figure 6B:
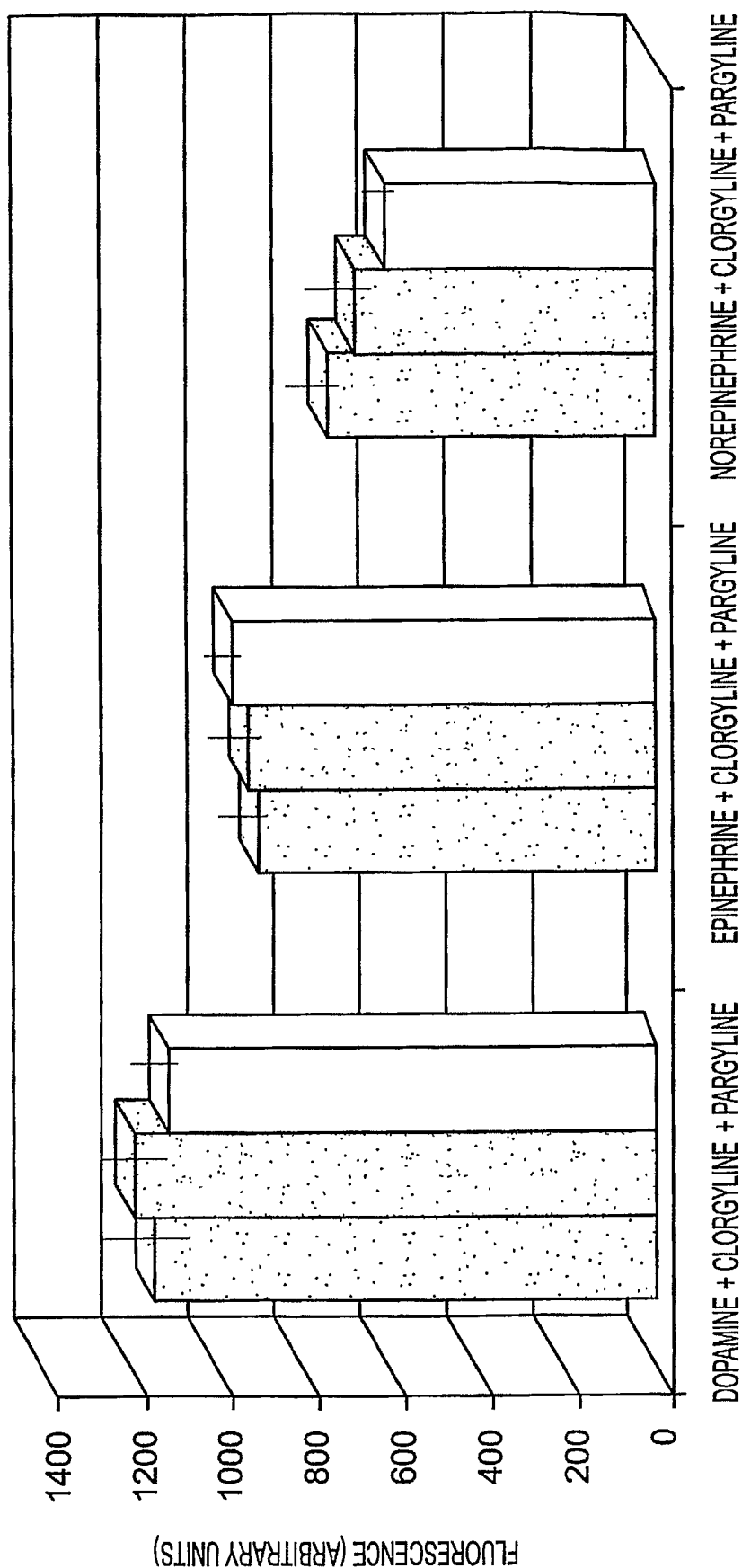

We subsequently tested whether renalase has an oxidase activity using a battery of amines as substrates. As shown in FIG. 6, GST-renalase fusion protein has significant oxidase activity when dopamine, norepinephrine and epinephrine (2 mM) were used as the substrate. Thus, it can be concluded that renalase is novel protein that metabolizes dopamine, norepinephrine and epinephrine.

Example 4

Renalase Regulates Systemic Blood Pressure

Hemodynamics Measurements

Sprague Dawley rats (150-250 g) were anesthetized with inactin (100 mg/kg). A catheter (PE-240) was placed in the trachea for airway protection and in the left jugular vein (PE-50) for intravenous infusion of a maintenance fluid solution consisting of normal saline with 6.25% bovine albumin, at a rate of 1.5 ml per 100 g body wt per hour. Core temperature was monitored through a rectal thermometer and body temperature was maintained at 37° C. using a heating pad. Arterial pressure and heart rate were continuously monitored through a PE-50 catheter inserted in the left carotid artery and connected to a pressure transducer (ADInstruments, CO, USA). Hemodynamic recordings were digitized, stored and analyzed using a PowerLab/8SP data acquisition system (ADIntruments). The rats were allowed 1 h to recover after completion of the surgical procedure, and the subsequent 30 minutes served as a control period. The experimental group then received a bolus intravenous injection of 0.5 mg of recombinant renalase in 0.5 ml PBS. The control group was injected with either 0.5 mg BSA or 0.5 mg recombinant glutathione transferase in 0.5 ml of PBS. Blood pressure and heart rate were continuously measured and recorded.

Figure 7A:
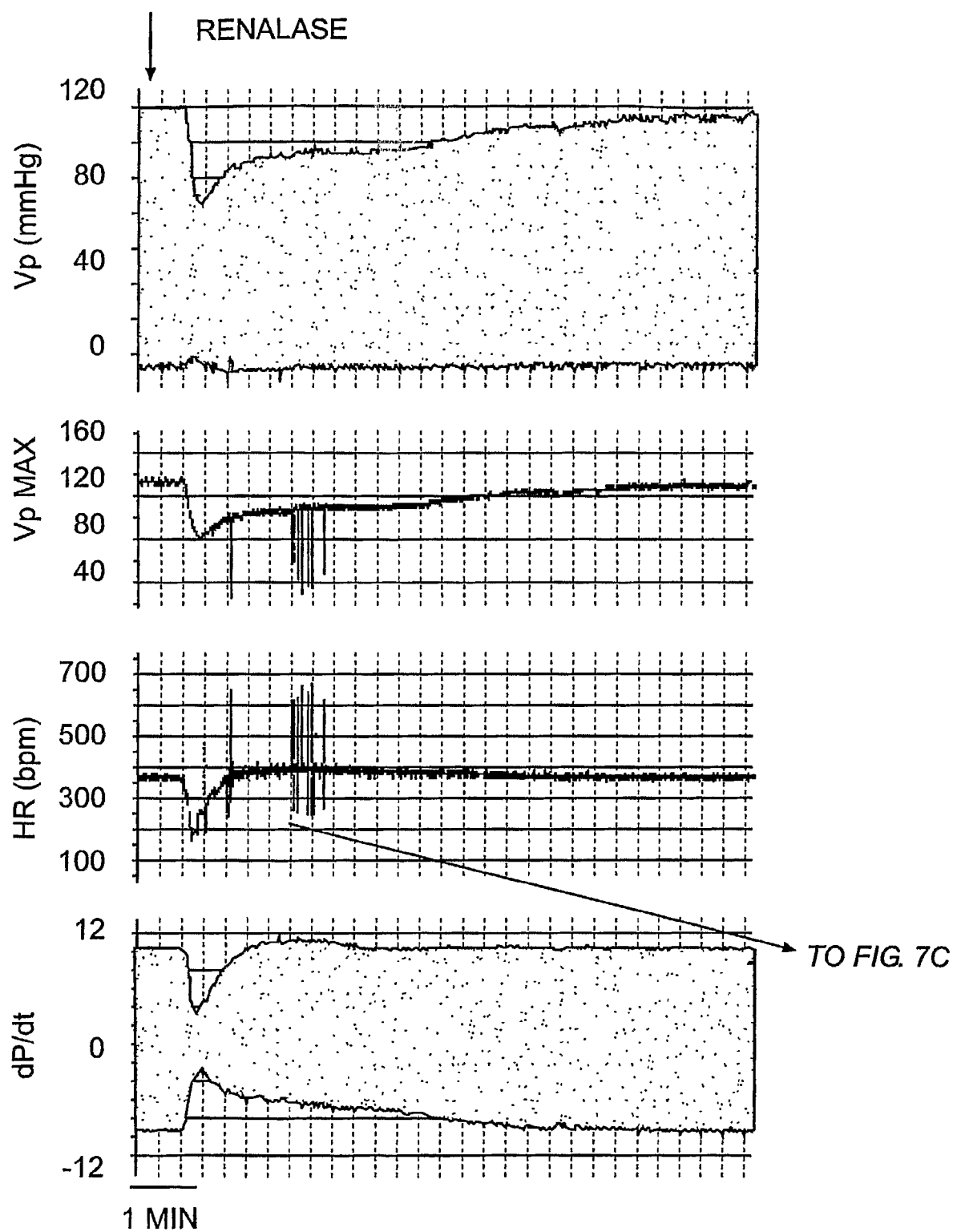
FIGS. 7A through 7G depict the hemodynamic effects of renalase; arrows denotes the timing of renalase injection, time scale is in minutes, heart rate is measured in beats per minute (bpm) and systolic and diastolic arterial blood pressures are expressed in millimeters of mercury (mm Hg).
Figure 7B:
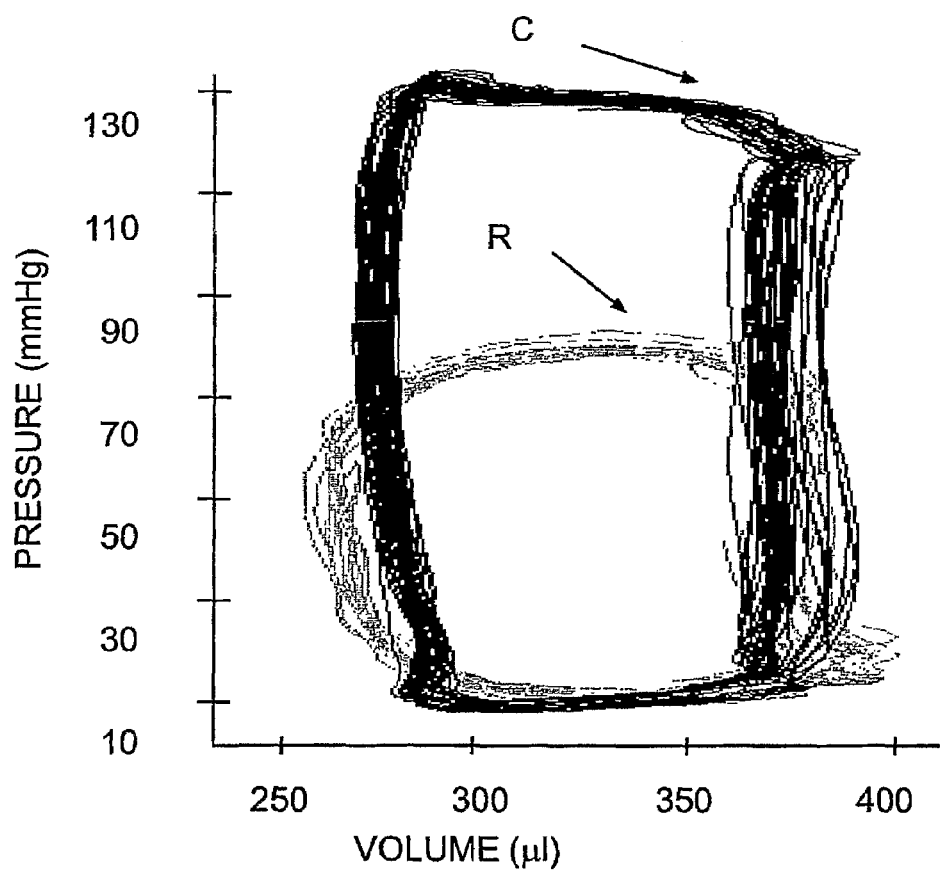
Figure 7C:
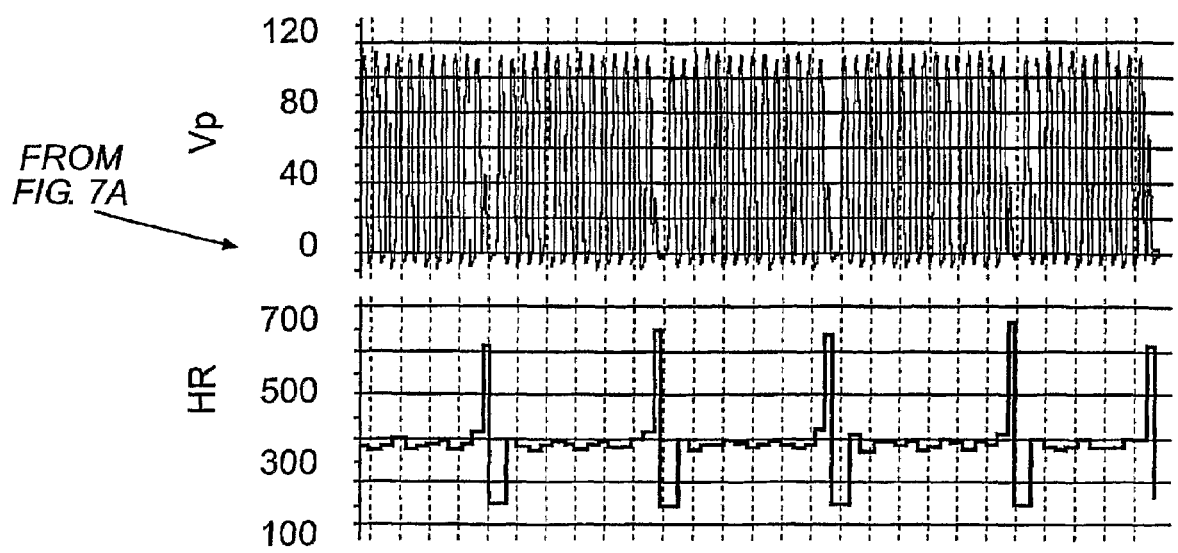
Figure 7E:
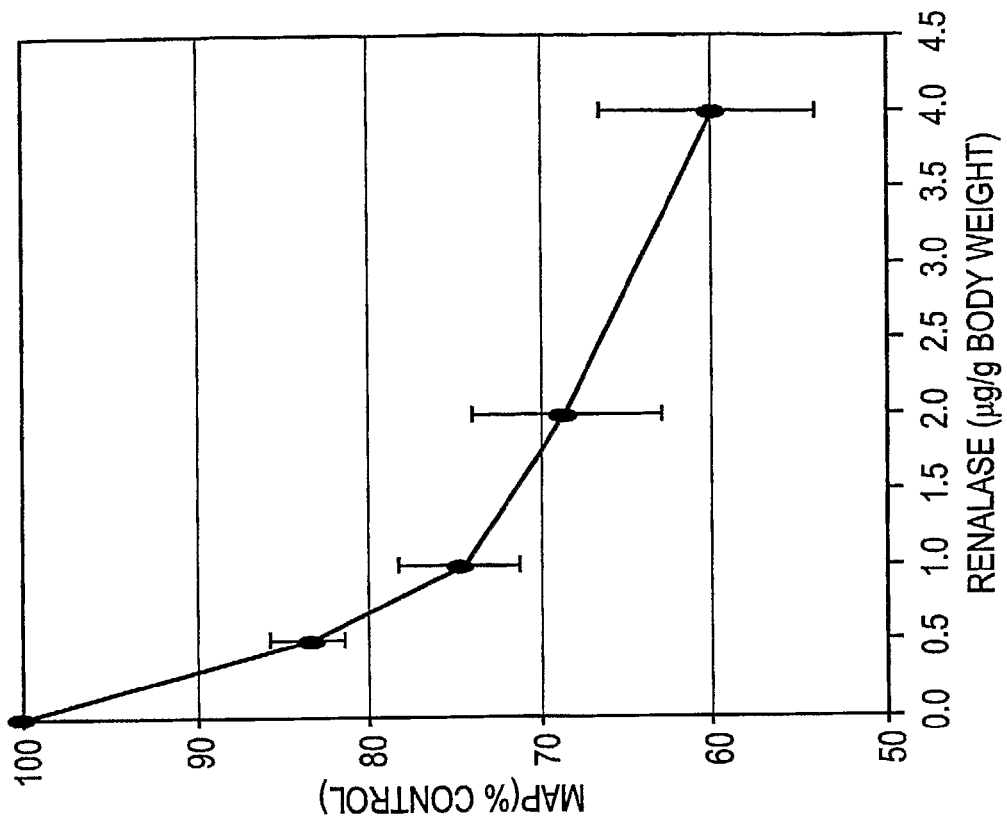
Figure 7D:
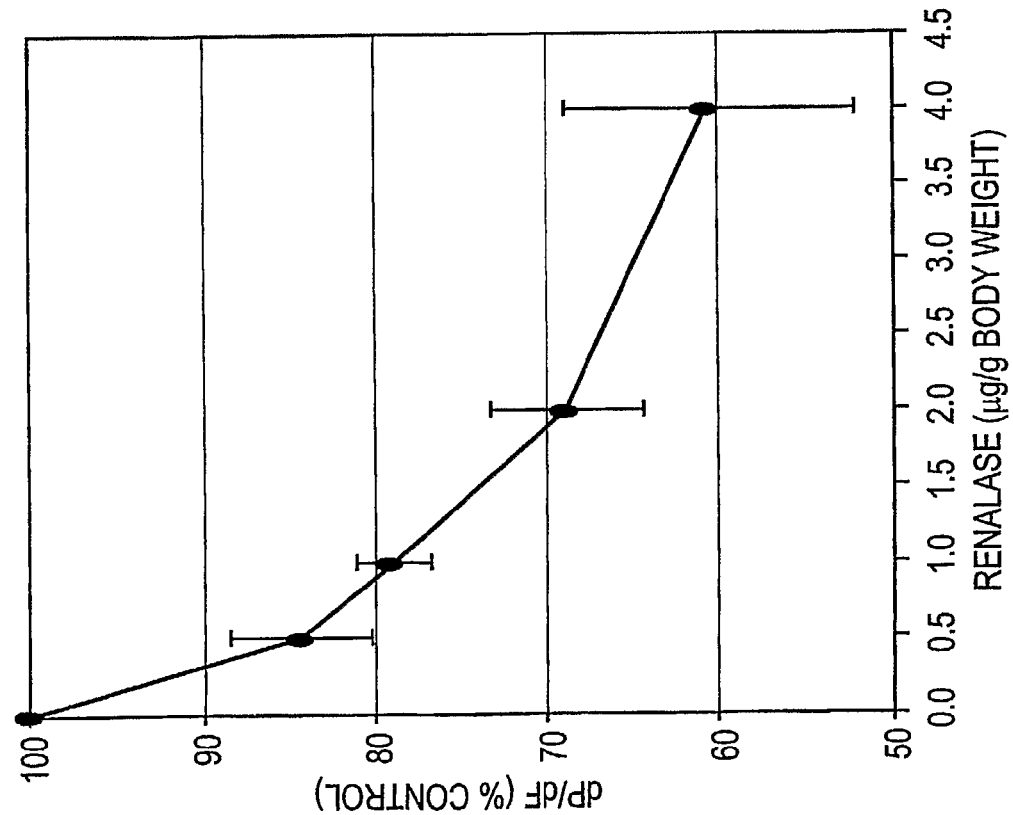
Figure 7G:
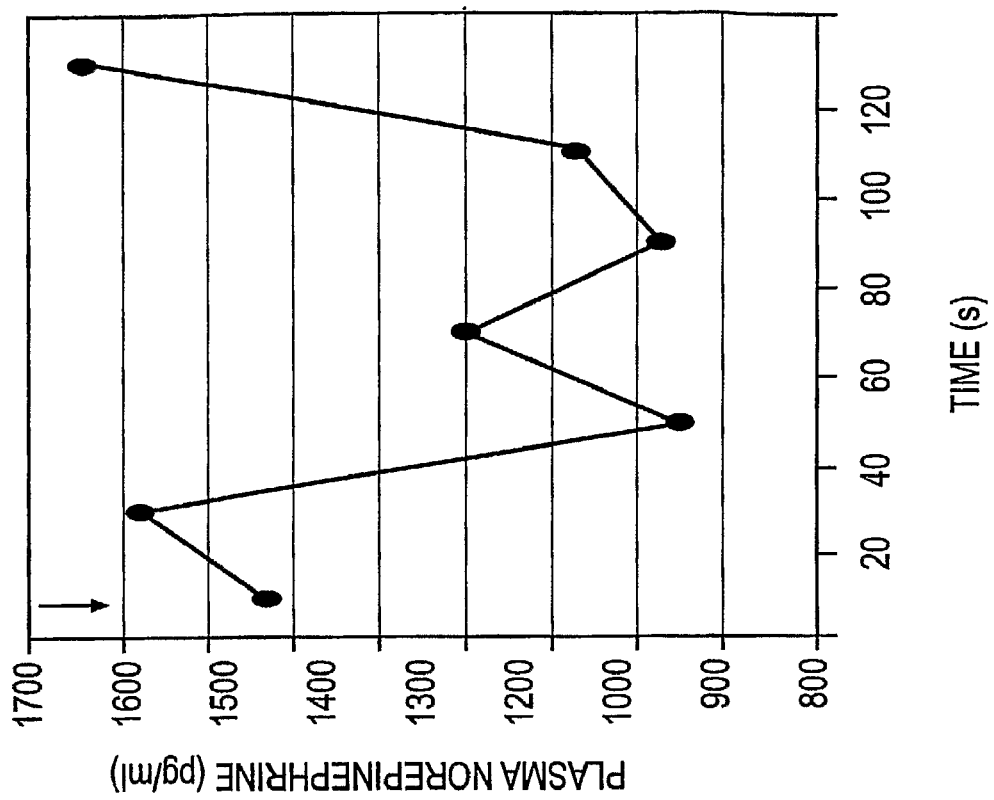
Figure 7F:
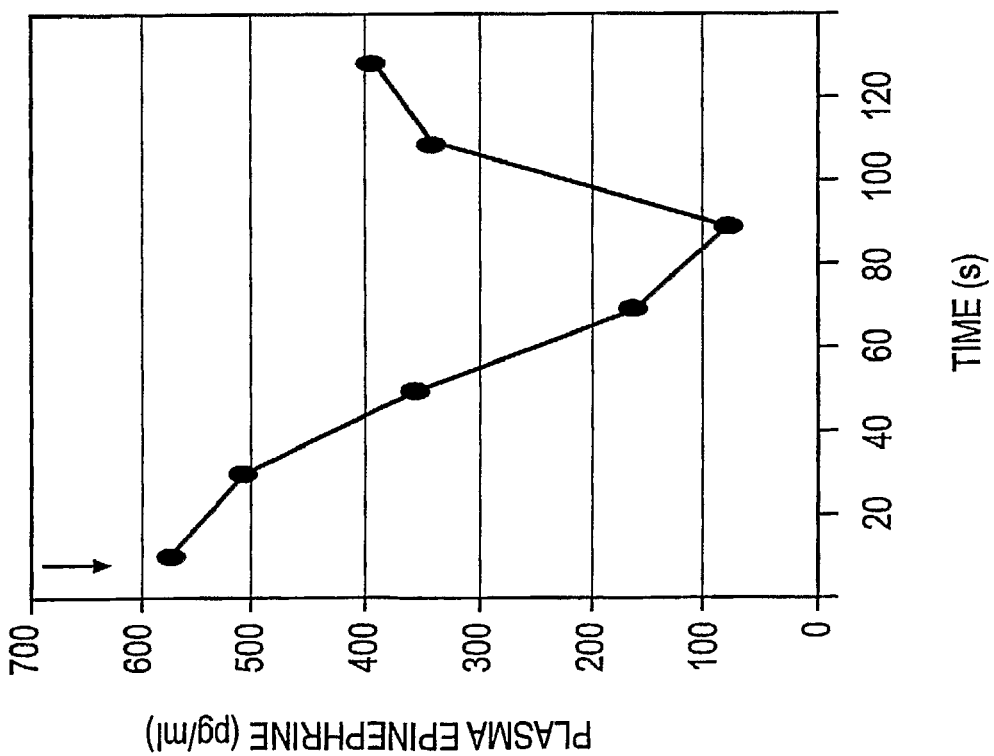

Blood pressure is a function of cardiac output and peripheral vascular resistance, and is regulated by the sympathetic nervous system. Circulating catecholamines control heart rate, myocardial contractility, and the tone of resistance vessels. Since renalase circulates in blood and degrades catecholamines, we examined its in vivo effect on hemodynamic parameters. Within 30 seconds of a single bolus intravenous injection of recombinant renalase, systolic, diastolic and mean arterial pressure decreased by 23.5±1.3, 32.6±2.9 and 28.9±2.7% respectively, (n=4, p<0.001). As shown in FIG. 7A (upper panel), blood pressure recovered within 2 minutes, and thereafter progressively decreased reaching a nadir (between 60-90 minutes) with systolic, diastolic and mean arterial pressures 16.5±1.5, 14.3±1.2, and 14.8±1.1% lower than baseline (n=4, p<0.01) (FIG. 7A, lower panel). Heart rate remained unchanged initially, and decreased slightly (6.4%) by 60 min, (FIG. 7A, lower panel). In control studies, blood pressure and heart rate were unaffected by either albumin or GST infusion (FIG. 7B). These data indicate that the hypotensive action of renalase is most likely the result of accelerated catecholamines degradation, which would prevent the expected rise in pulse rate (in response to hypotension), and would decrease myocardial contractility, and reduce vascular resistance. Alternatively, renalase could bind to a cognate receptor and modulate myocardial contractility and vascular resistance directly.

TABLE 1

|  | Control | Renalase | n | p |
| --- | --- | --- | --- | --- |
| Mean Arterial Pressure (mmHg) | 106.4 ± 4.7 | 65.3 ± 3.5 | 8 | <0.0001 |
| End systolic pressure (mmHg) | 127.7 ± 8.1 | 92.7 ± 2.7 | 5 | <0.004 |
| End diastolic pressure (mmHg) | 11.3 ± 1.8 | 9.3 ± 1.5 | 5 | NS |
| Heart rate (beats/min) | 342 ± 6 | 304 ± 9 | 5 | <0.004 |
| Cardiac Output (ml/min) | 45.8 ± 2.8 | 33.2 ± 1.5 | 3 | <0.03 |
| dP/dt (mmHg/sec) | 8604 ± 728 | 5235 ± 442 | 5 | <0.001 |
| Arterial elastance (mmHg/uL) | 0.94 ± 0.09 | 0.8 ± 0.04 | 3 | NS |
| Systemic vascular resistance (mmHg/L/min) | 2323 ± 196 | 1966 ± 183 | 3 | NS |

Example 5

Animal Models

Rat Remnant Kidney Model (RRKM)

A rat partial (5/6) nephrectomy or rat remnant kidney model can be used as described (Wada, M et al; J Clin Invest 1997 Dec. 15; 100(12):2977-83). Male rats (2-3 months old, weighing about 150-200 g) are subjected to unilateral nephrectomy (either left or right kidney) first. A 2.0 cm skin incision is made in the ventral midline, with its cranial terminus 1.0 cm caudal to the xyphoid process. A 2.0 cm muscle incision is made along the midline. The right kidney is isolated and cleared of surrounding fat and connective tissue to clearly view the renal artery and vein, and ureter as they enter the hilus of the kidney. Care is exercised to minimize disturbance of the adrenal gland. A ligature (3/0 silk) is placed around the renal artery, vein and ureter. These vessels are then cut proximal to the kidney and the kidney is removed, taking care that the adrenal gland is not disturbed. The second step of the surgical procedure involves the removal of the 2/3 of the remaining kidney in 7-10 days after the first step. Plasma creatinine (Cr) and BUN levels rise dramatically due to the loss of renal mass and function. Over the next several weeks, plasma Cr and BUN levels of surviving animals decline somewhat toward normal values but remain elevated. Renal function then appears to remain relatively constant or stable for a period of variable duration. After this point, the animals enter a period of chronic renal failure in which there is an essentially linear decline in renal function until death.

As surgical controls, age, weight-matched rats are subjected to a "sham" operation in which the kidneys are decapsulated but no renal tissue is removed.

Intervention Model for Chronic Renal Failure

In this model, both nephrectomized and sham-operated rats are maintained for approximately 5-6 months after surgery. At this point, surviving nephrectomized animals will enter chronic renal failure phase.

Rats are divided into 8 groups with 15 rats in each group. Two groups of nephrectomized rats are used as controls (Nx controls), with one of those groups receiving no treatment at all, while the other received injections of only the vehicle buffer. In addition, two groups of sham-operated rats were used as controls (sham controls), with one group receiving only the vehicle buffer, while the other received soluble renalase at 100 microgram/kg body weight. Four experimental groups of nephrectomized rats are also employed, receiving renalase at 10, 100, 500 microgram/kg body weight by SQ injection. Renalase treated and vehicle-only rats receive twice injection per day for 4-8 weeks.

Plasma BUN, Cr will be examined before and during the course of renalase treatment in all groups. It is expected that renalase will offer treatment benefit to Nx rats (slow down chronic renal failure progression). Histological studies will also be carried out the end of renalase treatment to examine the incidence of glomerular sclerosis, tubular collapse, interstitial sclerosis and microaneurysms.

Prophylactic Model for Chronic Renal Failure

In order to test the ability of renalase (renal therapeutic agent) to prevent, inhibit or delay the initiation of chronic renal failure, rats are subjected to partial nephrectomies or sham-operated as described above. The rats are allowed to recover for approximately two weeks after the second step of surgery before initiation of renalase therapy. At this point, surviving animals are past the acute renal failure phase and have not yet entered chronic renal failure. Rats are divided into two groups of 12 rats. One group receives only vehicle buffer (Nx control) whereas the other receives renalase treatment at 100 mircrogram/kg body weight given SQ twice per day. Administration of renalase or vehicle continued for a period of approximately 8-9 weeks.

Plasma BUN, Cr will be examined before and during the course of renalase injection in all groups. It is expected that renalase will prevent, inhibit or delay the initiation of chronic renal failure. Histological studies will also be carried out the end of renalase treatment to examine the incidence of glomerular sclerosis, tubular collapse, interstitial sclerosis and microaneurysms.

Hypertensive Model

The spontaneously hypertensive outbred rats (SHR) is generally used for studies in essential hypertension and cardiovascular research. Males, twelve weeks of age or older, dependably exhibit average systolic blood pressures greater than 200 mmHg. The anti-hypertensive effect of renalase can be tested in SHR.

SHR Rats are divided into two groups of 12 rats. One group receives only vehicle buffer whereas the other receives renalase treatment at 100 mircrogram/kg body weight given SQ twice per day. Administration of renalase or vehicle continued for a period of approximately 2-6 weeks. Rat blood pressure will be examined everyday by implantable telemetry device.

Congestive Heart Failure Model

Congestive heart failure (CHF) models are well described in the literatures, including large and small animals. One can use these models to test the prophylactic and therapeutic effect of renalase. For example, As described by Delehanty et al (Delehanty J M et al., Am J. Physiol. 1994 March; 266 (3 Pt 2): H930-5), one can use the rapid ventricular pacing model to induce CHF in canines (i.e., dogs). Dogs subjected to pacing at 225 beats/min for 8 wk developed heart failure as evidenced by elevated left atrial pressure, depressed first derivative of left ventricular pressure with respect to time, and depressed cardiac output compared with dogs paced at 100 beats/min for 8 wk. Fast-paced dogs also exhibited an elevated plasma NE and reduced myocardial NE content.

Other CHF animal models can be used as well. For example, male Sprague-Dawley (SD) rats are subjected to left coronary arterial ligation as described previously (Greenen, D. L. et al., J. Appl. Physiol. 63:92-96 (1987); Buttrick, P. et al., Am. J. Physiol. 260:11473-11479 (1991)) to induce myocardial infarction. The rats are anesthetized with sodium pentobarbital (60) mg/kg, ip), intubated via tracheotomy, and ventilated by a respirator. After a left-sided thoracotomy, the left coronary artery is ligated approximately 2 mm from its origin with a 7-0 silk suture. Sham animals undergo the same procedure except that the suture is passed under the coronary artery and then removed. In 4-6 weeks after ligation myocardial infarction can develop heart failure in rats. In clinical patients, myocardial infarction or coronary artery disease is the most common cause of heart failure. Congestive heart failure in this model reasonably mimics congestive heart failure in most human patients.

Stroke (Cerebral Vascular Accident) Model

A "stroke" is a sudden loss of function caused by an abnormality in the blood supply to the brain. Stroke presents with different levels of severity ranging from "transient ischemic attack" or "TIA" (no permanent disability), to "partial non-progressing stroke", to "complete stroke" (permanent, calamitous neurological deficit).

Stroke-prone spontaneously hypertensive (SHR-SP) rat are commonly used for stroke model. This experiment can be used to test for the possible beneficial effect(s) of renalase in stroke prevention/treatment. Male 8-week old SHR-SP rats are divided in random order into 2 groups. Control rats are maintained on ordinary chow and water containing 1% NaCl as drinking solution, control group receive vehicle injection. The treatment group receives renalase injection SQ (100 microgram/kg, twice daily) for 4-8 weeks. Systolic blood pressure will be measured by tail-cuff method in conscious animals, the stroke rate will be examined using magnetic resonance imaging (MRI), histopathology, and neurobehavioral testing in these two groups.

Arthrosclerosis Model

It is known that catecholamines cause vascular injury and, in the presence of hyperlipidaemia, cause accelerated and aggravated atherosclerosis (Kukreja R S et al, Atherosclerosis. (1981) 40 (3-4): 291-8.). Therefore, renalase may prevent/treat atherosclerosis. As described by Kukreja et al (Kukreja R S et al, Atherosclerosis. 1981 November-December; 40(3-4):291-8.), advanced aortic and coronary atherosclerosis can be produced in rhesus monkeys by means of two procedures: (a) high fat and cholesterol feeding for 7 months, and (b) this diet coupled with daily i.v. injection of adrenaline (50 micrograms/kg body weight). Monkeys subjected to procedure (b) will develop markedly advanced atherosclerosis in the form of fibrous plaques in the aorta and coronary artery, while these lesions are expected to be much less frequent in the other group. The ratio of total to free serum cholesterol will be significantly increased and the aortic cholesterol content will be very high in monkeys subjected to both the atherogenic diet and adrenaline injections. These models can be used to test the effect of renalase on atherosclerosis prevention and treatment.

A second model for testing renalase involves apoE knockout mice (Zhang S H, Reddick R L, Piedrahita J A, Maeda N., (1992) Spontaneous hypercholesterolemia and arterial lesions in mice lacking apolipoprotein E, Science, 258, 468-471). The apoe knockout mouse was created by gene targeting in embryonic stem cells to disrupt the apoe gene. ApoE, a glycoprotein, is a structural component of very low density lipoprotein (VLDL) synthesized by the liver and intestinally synthesized chylomicrons. It is also a constituent of a subclass of high density lipoproteins (HDLs) involved in cholesterol transport activity among cells. One of the most important roles of apoe is to mediate high affinity binding of chylomicrons and VLDL particles that contain apoe to the low density lipoprotein (LDL) receptor. This allows for the specific uptake of these particles by the liver which is necessary for transport preventing the accumulation in plasma of cholesterol rich remnants. The homozygous inactivation of the apoE gene results in animals that are devoid of apoE in their sera. The mice appear to develop normally however they exhibit five times the normal serum plasma cholesterol and spontaneous atherosclerotic lesions. This is similar to a disease in people who have a variant form of the apoe gene that is defective in binding to the LDL receptor and are at risk for early development of atherosclerosis, and increased plasma triglyceride and cholesterol levels. The apoe knockout mice are widely used to as atherosclerosis model to investigate intervention therapies that modify the atherogenic process and can be used herein for testing the effects of such therapies using renalase.

Example 6

Further Studies

In addition to the foregoing examples, studies have been planned or being conducted by the present inventors. One study involves clinical assessment of the correlation of renalase levels with kidney function in about 300 subjects. 70 people have been enrolled so far. Preliminary results will be available in about 6-7 weeks. In another study, the inventors will evaluate the effect of chronic renalase administration by subcutaneous injection on the progression of chronic kidney disease and the development of cardiovascular complications in a rat model of chronic renal failure. In yet another study, the inventors will evaluate the efficacy of intramuscular injections of a CMV-renalase vector in the rat model.

Discussion

The renalase identified herein is the third monoamine oxidase in human using functional genomic database. Similar to MAO-A and MAO-B, renalase metabolizes catecholamines such as dopamine (DA), norepinephrine (NA), and epinephrine (EP). Renalase has several important, unique features that differentiate it from MAO-A and MAO-B. First, compared to MAO-A and MAO-B, renalase is predominantly expressed in the kidney, suggesting that renalase has a unique role in catecholamine metabolism in the periphery. It is believed that the metabolism of circulatory monoamines are carried out by a host of intracellular enzymes (Eisenhofer et al., 2001), including MAO-A, MAO-B, catechol-O-methyltransferase (COMT) and sulfotransferase. Since these enzymes have intracellular locations, the primary mechanism limiting the lifespan of circulatory catecholamine is uptake by active transport into cells, not metabolism by enzymes. This is consistent with the notion that the primary role of MAO-A and MAO-B lies in the metabolism of amines and in the regulation of neurotransmitter levels and intracellular amine stores.

Second, unlike MAO-A and MAO-B that are located in the outer membrane of mitochondrion, renalase is a secretory protein, suggesting catecholamine clearance can take place in the extracellular space, challenging the traditional thinking that catecholamines have to be taken up by the cells in order to be catabolized. It is circulating in the blood where renalase catabolizes serum catecholamine. It is possible that renalase "fine-tunes" the plasma catecholamine level from minute-to-minute.

Third, renalase is highly expressed in the kidney, suggesting the kidney is involved in catecholamine degradation via the renalase catalytic pathway. The data provided herein is consistent with the hypothesis that renalase regulates catecholamine at the systemic level as well as at local kidney level. It is conceivable that renalase, in conjunction with MAO-A and MAO-B that catabolize intracellular amines, is an important enzyme to oxidase extracellular catecholamine, and thus contributing to the regulation of overall sympathetic tone.

Renalase is most abundant in the proximal tubules and it presents in the circulation of normal individuals, suggesting that renalase protein in the proximal tubules can be secreted via the basolateral membrane into the circulation where it catabolized its substrate(s), and thus, regulating catecholamine homeostasis at a systemic level.

It is possible that renalase also exerts its biological function at the lumen of renal tubules, since renalase is small protein which can be easily filtered to the lumen of nephron. In addition, renalase can be directly secreted via the apical membrane by the proximal tubules, where it metabolize its substrate(s) that filtered through the glomeurli and generated de novo by the renal tubular cells such as dopamine (Wang et al., 2001). The significance of renalase in catecholamine metabolism at intra-lumen is to regulate intra-lumen catecholamine level, thus regulating salt and water re-absorption.

Recent studies have shown that plasma dopamine (Cuche et al., 1986; Prinseau et al., 1986) and norepinephrine (Zoccalie et al., 2002) is consistently elevated in patients with ESRD. Those changes of catecholamine levels are important contributors to the pathogenesis of cardiovascular diseases such as asymptomatic left ventricular dysfunction (Benedict et al., 1996), chronic congestive heart failure (Rouleau et al., 1994) and atherosclerosis (Rozanski et al., 1999). The importance of high sympathetic tone in cardiovascular complications is also supported by intervention studies (Tendera et al., 2001). In patients with ESRD, increased circulating catecholamines might render uremic patients susceptible to a series of cardiovascular complications ranging from left ventricular hypertrophy to arrhythmia (Zoccali et al., 2002). The mechanism of elevated catecholamine in ESRD patients remains poorly understood. Our discovery of renalase (which catabolizes catecholamines and is highly expressed in the kidney) may explain the pathogenesis of catecholamine derangement in those patients as they lose renal mass (similar to reduced erythropoetin secretion in ESRD patients).

It is not surprising to see a dramatically reduced renalase in patients with ESRD since renalase is mostly expressed in the kidney, an organ that ESRD patients have lost its function. The fact that renalase catabolize catecholamine, coupled with elevated catecholamine level in ESRD patients, strongly suggest renalase is a critical protein in maintaining catecholamine homeostasis, and MAO-C is the missing factor that contributes to catecholamine derangement leading to hypertension, cardiovascular diseases such as asymptomatic left ventricular dysfunction, chronic congestive heart failure and atherosclerosis.

The foregoing detailed description has been given for clearness of understanding only and no unnecessary limitations should be understood therefrom as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

The disclosures for each and every patent, patent application, and public cited herein including but not limited to the references listed immediately below are hereby incorporated by reference in their entirety.
1. Brenner, B. M., Deen, W. M. & Robertson, C. R. Determinants of glomerular filtration rate. Annu Rev Physiol 38, 11-19 (1976).
2. Lin, F. K. et al. Cloning and expression of the human erythropoietin gene. Proc Natl Acad Sci USA 82, 7580-4 (1985).
3. Jacobs, K. et al. Isolation and characterization of genomic and cDNA clones of human erythropoietin. Nature 313, 806-10 (1985).
4. Humes, H. D. Acute renal failure: prevailing challenges and prospects for the future. Kidney Int Suppl 50, S26-32 (1995).
5. Wolfe, R. A. et al. Comparison of mortality in all patients on dialysis, patients on dialysis awaiting transplantation, and recipients of a first cadaveric transplant. N Engl J Med 341, 1725-30 (1999).
6. Oberg, B. P. et al. Increased prevalence of oxidant stress and inflammation in patients with moderate to severe chronic kidney disease. Kidney Int 65, 1009-16 (2004).
7. Koomans, H. A., Blankestijn, P. J. & Joles, J. A. Sympathetic hyperactivity in chronic renal failure: a wake-up call. J Am Soc Nephrol 15, 524-37 (2004).
8. Joles, J. A. & Koomans, H. A. Causes and consequences of increased sympathetic activity in renal disease. Hypertension 43, 699-706 (2004).
9. Strausberg, R. L., Feingold, E. A., Klausner, R. D. & Collins, F. S. The mammalian gene collection. Science 286, 455-7 (1999).
10. Binda, C., Mattevi, A. & Edmondson, D. E. Structure-function relationships in flavoenzyme-dependent amine 10. oxidations: a comparison of polyamine oxidase and monoamine oxidase. J Biol Chem 277, 23973-6 (2002).
11. Jalkanen, S. & Salmi, M. Cell surface monoamine oxidases: enzymes in search of a function. Embo J 20, 3893-901 (2001).
12. Binda, C., Newton-Vinson, P., Hubalek, F., Edmondson, D. E. & Mattevi, A. Structure of human monoamine oxidase B, a drug target for the treatment of neurological disorders. Nat Struct Biol 9, 22-6 (2002).
13. Liang, X. et al. Transcriptionally active polymerase chain reaction (TAP): high throughput gene expression using genome sequence data. J Biol Chem 277, 3593-8 (2002).
14. Salmi, M. & Jalkanen, S. VAP-1: an adhesin and an enzyme. Trends Immunol 22, 211-6 (2001).
15. Zoccali, C. et al. Norepinephrine and concentric hypertrophy in patients with end-stage renal disease. Hypertension 40, 41-6 (2002).
16. Zoccali, C. et al. Plasma norepinephrine predicts survival and incident cardiovascular events in patients with end-stage renal disease. Circulation 105, 1354-9 (2002).
17. Hausberg, M. et al. Sympathetic nerve activity in end-stage renal disease. Circulation 106, 1974-9 (2002).
18. Tian, S. et al. Regulation of the voltage-gated K(+) channel KCNA10 by KCNA4B, a novel beta-subunit. Am J Physiol Renal Physiol 283, F142-9. (2002).
19. Yao, X., Tian, S., Chan, H.-Y., Biemesderfer, D. & Desir, G. Expression of KCNA10, a voltage-gated K channel, in glomerular endothelium and at the apical membrane of the renal proximal tubule. J Am Soc Nephrol 13, 2831-2839 (2002).
20. Massey, V. (2000) The chemical and biological versatility of riboflavin. *Biochem. Soc. Trans.* 28, 283-296.
21. Weyler, W., Hsu, Y. P., and Breakfield, X. (1990) Biochemistry and genetics of monoamine oxidase. *Pharmacol. Ther.* 47, 391-417 12.
22. Shih, J. C., Chen, K., and Ridd, M. J. (1999) Monoamine oxidase: from genes to behavior. *Annu. Rev. Neurosci.* 22, 197-217.
23. Cesura, A. M., and Pletscher, A. (1992) The new generation of monoamine oxidase inhibitors. *Prog. Drug Res.* 38, 171-297.
24. Kearney, E. B., Salach, J. I., Walker, W. H., Seng, R. L., Kenney, W., Zeszotek, E., and Singer, T. P. (1971) The covalently-bound flavin of hepatic monoamine oxidase. 1. Isolation and sequence of a flavin peptide and evidence for binding at the 8alpha position. *Eur. J. Biochem.* 24, 321-327.
25. Xiaowu Liang, Andy Teng, Dawn M. Braun, Jiin Felgner, Yan Wang, Scott I. Baker, Shizong Chen, Olivier Zelphati, and Philip L. Felgner. Transcriptionally Active Polymerase Chain Reaction (TAP) J. Biol. Chem., 277:3593-3598. (2002).
26. Yao X, Tian S, Chan H Y, Biemesderfer D, Desir G V. Expression of KCNA10, a Voltage-Gated K Channel, in Glomerular Endothelium and at the Apical Membrane of the Renal Proximal Tubule. J Am Soc Nephrol. (2002) 13(12):2831-9.
27. Strausberg, R. L., Feingold, E. A., Klausner, R. D., & Collins, F. S. The mammalian gene collection. Science 286, 455-457. (1999).
28. Stroud, R. M., and Walter, P. (1999) Signal sequence recognition and protein targeting. Curr. Opin. Struct. Biol. 9, 754-759.
29. Henrik Nielsen and Anders Krogh: Prediction of signal peptides and signal anchors by a hidden Markov model. In Proceedings of the Sixth International Conference on Intelligent Systems for Molecular Biology (ISMB 6), AAAI Press, Menlo Park, Calif., pp. 122-130 (1998).
30. Falquet L, Pagni M, Bucher P, Hulo N, Sigrist C J, Hofinann K & Bairoch A. (2002) The PROSITE database, its status in 2002. Nucleic Acids Res. 30:235-238.
31. Eisenhofer G, Huynh T T, Hiroi M, Pacak K. Understanding catecholamine metabolism as a guide to the biochemical diagnosis of pheochromocytoma Rev Endocr Metab Disord. 2001 August; 2(3):297-311.
32. Zoccali C, Mallamaci F, Parlongo S, Cutrupi S, Benedetto F A, Tripepi G, Bonanno G, Rapisarda F, Fatuzzo P, Seminara G, Cataliotti A, Stancanelli B, Malatino L S, Cateliotti A. Plasma norepinephrine predicts survival and incident cardiovascular events in patients with end-stage renal disease. Circulation 2002 19; 105(11):1354-9.
33. Benedict C R, Shelton B, Johnstone D E, et al, for the SOLVD Investigators. Prognostic significance of plasma norepinephrine in patients with asymptomatic left ventricular dysfunction. Circulation. 1996; 94: 690-697.
34. Rouleau J L, Packer M, Moye L, et al. Prognostic value of neurohormonal activation in patients with an acute myocardial infarction: effect of captopril. J Am Coll Cardiol. 1994; 24: 583-591.
35. Rozanski A, Blumenthal J A. Kaplan J. Impact of psychological factors on the pathogenesis of cardiovascular disease and implications for therapy. Circulation. (1999) 99: 2192-2217.
36. Tendera M, Ochala A. Overview of the results of recent beta blocker trials. Curr Opin Cardiol. (2001) 16: 180-185.
37. Graham F L, Smiley J, Russell W C, Nairn R. Characteristics of a human cell line transformed by DNA from humanadenovirus type 5. J Gen Virol 1977 36(1):59-74.
38. Wang Y, Berndt T J, Gross J M, Peterson M A, So M J, Knox F G. Effect of inhibition of MAO and COMT on intrarenal dopamine and serotonin and on renal function. Am J Physiol Regul Integr Comp Physiol. 2001 280(1): R248-54.
39. Excerpts from United States Renal Data System. Annual Data Report. Am. J. Kidney Dis. 32 (suppl 1), 569-580. (1998).
40. Humes, H. D. Acute renal failure: prevailing challenges and prospects for the future. Kidney Int. 48, S-26-S-32. (1995).
41. Wolfe, R., V. Ashby, E. Milford, et al. Comparison of mortality in all patients on dialysis, patients on dialysis N Engl. J. Med. 341:1725-1730. (1999).
42. Yagi, N. & Paganini E. P. Acute dialysis and continuous renal replacement: the emergence of new technology involving the nephrologist in the intensive care setting. Semin. Nephrol. 17, 306-320. (1997).
43. Mehta, R. L. Therapeutic alternatives to renal replacement for critically ill patients in acute renal failure. Semin. Nephrol. 14, 64-82. (1994).
44. Zarowitz, B. J., Anandan, J. V., Dumler, F., Jayashankar, J. & Levin, N. Continuous arteriovenous hemofiltration of aminoglycoside antibiotics in critically ill patients. J. Clin. Pharm. 26, 686-689. (1986).
45. Jacobs K, Shoemaker C, Rudersdorf R, Neill S D, Kaufman R J, Mufson A, Seehra J, Jones S S, Hewick R, Fritsch E F, et al. Isolation and characterization of genomic and cDNA clones of human erythropoietin. Nature 313:806-10. (1985).
46. Lin F K, Suggs S, Lin C H, Browne J K, Smalling R, Egrie J C, Chen K K, Fox G M, Martin F, Stabinsky Z, et al. Cloning and expression of the human erythropoietin gene. Proc Natl Acad Sci USA. 82(22):7580-4. (1985).

47. Frangioni, J. V. and Neel, B. G., Solubilization and purification of enzymatically active glutathione S-transferase (PGEX) fusion proteins. Anal. Biochem. 210, 179-187 (1993).
48. Zhuang Z, Hogan M, McCauley R. The in vitro insertion of monoamine oxidase B into mitochondrial outer membranes. *FEBS Lett* 238:185-190. (1988).
49. Cuche J L, Prinseau J, Selz F, Ruget G, Baglin A. Plasma free, sulfo- and glucuro-conjugated catecholamines in uremic patients. Kidney Int. 30(4):566-72. (1986).
50. Prinseau J, Ruget G, Selz F, Baglin A, Fritel D, Cuche J L. Plasma catecholamines, free and conjugated, in the hemodialyzed chronic renal failure patient. Arch Mal Coeur Vaiss. 79(6):835-9. (1986).
51. Zoccali C, Mallamaci F, Parlongo S, Cutrupi S, Benedetto F A, Tripepi G, Bonanno G, Rapisarda F, Fatuzzo P, Seminara G, Cataliotti A, Stancanelli B, Malatino L S, Cateliotti A. Plasma norepinephrine predicts survival and incident cardiovascular events in patients with end-stage renal disease. Circulation 19; 105(11):1354-9. (2002).
52. Benedict C R, Shelton B, Johnstone D E, et al, for the SOLVD Investigators. Prognostic significance of plasma norepinephrine in patients with asymptomatic left ventricular dysfunction. Circulation. 94: 690-697. (1996).
53. Rouleau J L, Packer M, Moye L, et al. Prognostic value of neurohormonal activation in patients with an acute myocardial infarction: effect of captopril. J Am Coll Cardiol. 24: 583-591. (1994).
54. Rozanski A, Blumenthal J A. Kaplan J. Impact of psychological factors on the pathogenesis of cardiovascular disease and implications for therapy. Circulation. 99: 2192-2217. (1999).
55. Tendera M, Ochala A. Overview of the results of recent beta blocker trials. Curr Opin Cardiol. 16: 180-185. (2001).

The invention claimed is:

1. A method for treating or ameliorating chronic renal insufficiency in a mammal comprising: administering to said mammal a therapeutically effective amount of a polypeptide that comprises an amino acid sequence having at least 95% sequence identity with SEQ ID NO: 2.

2. The method of claim 1, wherein the polypeptide metabolizes dopamine, epinephrine, and norepinephrine.

3. The method of claim 1, wherein the polypeptide comprises an amino acid sequence having at least 98% sequence identity with SEQ ID NO: 2.

4. The method of claim 1, wherein the polypeptide comprises the amino acid sequence of SEQ ID NO: 2.

5. The method of claim 1, wherein the polypeptide comprises amino acid residues 17-342 of SEQ ID NO:2.

6. The method of claim 1, wherein the polypeptide binds flavin adenine dinucleotide (FAD) cofactor.

7. The method of claim 1, wherein the polypeptide is administered as a parenteral formulation.

8. The method of claim 1, wherein the mammal has end-stage renal disease.

9. The method of claim 1, wherein the mammal has one or more cardiovascular conditions selected from hypertension, atherosclerosis, and chronic congestive heart failure.

10. The method of claim 1, wherein the mammal has reduced levels of endogenous circulating renalase.

11. The method of claim 1, wherein the mammal is a human.

12. A method for treating or ameliorating a cardiovascular condition associated with chronic renal failure in a mammal, the method comprising: administering to said mammal a therapeutically effective amount of a polypeptide that comprises an amino acid sequence having at least 95% sequence identity with SEQ ID NO: 2.

13. The method of claim 12, wherein the cardiovascular condition is one or more of hypertension, atherosclerosis, and chronic congestive heart failure.

14. The method of claim 12, wherein the polypeptide comprises an amino acid sequence having at least 98% sequence identity with SEQ ID NO: 2.

15. The method of claim 12, wherein the polypeptide comprises the amino acid sequence of SEQ ID NO: 2.

16. A method for treating or ameliorating a cardiovascular condition associated with chronic renal failure in a mammal, the method comprising: administering to said mammal a therapeutically effective amount of renalase, said renalase comprising an amino acid sequence that has at least 90% sequence identity to SEQ ID NO: 2, and is encoded by a polynucleotide comprising exons 1, 2, 3, 4, 5, and 6 of SEQ ID NO:1 or SEQ ID NO:3.

17. The method of claim 16, wherein the amino acid sequence is encoded by SEQ ID NO:1.

18. The method of claim 16, wherein the amino acid sequence is encoded by SEQ ID NO:3.

* * * * *

UNITED STATES PATENT AND TRADEMARK OFFICE
CERTIFICATE OF CORRECTION

| | | |
|---|---|---|
| PATENT NO. | : 7,700,095 B2 | Page 1 of 1 |
| APPLICATION NO. | : 10/593099 | |
| DATED | : April 20, 2010 | |
| INVENTOR(S) | : Jianchao Xu et al. | |

It is certified that error appears in the above-identified patent and that said Letters Patent is hereby corrected as shown below:

In the Specification

Column 1, lines 18-21 (Statement Regarding Federally Sponsored Research or Development), replace:

"This invention was supported in part by funds obtained from the U.S. Government (National Institutes of Health Grant Number K08 DK 0291702), and the U.S. Government may therefore have certain rights in the invention."

With the following:

--This invention was made with government support under DK002917, DK086465 and DK081037 awarded by National Institute of Health. The government has certain rights in the invention.--

Signed and Sealed this
Third Day of June, 2014

Michelle K. Lee
*Deputy Director of the United States Patent and Trademark Office*

SEQUENCE LISTING

```
<160> NUMBER OF SEQ ID NOS: 13

<210> SEQ ID NO 1
<211> LENGTH: 1477
<212> TYPE: DNA
<213> ORGANISM: Homo sapiens
<220> FEATURE:
<221> NAME/KEY: CDS
<222> LOCATION: (24)..(1052)

<400> SEQUENCE: 1
gcggatcgct gctccctctc gcc atg gcg cag gtg ctg atc gtg ggc gcc ggg        53
                         Met Ala Gln Val Leu Ile Val Gly Ala Gly
                          1               5                  10 atg aca gga agc ttg tgc gct gcg ctg ctg agg agg cag acg tcc ggt         101
Met Thr Gly Ser Leu Cys Ala Ala Leu Leu Arg Arg Gln Thr Ser Gly
             15                  20                  25 ccc ttg tac ctt gct gtg tgg gac aag gct gac gac tca ggg gga aga         149
Pro Leu Tyr Leu Ala Val Trp Asp Lys Ala Asp Asp Ser Gly Gly Arg
         30                  35                  40 atg act aca gcc tgc agt cct cat aat cct cag tgc aca gct gac ttg         197
Met Thr Thr Ala Cys Ser Pro His Asn Pro Gln Cys Thr Ala Asp Leu
     45                  50                  55 ggt gct cag tac atc acc tgc act cct cat tat gcc aaa aaa cac caa         245
Gly Ala Gln Tyr Ile Thr Cys Thr Pro His Tyr Ala Lys Lys His Gln
 60                  65                  70 cgt ttt tat gat gaa ctg tta gcc tat ggc gtt ttg agg cct cta agc         293
Arg Phe Tyr Asp Glu Leu Leu Ala Tyr Gly Val Leu Arg Pro Leu Ser
75                  80                  85                  90 tcg cct att gaa gga atg gtg atg aaa gaa gga gac tgt aac ttt gtg         341
Ser Pro Ile Glu Gly Met Val Met Lys Glu Gly Asp Cys Asn Phe Val
                 95                 100                 105 gca cct caa gga att tct tca att att aag cat tac ttg aaa gaa tca         389
Ala Pro Gln Gly Ile Ser Ser Ile Ile Lys His Tyr Leu Lys Glu Ser
             110                 115                 120 ggt gca gaa gtc tac ttc aga cat cgt gtg aca cag atc aac cta aga         437
Gly Ala Glu Val Tyr Phe Arg His Arg Val Thr Gln Ile Asn Leu Arg
         125                 130                 135 gat gac aaa tgg gaa gta tcc aaa caa aca ggc tcc cct gag cag ttt         485
Asp Asp Lys Trp Glu Val Ser Lys Gln Thr Gly Ser Pro Glu Gln Phe
     140                 145                 150
```

-continued

```
gat ctt att gtt ctc aca atg cca gtt cct gag att ctg cag ctt caa      533
Asp Leu Ile Val Leu Thr Met Pro Val Pro Glu Ile Leu Gln Leu Gln
155                 160                 165                 170 ggt gac atc acc acc tta att agt gaa tgc caa agg cag caa ctg gag      581
Gly Asp Ile Thr Thr Leu Ile Ser Glu Cys Gln Arg Gln Gln Leu Glu
                175                 180                 185 gct gtg agc tac tcc tct cga tat gct ctg ggc ctc ttt tat gaa gct      629
Ala Val Ser Tyr Ser Ser Arg Tyr Ala Leu Gly Leu Phe Tyr Glu Ala
            190                 195                 200 ggt acg aag att gat gtc cct tgg gct ggg cag tac atc acc agt aat      677
Gly Thr Lys Ile Asp Val Pro Trp Ala Gly Gln Tyr Ile Thr Ser Asn
        205                 210                 215 ccc tgc ata cgc ttc gtc tcc att gat aat aag aag cgc aat ata gag      725
Pro Cys Ile Arg Phe Val Ser Ile Asp Asn Lys Lys Arg Asn Ile Glu
    220                 225                 230 tca tca gaa att ggg cct tcc ctc gtg att cac acc act gtc cca ttt      773
Ser Ser Glu Ile Gly Pro Ser Leu Val Ile His Thr Thr Val Pro Phe
235                 240                 245                 250 gga gtt aca tac ttg gaa cac agc att gag gat gtg caa gag tta gtc      821
Gly Val Thr Tyr Leu Glu His Ser Ile Glu Asp Val Gln Glu Leu Val
                255                 260                 265 ttc cag cag ctg gaa aac att ttg ccg ggt ttg cct cag cca att gct      869
Phe Gln Gln Leu Glu Asn Ile Leu Pro Gly Leu Pro Gln Pro Ile Ala
            270                 275                 280 acc aaa tgc caa aaa tgg aga cat tca cag gtt aca aat gct gct gcc      917
Thr Lys Cys Gln Lys Trp Arg His Ser Gln Val Thr Asn Ala Ala Ala
        285                 290                 295 aac tgt cct ggc caa atg act ctg cat cac aaa cct ttc ctt gca tgt      965
Asn Cys Pro Gly Gln Met Thr Leu His His Lys Pro Phe Leu Ala Cys
    300                 305                 310 gga ggg gat gga ttt act cag tcc aac ttt gat ggc tgc atc act tct     1013
Gly Gly Asp Gly Phe Thr Gln Ser Asn Phe Asp Gly Cys Ile Thr Ser
315                 320                 325                 330 gcc cta tgt gtt ctg gaa gct tta aag aat tat att tag tgcctatatc      1062
Ala Leu Cys Val Leu Glu Ala Leu Lys Asn Tyr Ile
                335                 340 cttattctct atatgtgtat tgggttttta ttttcacaat tttctgttat tgattatttt   1122
gttttctatt ttgctaagaa aaattactgg aaaattgttc ttcacttatt atcatttttc   1182
atgtggagta taaaatcaat tttgtaattt tgatagttac aacccatgct agaatggaaa   1242
ttcctcacac cttgcacctt ccctactttt ctgaattgct atgactactc cttgttggag   1302
gaaaagtggt acttaaaaaa taacaaacga ctctctcaaa aaaattacat taaatcacaa   1362
taacagtttg tatgccaaaa acttgattat ccttatgaaa atttcaattc tgaataaaga   1422
ataatcacat tatcaaagcc ccatcaaaaa aaaaaaaaa aaaaaaaaaa aaaaa         1477

<210> SEQ ID NO 2
<211> LENGTH: 342
<212> TYPE: PRT
<213> ORGANISM: Homo sapiens

<400> SEQUENCE: 2

Met Ala Gln Val Leu Ile Val Gly Ala Gly Met Thr Gly Ser Leu Cys
1               5                   10                  15

Ala Ala Leu Leu Arg Arg Gln Thr Ser Gly Pro Leu Tyr Leu Ala Val
            20                  25                  30

Trp Asp Lys Ala Asp Asp Ser Gly Gly Arg Met Thr Thr Ala Cys Ser
        35                  40                  45
```

```
Pro His Asn Pro Gln Cys Thr Ala Asp Leu Gly Ala Gln Tyr Ile Thr
     50                  55                  60

Cys Thr Pro His Tyr Ala Lys Lys His Gln Arg Phe Tyr Asp Glu Leu
 65                  70                  75                  80

Leu Ala Tyr Gly Val Leu Arg Pro Leu Ser Ser Pro Ile Glu Gly Met
                 85                  90                  95

Val Met Lys Glu Gly Asp Cys Asn Phe Val Ala Pro Gln Gly Ile Ser
            100                 105                 110

Ser Ile Ile Lys His Tyr Leu Lys Glu Ser Gly Ala Glu Val Tyr Phe
            115                 120                 125

Arg His Arg Val Thr Gln Ile Asn Leu Arg Asp Asp Lys Trp Glu Val
    130                 135                 140

Ser Lys Gln Thr Gly Ser Pro Glu Gln Phe Asp Leu Ile Val Leu Thr
145                 150                 155                 160

Met Pro Val Pro Glu Ile Leu Gln Leu Gln Gly Asp Ile Thr Thr Leu
                165                 170                 175

Ile Ser Glu Cys Gln Arg Gln Leu Glu Ala Val Ser Tyr Ser Ser
            180                 185                 190

Arg Tyr Ala Leu Gly Leu Phe Tyr Glu Ala Gly Thr Lys Ile Asp Val
    195                 200                 205

Pro Trp Ala Gly Gln Tyr Ile Thr Ser Asn Pro Cys Ile Arg Phe Val
    210                 215                 220

Ser Ile Asp Asn Lys Lys Arg Asn Ile Glu Ser Ser Glu Ile Gly Pro
225                 230                 235                 240

Ser Leu Val Ile His Thr Val Pro Phe Gly Val Thr Tyr Leu Glu
                245                 250                 255

His Ser Ile Glu Asp Val Gln Glu Leu Val Phe Gln Gln Leu Glu Asn
            260                 265                 270

Ile Leu Pro Gly Leu Pro Gln Pro Ile Ala Thr Lys Cys Gln Lys Trp
    275                 280                 285

Arg His Ser Gln Val Thr Asn Ala Ala Ala Asn Cys Pro Gly Gln Met
    290                 295                 300

Thr Leu His His Lys Pro Phe Leu Ala Cys Gly Gly Asp Gly Phe Thr
305                 310                 315                 320

Gln Ser Asn Phe Asp Gly Cys Ile Thr Ser Ala Leu Cys Val Leu Glu
                325                 330                 335

Ala Leu Lys Asn Tyr Ile
            340

<210> SEQ ID NO 3
<211> LENGTH: 2107
<212> TYPE: DNA
<213> ORGANISM: Homo sapiens

<400> SEQUENCE: 3
aaaagcccgg gccgaacggc cccgccgcag agactcagcg cggatcgctg ctccctctcg    60
ccatggcgca ggtgctgatc gtgggcgccg ggatgacagg aagcttgtgc gctgcgctgc   120
tgaggaggca gacgtccggt cccttgtacc ttgctgtgtg ggacaaggct gaggactcag   180
ggggaagaat gactacagcc tgcagtcctc ataatcctca gtgcacagct gacttgggtg   240
ctcagtacat cacctgcact cctcattatg ccaaaaaaca ccaacgtttt tatgatgaac   300
tgttagccta tggcgttttg aggcctctaa gctcgcctat tgaaggaatg gtgatgaaag   360
aaggagactg taactttgtg gcacctcaag gaatttcttc aattattaag cattacttga   420
```

```
aagaatcagg tgcagaagtc tacttcagac atcgtgtgac acagatcaac ctaagagatg    480
acaaatggga agtatccaaa caaacaggct cccctgagca gtttgatctt attgttctca    540
caatgccagt tcctgagatt ctgcagcttc aaggtgacat caccacctta attagtgaat    600
gccaaaggca gcaactggag gctgtgagct actcctctcg atatgctctg ggcctctttt    660
atgaagctgg tacgaagatt gatgtccctt gggctgggca gtacatcacc agtaatccct    720
gcatacgctt cgtctccatt gataataaga agcgcaatat agagtcatca gaaattgggc    780
cttccctcgt gattcacacc actgtcccat ttggagttac atacttggaa cacagcattg    840
aggatgtgca agagttagtc ttccagcagc tggaaaacat tttgccgggt ttgcctcagc    900
caattgctac caaatgccaa aaatggagac attcacaggt accaagtgct ggtgtgattc    960
taggatgtgc gaagagcccc tggatgatgg cgattggatt tcccatctga cttcctggaa   1020
attggagcac acagtcaggt tttatttgat ttttttttt aaggatacca cttcacagcc   1080
tttaggatag ctattattta gaagcaaaac agaagataaa tgttggcaag gatgtggaga   1140
tattggattc ccttgtgcag tgccggtggg aatgtaaaat gatgtagcta ctatggaaaa   1200
tgatacggca atttctttag aaatgaaata tagaattgcc gtatgatctg cagttccaca   1260
tctggatatc tatccaaaag aagtgaaagt agggacttga acgaacattt gtacaccaat   1320
gttcacagcg gctttattca caacagccaa aaggtggaag caacccagtg tccatggata   1380
gatgaataga taaataaaat gtggtataaa catacaatgg gctattgttt agccttaaaa   1440
gggaaggaaa ttctgacatg ctgcaatatg gatgaagctt aaagtcatta tgcaaagtgg   1500
aataagccta tcacaaaaaa taatattaca taattctact tatatgagga atctagagca   1560
gtcagtttca cagagacaga aaatagaatg gtggttgcca agggctggga gaagagggca   1620
atggagagtg agtgtttagt gggtcagagt tttagtttgg gaaggtaaaa agttctggag   1680
atggatgatg gttatgggtg ctcaacagtg tgaatgtact taatgccaca gaactgcaca   1740
tttaaatgtg gttaaaatca tcacttttat gttatgtata tttaccacaa taaataaaga   1800
agttgatatt tcttatactt acaaagagga gaagggcatt tgcaaatcaa caagaagtgt   1860
gaggcccctc tctctagcag aaaaatagac taaatctatt tctttatctt ttaacatcct   1920
gtttaaggga aatgccaaaa caaatgggaa aaaatacaca cacacaaata tatatgaaca   1980
tgttttgcct catgagtaat caaaatgtgt acatatgtat gtttatgtat gtgtgtttat   2040
atttaaaatc gtgttctgcc ttatgagtaa acaaaaagta tacaaattaa aaactataat   2100
gaaacgt                                                            2107
```

<210> SEQ ID NO 4
<211> LENGTH: 2107
<212> TYPE: DNA
<213> ORGANISM: Homo sapiens

<400> SEQUENCE: 4

```
aaaagcccgg gccgaacggc cccgccgcag agactcagcg cggatcgctg ctccctctcg     60
ccatggcgca ggtgctgatc gtgggcgccg ggatgacagg aagcttgtgc gctgcgctgc    120
tgaggaggca gacgtccggt cccttgtacc ttgctgtgtg gacaaggct gaggactcag    180 ggggaagaat gactacagcc tgcagtcctc ataatcctca gtgcacagct gacttgggtg    240
ctcagtacat cacctgcact cctcattatg ccaaaaaaca ccaacgtttt tatgatgaac    300
tgttagccta tggcgttttg aggcctctaa gctcgcctat tgaaggaatg gtgatgaaag    360
aaggagactg taacttttgtg gcacctcaag gaatttcttc aattattaag cattacttga    420
```

```
aagaatcagg tgcagaagtc tacttcagac atcgtgtgac acagatcaac ctaagagatg      480
acaaatggga agtatccaaa caaacaggct cccctgagca gtttgatctt attgttctca      540
caatgccagt tcctgagatt ctgcagcttc aaggtgacat caccacctta attagtgaat      600
gccaaaggca gcaactggag gctgtgagct actcctctcg atatgctctg ggcctctttt      660
atgaagctgg tacgaagatt gatgtccctt gggctgggca gtacatcacc agtaatccct      720
gcatacgctt cgtctccatt gataataaga agcgcaatat agagtcatca gaaattgggc      780
cttccctcgt gattcacacc actgtcccat ttggagttac atacttggaa cacagcattg      840
aggatgtgca agagttagtc ttccagcagc tggaaaacat tttgccgggt ttgcctcagc      900
caattgctac caaatgccaa aaatggagac attcacaggt accaagtgct ggtgtgattc      960
taggatgtgc gaagagcccc tggatgatgg cgattggatt tcccatctga cttcctggaa     1020
attggagcac acagtcaggt tttatttgat tttttttttt aaggatacca cttcacagcc     1080
tttaggatag ctattattta gaagcaaaac agaagataaa tgttggcaag gatgtggaga     1140
tattggattc ccttgtgcag tgccggtggg aatgtaaaat gatgtagcta ctatggaaaa     1200
tgatacggca atttctttag aaatgaaata tagaattgcc gtatgatctg cagttccaca     1260
tctggatatc tatccaaaag aagtgaaagt agggacttga acgaacattt gtacaccaat     1320
gttcacagcg gctttattca caacagccaa aaggtggaag caacccagtg tccatggata     1380
gatgaataga taaataaaat gtggtataaa catacaatgg gctattgttt agccttaaaa     1440
gggaaggaaa ttctgacatg ctgcaatatg gatgaagctt aaagtcatta tgcaaagtgg     1500
aataagccta tcacaaaaaa taatattaca taattctact tatatgagga atctagagca     1560
gtcagtttca cagagacaga aaatagaatg gtggttgcca agggctggga gaagagggca     1620
atggagagtg agtgtttagt gggtcagagt tttagtttgg gaaggtaaaa agttctggag     1680
atggatgatg gttatgggtg ctcaacagtg tgaatgtact taatgccaca gaactgcaca     1740
tttaaatgtg gttaaaatca tcactttat gttatgtata tttaccacaa taaataaaga     1800
agttgatatt tcttatactt acaaagagga gaagggcatt tgcaaatcaa caagaagtgt     1860
gaggcccctc tctctagcag aaaaatagac taaatctatt tctttatctt ttaacatcct     1920
gtttaaggga aatgccaaaa caaatgggaa aaaatacaca cacacaaata tatatgaaca     1980
tgttttgcct catgagtaat caaaatgtgt acatatgtat gtttatgtat gtgtgtttat     2040
atttaaaatc gtgttctgcc ttatgagtaa acaaaaagta tacaaattaa aaactataat     2100
gaaacgt                                                               2107
```

<210> SEQ ID NO 5
<211> LENGTH: 1924
<212> TYPE: DNA
<213> ORGANISM: Homo sapiens

<400> SEQUENCE: 5

```
ggggaagtct tgtgagatct gatggttttg taaagggcag ttgtacatat gctatcttgc       60
ctgccaccac taattagtga atgccaaagg cagcaactgg aggccgtgag ctactcctct      120
cgatatgctc tgggcctctt ttatgaagct ggtacgaaga ttgatgtccc ttgggctggg      180
cagtacatca ccagtaatcc ctgcatacgc ttcgtctcca ttgataataa gaagcgcaat      240
atagagtcat cagaaattgg gccttccctc gtgattcaca ccactgtccc atttggagtt      300
acatacttgg aacacagcat tgaggatgtg caagagttag tcttccagca gctgaaaaac      360
attttgccgg gtttgcctca gccaattgct accaaatgcc aaaaatggag acattcacag      420
```

```
attttgtttg gtgggggaag tggatgtgca cacagaagag cttgagacca cccgtacgtt      480
tacattatcc cctcatgaga ttaatttctg gttacaaatg ctgctgccaa ctgtcctggc      540
caaatgactc tgcatcacaa acctttcctt gcatgtggag gggatggatt tactcagtcc      600
aactttgatg gctgcatcac ttctgcccta tgtgttctgg aagctttaaa gaattatatt      660
tagtgcctat atccttattc tctacatgtg tattgggttt ttattttcac aattttctgt      720
tattgattat tttgttttct attttgctaa gaaaaattac tggaaaattg ttcttcactt      780
attatcattt ttcatgtgga gtataaaatc aattttgtaa ttttgatagt tacaacccat      840
gctagaatgg aaattcctca caccttgcac cttccctact tttctgaatt gctatgacta      900
ctccttgttg aaggaaaagt ggtacttaaa aataacaaa cgactctctc aaaaaaatta      960
cattaaatca caataacagt ttgtatgcca aaaacttgat tatccttatg aaaatttcaa     1020
ttctgaataa agaataatca cattatcaaa gccccatctt aagtcttcgg atgtgtcctt     1080
gaatcaataa ttttgcaaat tatacaaaac aagattttc caaaatgtag gtaacagagt     1140
gtaattctta tttctcattt atcccccaag ttattaagtg atcctgaatt gtaggtcata     1200
tatgtcatca tcttagtgtg gagggcaact tgactgataa agagaccttc cttcagattt     1260
tcagaaagta taagattcca catgattttc ccagccacac agtactttt aactttcaaa     1320 caaattccag tcctaatatg aaagataaaa attaaataga aacagagaga agtatatcg     1380 atccttacct tttgctatat tttatagctg ttgctgttac tttatgggct ctccagtatg     1440
tgctgtggca tttagactgt gtcgagttta atgaattaa cacaacaaaa aatttactga     1500
accagaaaat agatgcactt aaaatagttc aatatttgcc aagttggtgg ttcagcatat     1560
cacccacatg cttcagtgac ctgaccccac gacttgctag ctggagagaa atcaatctcc     1620
agccttccaa accagctacc tgttgctaat ttgaaaagca aaatgatgag ttctatttca     1680
gcattttgaa aggagaaaaa tcattgcagc ctctcaaact aacaaaagtt caacaaaaga     1740
cttcttactg taatagtgtt taaagtttca cacttacatg tccactgtca tacatacaca     1800
tacacaggca caggcagaac ttgcttctat agctgcaaag tgggtttat gaccctatag     1860 catattatta tatgtttcct cttagcaata aattggtgaa aaacttaaat gccaaaaaaa     1920
aaaa                                                                  1924

<210> SEQ ID NO 6
<211> LENGTH: 47
<212> TYPE: DNA
<213> ORGANISM: Artificial Sequence
<220> FEATURE:
<223> OTHER INFORMATION: Primer

<400> SEQUENCE: 6
tgcaggcacc gtcgtcgact taacaatgcg accccagggc cccgccg                    47

<210> SEQ ID NO 7
<211> LENGTH: 82
<212> TYPE: DNA
<213> ORGANISM: Artificial Sequence
<220> FEATURE:
<223> OTHER INFORMATION: Primer

<400> SEQUENCE: 7
catcaatgta tcttatcatg tctgatcaac cagctaccca tacgatgttc cagattacgc      60
tttttggtag ttcttcaata ag                                              82
```

-continued

```
<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
ttttggatcc atggcgcagg tgctgatcgt g                              31

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
ttttgaattc ctaaatataa ttctttaaag c                              31

<210> SEQ ID NO 10
<211> LENGTH: 4090
<212> TYPE: DNA
<213> ORGANISM: Homo sapiens
<220> FEATURE:
<221> NAME/KEY: CDS
<222> LOCATION: (182)..(1765)

<400> SEQUENCE: 10
gggcgctccc ggagtatcag caaaagggtt cgccccgccc acagtgcccg gctcccccg    60 ggtatcaaaa gaaggatcgg ctccgccccc gggctccccg ggggagttga tagaagggtc  120
cttcccaccc tttgccgtcc ccactcctgt gcctacgacc caggagcgtg tcagccaaag  180 c atg gag aat caa gag aag gcg agt atc gcg ggc cac atg ttc gac gta  229
  Met Glu Asn Gln Glu Lys Ala Ser Ile Ala Gly His Met Phe Asp Val
  1               5                  10                  15 gtc gtg atc gga ggt ggc att tca gga cta tct gct gcc aaa ctc ttg    277
Val Val Ile Gly Gly Gly Ile Ser Gly Leu Ser Ala Ala Lys Leu Leu
             20                  25                  30 act gaa tat ggc gtt agt gtt ttg gtt tta gaa gct cgg gac agg gtt    325
Thr Glu Tyr Gly Val Ser Val Leu Val Leu Glu Ala Arg Asp Arg Val
         35                  40                  45 gga gga aga aca tat act ata agg aat gag cat gtt gat tac gta gat    373
Gly Gly Arg Thr Tyr Thr Ile Arg Asn Glu His Val Asp Tyr Val Asp
     50                  55                  60 gtt ggt gga gct tat gtg gga cca acc caa aac aga atc tta cgc ttg    421
Val Gly Gly Ala Tyr Val Gly Pro Thr Gln Asn Arg Ile Leu Arg Leu
 65                  70                  75                  80 tct aag gag ctg ggc ata gag act tac aaa gtg aat gtc agt gag cgt    469
Ser Lys Glu Leu Gly Ile Glu Thr Tyr Lys Val Asn Val Ser Glu Arg
                 85                  90                  95 ctc gtt caa tat gtc aag ggg aaa aca tat cca ttt cgg ggc gcc ttt    517
Leu Val Gln Tyr Val Lys Gly Lys Thr Tyr Pro Phe Arg Gly Ala Phe
            100                 105                 110 cca cca gta tgg aat ccc att gca tat ttg gat tac aat aat ctg tgg    565
Pro Pro Val Trp Asn Pro Ile Ala Tyr Leu Asp Tyr Asn Asn Leu Trp
        115                 120                 125 agg aca ata gat aac atg ggg aag gag att cca act gat gca ccc tgg    613
Arg Thr Ile Asp Asn Met Gly Lys Glu Ile Pro Thr Asp Ala Pro Trp
    130                 135                 140 gag gct caa cat gct gac aaa tgg gac aaa atg acc atg aaa gag ctc    661
Glu Ala Gln His Ala Asp Lys Trp Asp Lys Met Thr Met Lys Glu Leu
145                 150                 155                 160
```

-continued

| | | |
|---|---|---|
| att gac aaa atc tgc tgg aca aag act gct agg cgg ttt gct tat ctt<br>Ile Asp Lys Ile Cys Trp Thr Lys Thr Ala Arg Arg Phe Ala Tyr Leu<br>                165                  170              175 | 709 | |
| ttt gtg aat atc aat gtg acc tct gag cct cac gaa gtg tct gcc ctg<br>Phe Val Asn Ile Asn Val Thr Ser Glu Pro His Glu Val Ser Ala Leu<br>            180                185              190 | 757 | |
| tgg ttc ttg tgg tat gtg aag cag tgc ggg ggc acc act cgg ata ttc<br>Trp Phe Leu Trp Tyr Val Lys Gln Cys Gly Gly Thr Thr Arg Ile Phe<br>           195                200              205 | 805 | |
| tct gtc acc aat ggt ggc cag gaa cgg aag ttt gta ggt gga tct ggt<br>Ser Val Thr Asn Gly Gly Gln Glu Arg Lys Phe Val Gly Gly Ser Gly<br>210                215              220 | 853 | |
| caa gtg agc gaa cgg ata atg gac ctc ctc gga gac caa gtg aag ctg<br>Gln Val Ser Glu Arg Ile Met Asp Leu Leu Gly Asp Gln Val Lys Leu<br>225                230              235              240 | 901 | |
| aac cat cct gtc act cac gtt gac cag tca agt gac aac atc atc ata<br>Asn His Pro Val Thr His Val Asp Gln Ser Ser Asp Asn Ile Ile Ile<br>            245                250              255 | 949 | |
| gag acg ctg aac cat gaa cat tat gag tgc aaa tac gta att aat gcg<br>Glu Thr Leu Asn His Glu His Tyr Glu Cys Lys Tyr Val Ile Asn Ala<br>            260                265              270 | 997 | |
| atc cct ccg acc ttg act gcc aag att cac ttc aga cca gag ctt cca<br>Ile Pro Pro Thr Leu Thr Ala Lys Ile His Phe Arg Pro Glu Leu Pro<br>            275                280              285 | 1045 | |
| gca gag aga aac cag tta att cag cgg ctt cca atg gga gct gtc att<br>Ala Glu Arg Asn Gln Leu Ile Gln Arg Leu Pro Met Gly Ala Val Ile<br>290                295              300 | 1093 | |
| aag tgc atg atg tat tac aag gag gcc ttc tgg aag aag aag gat tac<br>Lys Cys Met Met Tyr Tyr Lys Glu Ala Phe Trp Lys Lys Lys Asp Tyr<br>305                310              315              320 | 1141 | |
| tgt ggc tgc atg atc att gaa gat gaa gat gct cca att tca ata acc<br>Cys Gly Cys Met Ile Ile Glu Asp Glu Asp Ala Pro Ile Ser Ile Thr<br>            325                330              335 | 1189 | |
| ttg gat gac acc aag cca gat ggg tca ctg cct gcc atc atg ggc ttc<br>Leu Asp Asp Thr Lys Pro Asp Gly Ser Leu Pro Ala Ile Met Gly Phe<br>            340                345              350 | 1237 | |
| att ctt gcc cgg aaa gct gat cga ctt gct aag cta cat aag gaa ata<br>Ile Leu Ala Arg Lys Ala Asp Arg Leu Ala Lys Leu His Lys Glu Ile<br>            355                360              365 | 1285 | |
| agg aag aag aaa atc tgt gag ctc tat gcc aaa gtg ctg gga tcc caa<br>Arg Lys Lys Lys Ile Cys Glu Leu Tyr Ala Lys Val Leu Gly Ser Gln<br>370                375              380 | 1333 | |
| gaa gct tta cat cca gtg cat tat gaa gag aag aac tgg tgt gag gag<br>Glu Ala Leu His Pro Val His Tyr Glu Glu Lys Asn Trp Cys Glu Glu<br>385                390              395              400 | 1381 | |
| cag tac tct ggg ggc tgc tac acg gcc tac ttc cct cct ggg atc atg<br>Gln Tyr Ser Gly Gly Cys Tyr Thr Ala Tyr Phe Pro Pro Gly Ile Met<br>            405                410              415 | 1429 | |
| act caa tat gga agg gtg att cgt caa ccc gtg ggc agg att ttc ttt<br>Thr Gln Tyr Gly Arg Val Ile Arg Gln Pro Val Gly Arg Ile Phe Phe<br>            420                425              430 | 1477 | |
| gcg ggc aca gag act gcc aca aag tgg agc ggc tac atg gaa ggg gca<br>Ala Gly Thr Glu Thr Ala Thr Lys Trp Ser Gly Tyr Met Glu Gly Ala<br>            435                440              445 | 1525 | |
| gtt gag gct gga gaa cga gca gct agg gag gtc tta aat ggt ctc ggg<br>Val Glu Ala Gly Glu Arg Ala Ala Arg Glu Val Leu Asn Gly Leu Gly<br>450                455              460 | 1573 | |
| aag gtg acc gag aaa gat atc tgg gta caa gaa cct gaa tca aag gac<br>Lys Val Thr Glu Lys Asp Ile Trp Val Gln Glu Pro Glu Ser Lys Asp<br>465                470              475              480 | 1621 | |

| | | | | | | | | | | | | | | | |
|---|---|---|---|---|---|---|---|---|---|---|---|---|---|---|---|
| gtt | cca | gcg | gta | gaa | atc | acc | cac | acc | ttc | tgg | gaa | agg | aac | ctg | ccc |
| Val | Pro | Ala | Val | Glu | Ile | Thr | His | Thr | Phe | Trp | Glu | Arg | Asn | Leu | Pro |
| | | | | 485 | | | | | 490 | | | | | 495 | |

1669

| | | | | | | | | | | | | | | | |
|---|---|---|---|---|---|---|---|---|---|---|---|---|---|---|---|
| tct | gtt | tct | ggc | ctg | ctg | aag | atc | att | gga | ttt | tcc | aca | tca | gta | act |
| Ser | Val | Ser | Gly | Leu | Leu | Lys | Ile | Ile | Gly | Phe | Ser | Thr | Ser | Val | Thr |
| | | | 500 | | | | | 505 | | | | | 510 | | |

1717

| | | | | | | | | | | | | |
|---|---|---|---|---|---|---|---|---|---|---|---|---|
| gcc | ctg | ggg | ttt | gtg | ctg | tac | aaa | tac | aag | ctc | ctg | cca | cgg | tct | tga |
| Ala | Leu | Gly | Phe | Val | Leu | Tyr | Lys | Tyr | Lys | Leu | Leu | Pro | Arg | Ser | |
| | | 515 | | | | 520 | | | | 525 | | | | | |

1765

```
agttctgttc ttatgctctc tgctcactgg ttttcaatac caccaagagg aaaatattga    1825
caagtttaaa ggctgtgtca ttgggccatg tttaagtgta ctggatttaa ctacctttgg    1885
cttaattcca atcattgtta aagtaaaaac aattcaaaga atcacctaat taatttcagt    1945
aagatcaagc tccatcttat ttgtcagtgt agatcaactc atgttaattg atagaataaa    2005
gccttgtgat cactttctga aattcacaaa gttaaacgtg atgtgctcat cagaaacaat    2065
ttctgtgtcc tgtttttatt cccttcaatg caaaatacat gatgatttca gaaacaaagc    2125
atttgacttt ctgtctgtgg aggtggagta ggtgaaggcc cagcctgtaa ctgtcctttt    2185
tcttccctta ggcaatggtg aactgtcatt acagagccta gaggctcaca gcctcctgga    2245
ggaagcagcc tccactttgg atcaggaaat agtaaaggaa agcagtgttg ggggtagcgg    2305
catgcagacc ctcagaccag aatggggaca tcttgtggtc tgctgcctca ggaatctcct    2365
gaccacttgt agtccctccg acttctctag acatctagtc tcagtgctag cttatttgta    2425
tttttcctct ttcacttctt atggaggaga gtgtttaact gagttagaat gttgaaactg    2485
acttgctgtg acttatgtgc agctttccag ttgagcagag gaaaatagtg gcaggactgt    2545
cccccaggag gactccctgc ttagctctgt gggagaccaa ctacgactgg catcttctct    2605
tcccccctgga aggcagctag acaccaatgg atccttgtca gttgtaacat tctatttcaa    2665
cttcaggaaa gcagcagttt tcttttaatt tttcctatga ccataaaatt agacatacct    2725
ctcaacttac atatgtcttc aacatggtta cctctgcata aatattagca aagcatgcca    2785
atttctctta agtactgaaa tacatatgat aaatttgact gttatttgtt gagactatca    2845
aacagaaaag aaattagggc tctaatttcc ttaaagcaag ctcacttgct ttagttgtta    2905
agttttataa aagacatgaa attgagtcat tttatatatg aaaactaagt tctctatctt    2965
aggagtaatg tcggcccaca agggtgccca cctcttgttt tccccttttta aaaactcaga    3025
ttttaaaag ccctttccaa aggtttcaac tgtaaaatac ttcttttac aatgtatcaa    3085
catatttta tttaagggga attaacaatt gccagggaaa ccagccaacc caagtttatt    3145
atatcattaa ccttatcata aattcaaacc taagttgctg gaccctggtg tgaggacata    3205
aatcttccaa agttttgcct atcctaagag ctgcattttt ctactgctct ttaccttgca    3265
ttttagctaa tttaggagtt ttgagaatgt attggatacg ctccagtaca taaggagttg    3325
ccgcatatta tatcagactg ctttgagaaa tctcatccct agtctattgc agttgtttct    3385
attagcttac tgattaactc agtcctgaca cacctttggg gaaatgctga tttaaacttc    3445
ttaactggca acagttggaa cagtaatcag tttgctaaca tatttaaagt cttgaatgtt    3505
gaagaactca tgtgatttac ccttttcaac tttttggaaa acgatttaat ttattctaat    3565
tagattaacc ctattaatct atggattggg tatcaaaatg aatgccagtc cagatgtgcc    3625
tagacacgaa attggagctg aggactctca cgatatgcaa gttcatccaa cgtgaagata    3685
ccataagctt tttctctgaa ccagagaaat gaaagtcagt ttaagaggct gatagatctt    3745
ggccctgtta aggcatccac ttcacagttc tgaaggctga gtcagcccca ctccacagtt    3805
```

-continued

```
aggccaagaa ttagatttta aaacttcatc tgtctgtccc agttaactgt taaataaggc    3865
ctcatcctcc actgaagagt atggattgaa ggattgtgaa ctatgtttag tgtgattgtg    3925
aacttggtgc ctaatgttcc atgtctgaag tttgccccag tgctacacgt tggagtatac    3985
ctatgtgtgt gctttgccac tgaagtaaga ttttgcctgt atggtactgt tttgtttgtt    4045
aataaagtgc actgccaccc ccaatgcaaa aaaaaaaaaa aaaaa                   4090
```

<210> SEQ ID NO 11
<211> LENGTH: 527
<212> TYPE: PRT
<213> ORGANISM: Homo sapiens

<400> SEQUENCE: 11

| Met | Glu | Asn | Gln | Glu | Lys | Ala | Ser | Ile | Ala | Gly | His | Met | Phe | Asp | Val |
|---|---|---|---|---|---|---|---|---|---|---|---|---|---|---|---|
| 1 | | | | 5 | | | | | 10 | | | | | 15 | |

| Val | Val | Ile | Gly | Gly | Gly | Ile | Ser | Gly | Leu | Ser | Ala | Ala | Lys | Leu | Leu |
|---|---|---|---|---|---|---|---|---|---|---|---|---|---|---|---|
| | | | 20 | | | | | 25 | | | | | 30 | | |

| Thr | Glu | Tyr | Gly | Val | Ser | Val | Leu | Val | Leu | Glu | Ala | Arg | Asp | Arg | Val |
|---|---|---|---|---|---|---|---|---|---|---|---|---|---|---|---|
| | | | 35 | | | | | 40 | | | | | 45 | | |

| Gly | Gly | Arg | Thr | Tyr | Thr | Ile | Arg | Asn | Glu | His | Val | Asp | Tyr | Val | Asp |
|---|---|---|---|---|---|---|---|---|---|---|---|---|---|---|---|
| | 50 | | | | | 55 | | | | | 60 | | | | |

| Val | Gly | Gly | Ala | Tyr | Val | Gly | Pro | Thr | Gln | Asn | Arg | Ile | Leu | Arg | Leu |
|---|---|---|---|---|---|---|---|---|---|---|---|---|---|---|---|
| 65 | | | | | 70 | | | | | 75 | | | | | 80 |

| Ser | Lys | Glu | Leu | Gly | Ile | Glu | Thr | Tyr | Lys | Val | Asn | Val | Ser | Glu | Arg |
|---|---|---|---|---|---|---|---|---|---|---|---|---|---|---|---|
| | | | | 85 | | | | | 90 | | | | | 95 | |

| Leu | Val | Gln | Tyr | Val | Lys | Gly | Lys | Thr | Tyr | Pro | Phe | Arg | Gly | Ala | Phe |
|---|---|---|---|---|---|---|---|---|---|---|---|---|---|---|---|
| | | | | 100 | | | | | 105 | | | | | 110 | |

| Pro | Pro | Val | Trp | Asn | Pro | Ile | Ala | Tyr | Leu | Asp | Tyr | Asn | Asn | Leu | Trp |
|---|---|---|---|---|---|---|---|---|---|---|---|---|---|---|---|
| | | | 115 | | | | | 120 | | | | | 125 | | |

| Arg | Thr | Ile | Asp | Asn | Met | Gly | Lys | Glu | Ile | Pro | Thr | Asp | Ala | Pro | Trp |
|---|---|---|---|---|---|---|---|---|---|---|---|---|---|---|---|
| | 130 | | | | | 135 | | | | | 140 | | | | |

| Glu | Ala | Gln | His | Ala | Asp | Lys | Trp | Asp | Lys | Met | Thr | Met | Lys | Glu | Leu |
|---|---|---|---|---|---|---|---|---|---|---|---|---|---|---|---|
| 145 | | | | | 150 | | | | | 155 | | | | | 160 |

| Ile | Asp | Lys | Ile | Cys | Trp | Thr | Lys | Thr | Ala | Arg | Arg | Phe | Ala | Tyr | Leu |
|---|---|---|---|---|---|---|---|---|---|---|---|---|---|---|---|
| | | | | 165 | | | | | 170 | | | | | 175 | |

| Phe | Val | Asn | Ile | Asn | Val | Thr | Ser | Glu | Pro | His | Glu | Val | Ser | Ala | Leu |
|---|---|---|---|---|---|---|---|---|---|---|---|---|---|---|---|
| | | | | 180 | | | | | 185 | | | | | 190 | |

| Trp | Phe | Leu | Trp | Tyr | Val | Lys | Gln | Cys | Gly | Gly | Thr | Thr | Arg | Ile | Phe |
|---|---|---|---|---|---|---|---|---|---|---|---|---|---|---|---|
| | | | 195 | | | | | 200 | | | | | 205 | | |

| Ser | Val | Thr | Asn | Gly | Gly | Gln | Glu | Arg | Lys | Phe | Val | Gly | Gly | Ser | Gly |
|---|---|---|---|---|---|---|---|---|---|---|---|---|---|---|---|
| | 210 | | | | | 215 | | | | | 220 | | | | |

| Gln | Val | Ser | Glu | Arg | Ile | Met | Asp | Leu | Leu | Gly | Asp | Gln | Val | Lys | Leu |
|---|---|---|---|---|---|---|---|---|---|---|---|---|---|---|---|
| 225 | | | | | 230 | | | | | 235 | | | | | 240 |

| Asn | His | Pro | Val | Thr | His | Val | Asp | Gln | Ser | Ser | Asp | Asn | Ile | Ile | Ile |
|---|---|---|---|---|---|---|---|---|---|---|---|---|---|---|---|
| | | | | 245 | | | | | 250 | | | | | 255 | |

| Glu | Thr | Leu | Asn | His | Glu | His | Tyr | Glu | Cys | Lys | Tyr | Val | Ile | Asn | Ala |
|---|---|---|---|---|---|---|---|---|---|---|---|---|---|---|---|
| | | | | 260 | | | | | 265 | | | | | 270 | |

| Ile | Pro | Pro | Thr | Leu | Thr | Ala | Lys | Ile | His | Phe | Arg | Pro | Glu | Leu | Pro |
|---|---|---|---|---|---|---|---|---|---|---|---|---|---|---|---|
| | | | 275 | | | | | 280 | | | | | 285 | | |

| Ala | Glu | Arg | Asn | Gln | Leu | Ile | Gln | Arg | Leu | Pro | Met | Gly | Ala | Val | Ile |
|---|---|---|---|---|---|---|---|---|---|---|---|---|---|---|---|
| | 290 | | | | | 295 | | | | | 300 | | | | |

| Lys | Cys | Met | Met | Tyr | Tyr | Lys | Glu | Ala | Phe | Trp | Lys | Lys | Lys | Asp | Tyr |
|---|---|---|---|---|---|---|---|---|---|---|---|---|---|---|---|
| 305 | | | | | 310 | | | | | 315 | | | | | 320 |

-continued

```
Cys Gly Cys Met Ile Ile Glu Asp Glu Asp Ala Pro Ile Ser Ile Thr
            325                 330                 335

Leu Asp Asp Thr Lys Pro Asp Gly Ser Leu Pro Ala Ile Met Gly Phe
            340                 345                 350

Ile Leu Ala Arg Lys Ala Asp Arg Leu Ala Lys Leu His Lys Glu Ile
            355                 360                 365

Arg Lys Lys Lys Ile Cys Glu Leu Tyr Ala Lys Val Leu Gly Ser Gln
370                 375                 380

Glu Ala Leu His Pro Val His Tyr Glu Glu Lys Asn Trp Cys Glu Glu
385                 390                 395                 400

Gln Tyr Ser Gly Gly Cys Tyr Thr Ala Tyr Phe Pro Pro Gly Ile Met
            405                 410                 415

Thr Gln Tyr Gly Arg Val Ile Arg Gln Pro Val Gly Arg Ile Phe Phe
            420                 425                 430

Ala Gly Thr Glu Thr Ala Thr Lys Trp Ser Gly Tyr Met Glu Gly Ala
            435                 440                 445

Val Glu Ala Gly Glu Arg Ala Ala Arg Glu Val Leu Asn Gly Leu Gly
    450                 455                 460

Lys Val Thr Glu Lys Asp Ile Trp Val Gln Pro Glu Ser Lys Asp
465                 470                 475                 480

Val Pro Ala Val Glu Ile Thr His Thr Phe Trp Glu Arg Asn Leu Pro
                485                 490                 495

Ser Val Ser Gly Leu Leu Lys Ile Ile Gly Phe Ser Thr Ser Val Thr
            500                 505                 510

Ala Leu Gly Phe Val Leu Tyr Lys Tyr Lys Leu Leu Pro Arg Ser
            515                 520                 525
```

<210> SEQ ID NO 12
<211> LENGTH: 2566
<212> TYPE: DNA
<213> ORGANISM: Homo sapiens
<220> FEATURE:
<221> NAME/KEY: CDS
<222> LOCATION: (137)..(1699)

<400> SEQUENCE: 12

```
cgaggcgctg gtgcacgggg gcagcgcgca gcaggccggc gggcaggcgg gcgggctggc      60
tggcaggcag gactgggatc gaggcccaga aaacggagca gcgggcacca gggaggcctg     120
gaacggggcg agcgcc atg agc aac aaa tgc gac gtg gtc gtg gtg ggg ggc     172
                  Met Ser Asn Lys Cys Asp Val Val Val Val Gly Gly
                    1               5                  10 ggc atc tca ggt atg gca gca gcc aaa ctt ctg cat gac tct gga ctg       220
Gly Ile Ser Gly Met Ala Ala Ala Lys Leu Leu His Asp Ser Gly Leu
            15                  20                  25 aat gtg gtt gtt ctg gaa gcc cgg gac cgt gtg gga ggc agg act tac       268
Asn Val Val Val Leu Glu Ala Arg Asp Arg Val Gly Gly Arg Thr Tyr
        30                  35                  40 act ctt agg aac caa aag gtt aaa tat gtg gac ctt gga gga tcc tat       316
Thr Leu Arg Asn Gln Lys Val Lys Tyr Val Asp Leu Gly Gly Ser Tyr
45                  50                  55                  60 gtt gga cca acc cag aat cgt atc ttg aga tta gcc aag gag cta gga       364
Val Gly Pro Thr Gln Asn Arg Ile Leu Arg Leu Ala Lys Glu Leu Gly
                65                  70                  75 ttg gag acc tac aaa gtg aat gag gtt gag cgt ctg atc cac cat gta       412
Leu Glu Thr Tyr Lys Val Asn Glu Val Glu Arg Leu Ile His His Val
            80                  85                  90
```

```
aag ggc aaa tca tac ccc ttc agg ggg cca ttc cca cct gta tgg aat    460
Lys Gly Lys Ser Tyr Pro Phe Arg Gly Pro Phe Pro Pro Val Trp Asn
            95              100                 105 cca att acc tac tta gat cat aac aac ttt tgg agg aca atg gat gac    508
Pro Ile Thr Tyr Leu Asp His Asn Asn Phe Trp Arg Thr Met Asp Asp
    110                 115                 120 atg ggg cga gag att ccg agt gat gcc cca tgg aag gct ccc ctt gca    556
Met Gly Arg Glu Ile Pro Ser Asp Ala Pro Trp Lys Ala Pro Leu Ala
125                 130                 135                 140 gaa gag tgg gac aac atg aca atg aag gag cta ctg gac aag ctc tgc    604
Glu Glu Trp Asp Asn Met Thr Met Lys Glu Leu Leu Asp Lys Leu Cys
                145                 150                 155 tgg act gaa tct gca aag cag ctt gcc act ctc ttt gtg aac ctg tgt    652
Trp Thr Glu Ser Ala Lys Gln Leu Ala Thr Leu Phe Val Asn Leu Cys
            160                 165                 170 gtc act gca gag acc cat gag gtc tct gct ctc tgg ttc ctg tgg tat    700
Val Thr Ala Glu Thr His Glu Val Ser Ala Leu Trp Phe Leu Trp Tyr
        175                 180                 185 gtg aag cag tgt gga ggc aca aca aga atc atc tcg aca aca aat gga    748
Val Lys Gln Cys Gly Gly Thr Thr Arg Ile Ile Ser Thr Thr Asn Gly
    190                 195                 200 gga cag gag agg aaa ttt gtg ggc gga tct ggt caa gtg agt gag cgg    796
Gly Gln Glu Arg Lys Phe Val Gly Gly Ser Gly Gln Val Ser Glu Arg
205                 210                 215                 220 ata atg gac ctc ctt gga gac cga gtg aag ctg gag agg cct gtg atc    844
Ile Met Asp Leu Leu Gly Asp Arg Val Lys Leu Glu Arg Pro Val Ile
                225                 230                 235 tac att gac cag aca aga gaa aat gtc ctt gtg gag acc cta aac cat    892
Tyr Ile Asp Gln Thr Arg Glu Asn Val Leu Val Glu Thr Leu Asn His
            240                 245                 250 gag atg tat gag gct aaa tat gtg att agt gct att cct cct act ctg    940
Glu Met Tyr Glu Ala Lys Tyr Val Ile Ser Ala Ile Pro Pro Thr Leu
        255                 260                 265 ggc atg aag att cac ttc aat ccc cct ctg cca atg atg aga aac cag    988
Gly Met Lys Ile His Phe Asn Pro Pro Leu Pro Met Met Arg Asn Gln
    270                 275                 280 atg atc act cgt gtg cct ttg ggt tca gtc atc aag tgt ata gtt tat   1036
Met Ile Thr Arg Val Pro Leu Gly Ser Val Ile Lys Cys Ile Val Tyr
285                 290                 295                 300 tat aaa gag cct ttc tgg agg aaa aag gat tac tgt gga acc atg att   1084
Tyr Lys Glu Pro Phe Trp Arg Lys Lys Asp Tyr Cys Gly Thr Met Ile
                305                 310                 315 att gat gga gaa gaa gct cca gtt gcc tac acg ttg gat gat acc aaa   1132
Ile Asp Gly Glu Glu Ala Pro Val Ala Tyr Thr Leu Asp Asp Thr Lys
            320                 325                 330 cct gaa ggc aac tat gct gcc ata atg gga ttt atc ctg gcc cac aaa   1180
Pro Glu Gly Asn Tyr Ala Ala Ile Met Gly Phe Ile Leu Ala His Lys
        335                 340                 345 gcc aga aaa ctg gca cgt ctt acc aaa gag gaa agg ttg aag aaa ctt   1228
Ala Arg Lys Leu Ala Arg Leu Thr Lys Glu Glu Arg Leu Lys Lys Leu
    350                 355                 360 tgt gaa ctc tat gcc aag gtt ctg ggt tcc cta gaa gct ctg gag cca   1276
Cys Glu Leu Tyr Ala Lys Val Leu Gly Ser Leu Glu Ala Leu Glu Pro
365                 370                 375                 380 gtg cat tat gaa gaa aag aac tgg tgt gag gag cag tac tct ggg ggc   1324
Val His Tyr Glu Glu Lys Asn Trp Cys Glu Glu Gln Tyr Ser Gly Gly
                385                 390                 395 tgc tac aca act tat ttc ccc cct ggg atc ctg act caa tat gga agg   1372
Cys Tyr Thr Thr Tyr Phe Pro Pro Gly Ile Leu Thr Gln Tyr Gly Arg
            400                 405                 410
```

```
gtt cta cgc cag cca gtg gac agg att tac ttt gca ggc acc gag act    1420
Val Leu Arg Gln Pro Val Asp Arg Ile Tyr Phe Ala Gly Thr Glu Thr
        415                 420                 425 gcc aca cac tgg agc ggc tac atg gag ggg gct gta gag gcc ggg gag    1468
Ala Thr His Trp Ser Gly Tyr Met Glu Gly Ala Val Glu Ala Gly Glu
        430                 435                 440 aga gca gcc cga gag atc ctg cat gcc atg ggg aag att cca gag gat    1516
Arg Ala Ala Arg Glu Ile Leu His Ala Met Gly Lys Ile Pro Glu Asp
445                 450                 455                 460 gaa atc tgg cag tca gaa cca gag tct gtg gat gtc cct gca cag ccc    1564
Glu Ile Trp Gln Ser Glu Pro Glu Ser Val Asp Val Pro Ala Gln Pro
                465                 470                 475 atc acc acc acc ttt ttg gag aga cat ttg ccc tcc gtg cca ggc ctg    1612
Ile Thr Thr Thr Phe Leu Glu Arg His Leu Pro Ser Val Pro Gly Leu
        480                 485                 490 ctc agg ctg att gga ttg acc acc atc ttt tca gca acg gct ctt ggc    1660
Leu Arg Leu Ile Gly Leu Thr Thr Ile Phe Ser Ala Thr Ala Leu Gly
        495                 500                 505 ttc ctg gcc cac aaa agg ggg cta ctt gtg aga gtc taa agagagagg      1709
Phe Leu Ala His Lys Arg Gly Leu Leu Val Arg Val
        510                 515                 520 tgtctgtaat cacactctct tcttactgta tttgggatat gagtttgggg aaagagttgc  1769
agtaaagttc catgaagaca atagtgtgg agtgaggcgg ggagcatgaa gataaatcca  1829
actctgactg taaaatacat ggtatctctt tctccgttgt ggcccctgct tagtgtccct  1889
tacctggctt agcgttctgt ttcaccagtt tccaagttta ttgccctcaa aatctttaga  1949
atagttaaat tggcttgttt aaggttcttg ctgccccaca acacaccttg cccatgcaca  2009
aggaatgaat tttttcctac cattatggct ttgtgcttgt tcttcctctt acctgtaata  2069
gcctcacctt ccctagttct ttgcattcgt ccttagaata ctgtattgtt acagctgaaa  2129
gacagtaaag accatttagt cctcaccttc tgttttagag ttgagcaaac tgaagcccac  2189
agaggtggaa cttaattacc taagagccac aataagccac tggtatctgg gggactagaa  2249
cacaaatcca acgcttttcc cacctctttg gatgttttcc ccaattatcc tccttcactc  2309
cctgtcatag ttaccgatgg tgtcccgttg tgtgggttta ctctgtgcta agttgtctta  2369
cacttctcaa atgctactca gtatatagcc ttaagtctta ctgttttgtg cggtgtgtct  2429
ccagctgatt ttaactttt tgatggtaga aatttatct cttcttccctt ttgtatcctc   2489
cattgtatct tcatacaaag gacagtacac acttgggtaa ttaaaaataa aagttgattg  2549
accataaaaa aaaaaaa                                                 2566
```

<210> SEQ ID NO 13
<211> LENGTH: 520
<212> TYPE: PRT
<213> ORGANISM: Homo sapiens

<400> SEQUENCE: 13

Met Ser Asn Lys Cys Asp Val Val Val Gly Gly Gly Ile Ser Gly
1               5                   10                  15

Met Ala Ala Ala Lys Leu Leu His Asp Ser Gly Leu Asn Val Val
                20                  25                  30

Leu Glu Ala Arg Asp Arg Val Gly Gly Arg Thr Tyr Thr Leu Arg Asn
            35                  40                  45

Gln Lys Val Lys Tyr Val Asp Leu Gly Gly Ser Tyr Val Gly Pro Thr
        50                  55                  60

-continued

```
Gln Asn Arg Ile Leu Arg Leu Ala Lys Glu Leu Gly Leu Glu Thr Tyr
 65                  70                  75                  80

Lys Val Asn Glu Val Glu Arg Leu Ile His Val Lys Gly Lys Ser
                 85                  90                  95

Tyr Pro Phe Arg Gly Pro Phe Pro Val Trp Asn Pro Ile Thr Tyr
            100                 105                 110

Leu Asp His Asn Asn Phe Trp Arg Thr Met Asp Asp Met Gly Arg Glu
            115                 120                 125

Ile Pro Ser Asp Ala Pro Trp Lys Ala Pro Leu Ala Glu Glu Trp Asp
130                 135                 140

Asn Met Thr Met Lys Glu Leu Leu Asp Lys Leu Cys Trp Thr Glu Ser
145                 150                 155                 160

Ala Lys Gln Leu Ala Thr Leu Phe Val Asn Leu Cys Val Thr Ala Glu
                165                 170                 175

Thr His Glu Val Ser Ala Leu Trp Phe Leu Trp Tyr Val Lys Gln Cys
            180                 185                 190

Gly Gly Thr Thr Arg Ile Ile Ser Thr Thr Asn Gly Gly Gln Glu Arg
            195                 200                 205

Lys Phe Val Gly Gly Ser Gly Gln Val Ser Glu Arg Ile Met Asp Leu
210                 215                 220

Leu Gly Asp Arg Val Lys Leu Glu Arg Pro Val Ile Tyr Ile Asp Gln
225                 230                 235                 240

Thr Arg Glu Asn Val Leu Val Glu Thr Leu Asn His Glu Met Tyr Glu
                245                 250                 255

Ala Lys Tyr Val Ile Ser Ala Ile Pro Pro Thr Leu Gly Met Lys Ile
            260                 265                 270

His Phe Asn Pro Pro Leu Pro Met Met Arg Asn Gln Met Ile Thr Arg
            275                 280                 285

Val Pro Leu Gly Ser Val Ile Lys Cys Ile Val Tyr Tyr Lys Glu Pro
290                 295                 300

Phe Trp Arg Lys Lys Asp Tyr Cys Gly Thr Met Ile Ile Asp Gly Glu
305                 310                 315                 320

Glu Ala Pro Val Ala Tyr Thr Leu Asp Asp Thr Lys Pro Glu Gly Asn
                325                 330                 335

Tyr Ala Ala Ile Met Gly Phe Ile Leu Ala His Lys Ala Arg Lys Leu
            340                 345                 350

Ala Arg Leu Thr Lys Glu Arg Leu Lys Lys Leu Cys Glu Leu Tyr
            355                 360                 365

Ala Lys Val Leu Gly Ser Leu Glu Ala Leu Glu Pro Val His Tyr Glu
370                 375                 380

Glu Lys Asn Trp Cys Glu Glu Gln Tyr Ser Gly Gly Cys Tyr Thr Thr
385                 390                 395                 400

Tyr Phe Pro Pro Gly Ile Leu Thr Gln Tyr Gly Arg Val Leu Arg Gln
                405                 410                 415

Pro Val Asp Arg Ile Tyr Phe Ala Gly Thr Glu Thr Ala Thr His Trp
            420                 425                 430

Ser Gly Tyr Met Glu Gly Ala Val Glu Ala Gly Glu Arg Ala Ala Arg
            435                 440                 445

Glu Ile Leu His Ala Met Gly Lys Ile Pro Glu Asp Glu Ile Trp Gln
            450                 455                 460

Ser Glu Pro Glu Ser Val Asp Val Pro Ala Gln Pro Ile Thr Thr Thr
465                 470                 475                 480
```

-continued

```
Phe Leu Glu Arg His Leu Pro Ser Val Pro Gly Leu Leu Arg Leu Ile
                485                 490                 495

Gly Leu Thr Thr Ile Phe Ser Ala Thr Ala Leu Gly Phe Leu Ala His
                500                 505                 510

Lys Arg Gly Leu Leu Val Arg Val
            515                 520
```